US012623015B2

(12) United States Patent (10) Patent No.: US 12,623,015 B2
Tillman et al. (45) Date of Patent: May 12, 2026

(54) MULTI-LUMEN IMPLANTABLE DEVICE

(71) Applicant: University of Pittsburgh—Of the Commonwealth System of Higher Education, Pittsburgh, PA (US)

(72) Inventors: Bryan W. Tillman, Delaware, OH (US); Youngjae Chun, Wexford, PA (US)

(73) Assignee: University of Pittsburgh—Of the Commonwealth System of Higher Education, Pittsburgh, PA (US)

( * ) Notice: Subject to any disclaimer, the term of this patent is extended or adjusted under 35 U.S.C. 154(b) by 588 days.

(21) Appl. No.: 17/797,070

(22) PCT Filed: Jan. 22, 2021

(86) PCT No.: PCT/US2021/014661
§ 371 (c)(1),
(2) Date: Aug. 2, 2022

(87) PCT Pub. No.: WO2021/158377
PCT Pub. Date: Aug. 12, 2021

(65) Prior Publication Data
US 2023/0059358 A1 Feb. 23, 2023

Related U.S. Application Data

(60) Provisional application No. 62/970,023, filed on Feb. 4, 2020.

(51) Int. Cl.
*A61M 1/36* (2006.01)
*A61F 2/958* (2013.01)
(Continued)

(52) U.S. Cl.
CPC ........... *A61M 1/3659* (2014.02); *A61F 2/958* (2013.01); *A61M 25/0032* (2013.01);
(Continued)

(58) Field of Classification Search
CPC ............ A61M 1/3659; A61M 25/0032; A61M 25/1011; A61M 2025/0031;
(Continued)

(56) References Cited

U.S. PATENT DOCUMENTS 5,395,333 A * 3/1995 Brill ................... A61M 25/1011
604/101.05
8,876,752 B2 * 11/2014 Hayakawa .......... A61M 1/3661
604/29

(Continued)

FOREIGN PATENT DOCUMENTS

EP 3248645 11/2017
WO WO 2011/112463 9/2011

OTHER PUBLICATIONS

International Search Report and Written Opinion dated Jun. 4, 2021, from International Application No. PCT/2021/014661, 17 pp.

(Continued)

*Primary Examiner* — Guy K Townsend
*Assistant Examiner* — Alessandro R Del Priore
(74) *Attorney, Agent, or Firm* — Klarquist Sparkman, LLP

(57) ABSTRACT

A multi-lumen implantable device configured to deliver a therapeutic agent to a selected portion of a blood vessel is disclosed. As one example, an implantable device includes a first lumen configured to flow blood from an upstream end to a downstream end of the device when implanted in a blood vessel; a second lumen fluidly separated from the first lumen and configured for introducing a therapeutic agent to a selected, first portion of a wall of the blood vessel, between the upstream end and the downstream end of the device; and at least one sealing member configured to block the thera- (Continued)

peutic agent from entering a second portion of the wall of the blood vessel, between the upstream end and the downstream end of the device.

19 Claims, 28 Drawing Sheets

(51) Int. Cl.
*A61M 25/00* (2006.01)
*A61M 25/10* (2013.01)
(52) U.S. Cl.
CPC .. *A61M 25/1011* (2013.01); *A61F 2250/0067* (2013.01); *A61M 2025/0031* (2013.01); *A61M 2025/0037* (2013.01); *A61M 2025/1095* (2013.01)
(58) Field of Classification Search
CPC .. A61M 2025/0037; A61M 2025/1095; A61M 2025/105; A61M 2025/1097; A61M 25/00; A61F 2/958; A61F 2250/0067; A61F 2007/126; A61F 7/12; A61F 2230/001; A61F 2/07; A61F 2002/061; A61F 2250/0039; A61F 2250/0069; A61F 2/06
See application file for complete search history.

(56) References Cited

U.S. PATENT DOCUMENTS

| | | | |
|---|---|---|---|
| 2004/0006299 A1 | 1/2004 | Barbut | |
| 2008/0269866 A1* | 10/2008 | Hamer | A61F 2/07 623/1.11 |
| 2010/0076484 A1* | 3/2010 | Riina | A61F 2/958 604/509 |
| 2011/0230830 A1* | 9/2011 | Gifford, III | A61F 2/07 604/96.01 |
| 2011/0282274 A1* | 11/2011 | Fulton, III | A61B 17/12136 604/27 |
| 2013/0331762 A1 | 12/2013 | Kassab et al. | |
| 2016/0022409 A1 | 1/2016 | Aharon et al. | |
| 2017/0164605 A1 | 6/2017 | Tillman et al. | |
| 2019/0246631 A1 | 8/2019 | Tillman et al. | |

OTHER PUBLICATIONS

Extended European Search Report dated May 24, 2023, from European Patent Application No. 21751272.2, 11 pp.

* cited by examiner

Pump/Warmer

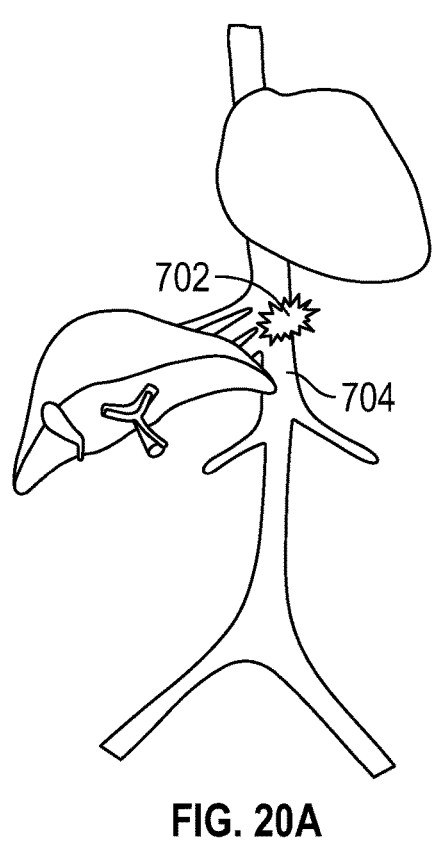
FIG. 20A
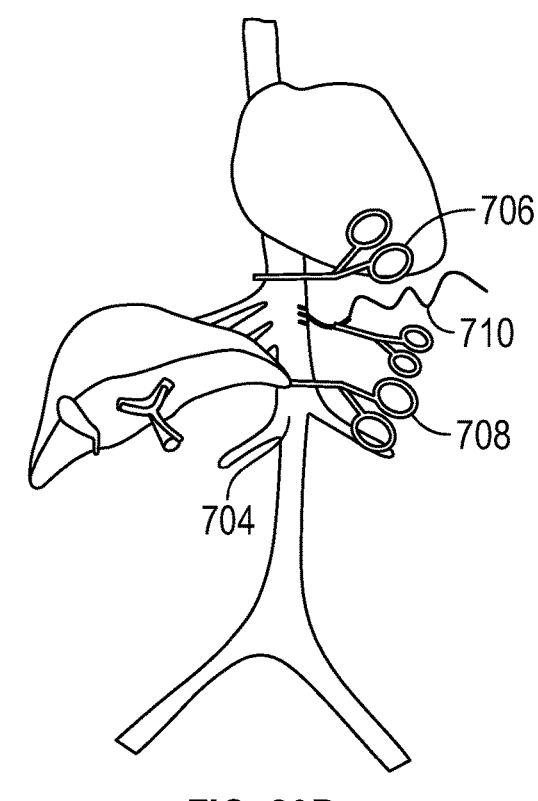
FIG. 20B
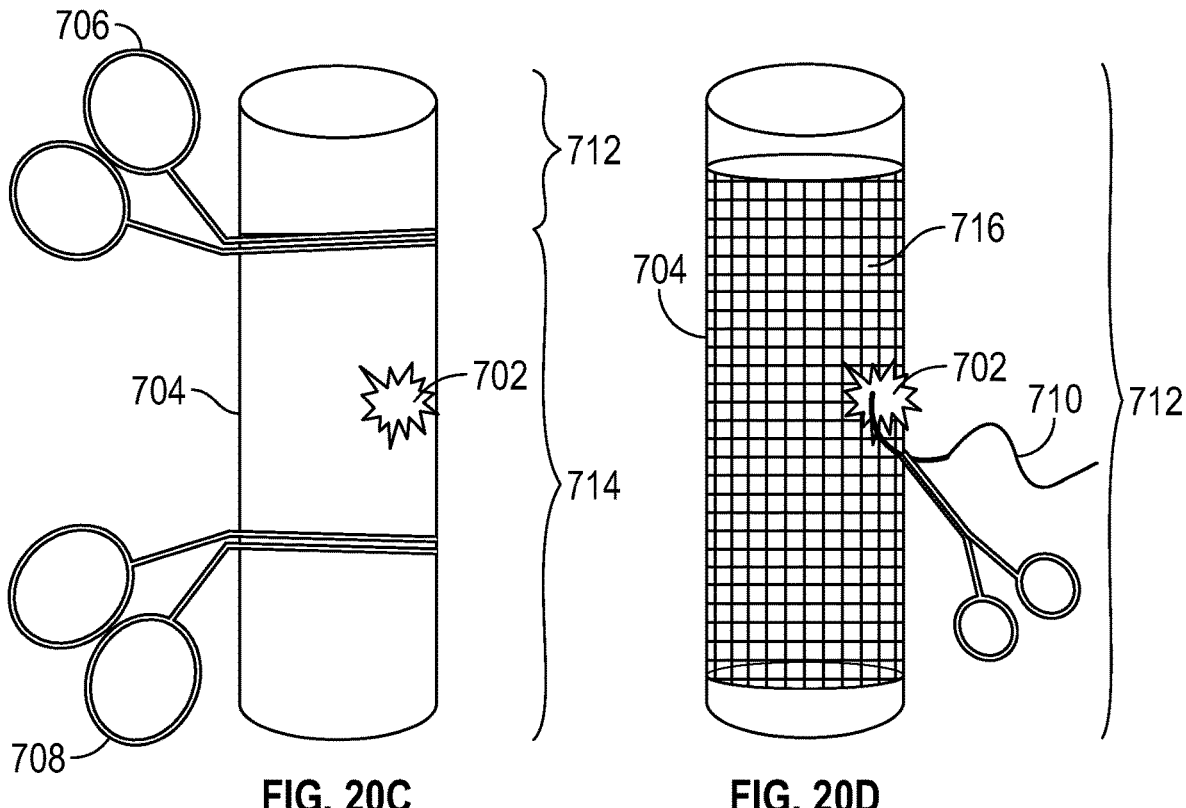
FIG. 20C                            FIG. 20D

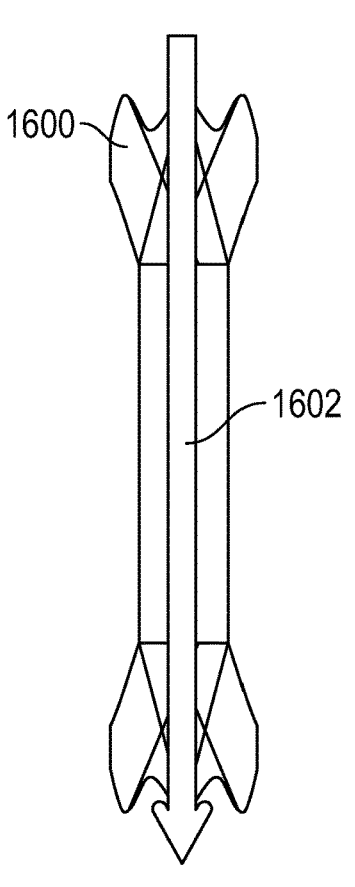
FIG. 41A
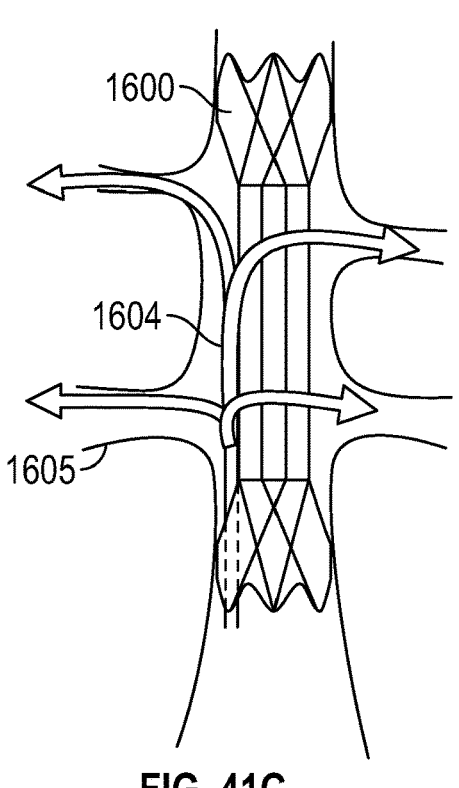
FIG. 41C
FIG. 41B
FIG. 41D

MULTI-LUMEN IMPLANTABLE DEVICE

CROSS REFERENCE TO RELATED APPLICATION

This application is the U.S. National Stage of International Application No. PCT/US2021/014661, filed Jan. 22, 2021, which was published in English under PCT Article 21 (2), which in turn claims the benefit of U.S. Provisional Application No. 62/970,023 filed Feb. 4, 2020, which is incorporated by reference herein in its entirety.

ACKNOWLEDGEMENT OF GOVERNMENT SUPPORT

This invention was made with government support under Grant No. EB022591 awarded by the National Institutes of Health. The government has certain rights in the invention.

FIELD

The present application concerns embodiments of a multi-lumen implantable device for delivering a therapeutic agent to a blood vessel of a patient.

BACKGROUND

In the U.S., over 120,000 patients are in need of an organ transplant. It has been reported that only about 28,000 people received organ transplants organs in 2012 in the U.S. As a result, an average of 18 patients will die each day awaiting an organ transplant. Furthermore, the economic burden of kidney dialysis while awaiting transplant is significant, costing nearly S40 billion dollars a year in the U.S. alone.

Organs recovered from living donors and those donated after brain death (DBD) (also referred to as "heartbeating donation" (HBD)) represent controlled situations where organs can be carefully exposed and cooled immediately at the time of recovery. This rapid cooling allows the highest preservation of function. Donation after cardiac death (DCD) (also referred to as "non-heartbeating donation" (NHBD)) represents a growing source of organs but presents unique challenges with regard to adequately preserving organ function just prior to transplant.

Organs (e.g., kidneys) from all donor types are susceptible to warm ischemia, which is caused by reduced blood flow or the cessation of blood flow to organs and can result in significant loss of organ function. DCD donors are particularly susceptible to rather long warm ischemia times compared to DBD donors because DCD donors can experience relatively long periods of low blood pressure that is inadequate for organ perfusion prior to actual cardiac death, such as after the DCD donor is removed from life support. Needless to say, maneuvers that expedite cardiac death are prohibited. Moreover, in order to ensure that brain damage after cardiac arrest is irreversible, transplant teams must wait a predetermined time period prior to commencing the procedure for removing an organ from the DCD donor. This time period typically is referred to as a "no-touch" time period and on average is at least five minutes from the time of pronounced cardiac death. Consequently, warm ischemia times of about 10-40 minutes have been documented for DCD donors. As a result of these delays, warm ischemia can result in significant loss of organ function.

Additionally, cardiovascular disease represents one of the most substantial causes of both death and disability worldwide. The delivery of potential therapies to blood vessels to treat cardiovascular disease can have several challenges. First, usually only a segment of vessel is in need of treatment, yet intravenous drugs are distributed throughout the entire body. The high volume of drug required for such treatments can result in increased costs and toxicity to the body (due to the drug being in the entire circulation). Another approach for drug delivery to a vessel for treatment includes utilizing a drug eluting stent or balloon, placed in the vessel. However, only a fraction of the drug may be delivered to the target vessel while the rest is lost to the circulation. In the case of drug eluting balloons, the exposure time to the drug is dependent on balloon inflation time, which, in turn, can lead to interval ischemia.

Accordingly, a need exists for delivering candidate therapeutic agents (e.g., drugs) to target vessels for the treatment of vascular disease (e.g., for aortic aneurysms, calcified vessels, or restenotic vessels), without the therapeutic agents being distributed to the entire circulation and without increased risk of distal ischemia during drug delivery.

SUMMARY

The present disclosure concerns embodiments of a multi-lumen (e.g., chamber) implantable device that can be used to deliver a therapeutic agent to a desired blood vessel in a patient without the therapeutic agent being distributed to undesired locations in the patient's circulation. In particular embodiments, the multi-lumen device comprises a radially expandable frame (e.g., stent) and is configured to deliver a therapeutic agent to a portion of a blood vessel in a patient while allowing blood to continue to flow through the blood vessel and blocking the therapeutic agent from being delivered to another portion of the blood vessel.

In one representative embodiment, an implantable device can include: a first lumen configured to flow blood from an upstream end to a downstream end of the device when implanted in a blood vessel; a second lumen fluidly separated from the first lumen and configured for introducing a therapeutic agent to a selected, first portion of a wall of the blood vessel, between the upstream end and the downstream end of the device; and at least one sealing member configured to block the therapeutic agent from entering a second portion of the wall of the blood vessel, between the upstream end and the downstream end of the device.

In some embodiments, the second lumen is arranged radially offset from the first lumen and adjacent to a central portion of the first lumen.

In some embodiments, the upstream end and downstream end of the device have a first diameter and are adapted to seal against the wall of the blood vessel and the upstream end and downstream end are spaced apart from one another, in an axial direction, by a central portion of the device.

In some embodiments, the second lumen is arranged in the central portion of the device and the first lumen is arranged in each of the upstream end, the central portion, and the downstream end of the device.

In some embodiments, a central portion of the first lumen arranged in the central portion of the device has a second diameter that is smaller than the first diameter.

In some embodiments, the second lumen is arranged radially outside of, relative to a central longitudinal axis of the device, and surrounds at least a portion of the first lumen.

In some embodiments, the first portion and the second portion of the wall of the blood vessel are arranged adjacent to one another and form an entirety of the wall of the blood vessel, between the upstream end and the downstream end of the device.

In some embodiments, the sealing member is configured to block one or more branch vessel openings in the second portion of the wall of the blood vessel.

In some embodiments, the implantable device comprises a radially expandable frame including an upstream annular portion arranged at the upstream end, a downstream annular portion arranged at the downstream end, and a central portion arranged between the upstream annular portion and the downstream annular portion, the central portion including at least one narrowed portion that indents radially inward from an outermost circumference of the frame.

In some embodiments, the at least one sealing member surrounds an exterior of the frame, the first lumen is formed within an interior of the frame, and the second lumen is formed between an outer surface of the at least one sealing member and the wall of the blood vessel, when the implantable device is radially expanded within the blood vessel.

In some embodiments, the frame comprises a plurality of longitudinally arranged struts, relative to a direction of a central longitudinal axis of the device, which are permanently connected to converging wires which converge into a shaft of a delivery apparatus which is configured to extend outside a body of a patient.

In some embodiments, the longitudinal orientation of the frame struts and convergence of the converging wires into the shaft of the delivery apparatus allows for collapse of the device after use by sheath advancement to remove the device.

In some embodiments, the implantable device comprises a radially expandable first frame and a radially expandable second frame, the second frame radially offset from and surrounding an entire circumference of the first frame and the at least one sealing member covers an outer surface of a selected portion of the second frame.

In some embodiments, the at least one sealing member is a first sealing member and the device further comprises a second sealing member surrounding an outer surface of the first frame. The first lumen is formed within an interior of the first frame by an inner surface of the second sealing member and the second lumen is formed in an annular space arranged between, in a radial direction, an outer surface of the second sealing member and the second frame.

In some embodiments, the frame comprises a plurality of longitudinally arranged struts, relative to a direction of a central longitudinal axis of the device, which converge at an end of the device into a single wire that is permanently affixed thereto.

In some embodiments, the longitudinal orientation of the frame struts and convergence into the single wire allows for collapse of the device after use by sheath advancement to remove the device.

In some embodiments, the at least one sealing member is a non-porous liner.

In some embodiments, the device further comprises an integrated nosecone and guidewire.

In some embodiments, the integrated nosecone and guidewire are arranged at a first end of the device and the device comprises a radially expandable frame comprising a plurality of longitudinally oriented struts that converge into a single delivery wire at an opposite, second end of the device.

In some embodiments, the device further comprises a perfusion lumen fluidly coupled to the second lumen and configured to extend outside a body of a patient.

In another representative embodiment, a method for delivering a therapeutic agent to a portion of a blood vessel via a multi-lumen implantable device can include: delivering the device, in a radially compressed state, to a target location in the blood vessel and radially expanding the device to seal a first end portion of the device against an upstream wall of the blood vessel and seal a second end portion of the device against a downstream wall of the blood vessel, wherein a central portion of the device is arranged between, in an axial direction relative to a central longitudinal axis of the device, the first end portion and the second end portion; flowing blood through a first lumen of the device, between the first end portion and the second end portion; delivering a therapeutic agent to a second lumen of the device while flowing blood through the first lumen, the second lumen fluidly separated from the first lumen and in fluid communication with a first portion of an inner wall of the blood vessel, between the upstream wall and the downstream wall; and blocking the therapeutic agent from reaching a second portion of the inner wall of the blood vessel via a sealing member of the device, the second portion of the inner wall radially offset from the first portion of the inner wall.

In some embodiments, the second lumen is formed between the first portion of the inner wall of blood vessel and the sealing member.

In some embodiments, the second lumen is formed between the first portion of the inner wall, the sealing member, and a second sealing member surrounding the first lumen and fluidly separating the first lumen and the second lumen.

In some embodiments, the method further comprises, after delivering the therapeutic agent to the second lumen, continuing to flow blood through the first lumen without flowing blood to the second lumen.

In some embodiments, delivering the therapeutic agent to the second lumen of the device includes delivering the therapeutic agent to the second lumen via a perfusion lumen of the device, the perfusion lumen extending from the second lumen to outside of a patient.

In some embodiments, the perfusion lumen is integrated with a remainder of the device.

In some embodiments, the method further comprises delivering the perfusion lumen over a wire, in a modular format, to dock into a fluidly sealed junction with the second lumen of the device, after radially expanding the device and prior delivering the therapeutic agent.

In some embodiments, the method further comprises following delivery of the therapeutic agent, removing the device from the blood vessel of a patient via advancing a sheath over an outside of the device in order to collapse the device into the radially collapsed state.

In some embodiments, the device comprises a frame comprising a plurality of longitudinally, relative to a central longitudinal axis of the device, oriented struts which converge into a delivery wire over which the sheath is adapted to slide.

In some embodiments, the longitudinal orientation of the frame struts and convergence distally into a delivery wire allows for collapse of the device after use by sheath advancement to remove the device.

In some embodiments, the therapeutic agent comprises one or more of an aneurysm promoting agent, an aneurysm stabilizing agent, an anti-calcification therapeutic agent, an antibiotic, an anti-neoplastic agent, an anti-restenotic agent, a vasoactive agent, and/or a gene therapy vector.

In some embodiments, the therapeutic agent is configured to simulate vascular pathogenesis, wherein the blood vessel is a blood vessel of an animal, and the delivering the therapeutic agent results in the creation of an animal model of vascular disease.

In another representative embodiment, a multi-lumen implantable device configured to be implanted in a blood vessel can include: a radially expandable frame covered with a non-porous liner, the radially expandable frame including a flared, first end portion, a flared, second end portion, and a central portion arranged between the first end portion and the second end portion, in an axial direction relative to a central longitudinal axis of the device, the central portion having a first indented portion that indents radially inward, toward the central longitudinal axis, from the first end portion and the second end portion, forming a cavity on an exterior of the covered frame, between the first end portion and the second end portion; a first lumen configured to flow blood from the first end portion, through the central portion, and to the second end portion, the first lumen formed by an inner surface of the non-porous liner; and a second lumen formed within the cavity, between an outer surface of the non-porous liner and a first portion of an inner wall of the blood vessel when the device is implanted in the blood vessel, wherein the second lumen is fluidly separated from the first lumen by the non-porous liner and is configured to deliver a therapeutic agent to the first portion of the inner wall of the blood vessel.

In some embodiments, the cavity is a first cavity and the device further comprises a third lumen formed within a second cavity formed by a second indented portion of the central portion which indents radially inward from the first end portion and the second portion, at a location that is radially offset from the first cavity. The third lumen is formed within the second cavity, between outer walls of the non-porous liner and the inner wall of the blood vessel when the device is implanted in the blood vessel.

In some embodiments, the device further comprises an additional radially expandable frame arranged within the first cavity and connected to the non-porous liner.

In some embodiments, the first cavity extends around only a portion of a circumference of the device, within the central portion of the device.

In some embodiments, a portion of the non-porous liner that covers a remaining portion of the central portion of the frame, not including the first indented portion, is configured to seal against a second portion of the inner wall of the blood vessel, the second portion radially offset from and arranged adjacent to the first portion of the inner wall of the blood vessel.

In yet another representative embodiment, a method for repair of an injured blood vessel or creating a vascular bypass via a multi-lumen implantable device can include: delivering the device, in a radially compressed state, to a target location in the blood vessel, the target location containing an injury or target location for a vascular bypass anastomosis, wherein the device comprises a radially expandable frame covered with a non-porous liner, the radially expandable frame including a flared, first end portion, a flared, second end portion, and a central portion arranged between the first end portion and the second end portion, in an axial direction relative to a central longitudinal axis of the device, the central portion having an indented portion that indents radially inward, toward the central longitudinal axis, from the first end portion and the second end portion, forming a cavity on an exterior of the covered frame, between the first end portion and the second end portion; radially expanding the device to seal the first end portion of the device against an upstream wall of the blood vessel and seal the second end portion of the device against a downstream wall of the blood vessel; flowing blood through a first lumen of the device, between the first end portion and the second end portion, the first lumen configured to flow blood through the central portion and formed by an inner surface of the non-porous liner; forming an outer, bloodless void in the blood vessel, between the first end portion and the second end portion and between a wall of the blood vessel and an outer surface of the non-porous liner covering the indented portion of the central portion of the frame; and repairing the blood vessel or creating the vascular bypass anastomosis in a region of the formed outer bloodless void.

In some embodiments, delivering the device to the target location in the blood vessel includes illuminating a light arranged on an exterior of a delivery sheath, wherein the device is contained within the delivery sheath in a radially compressed state during the delivering, and directing the delivery sheath to the target location via light transilluminated through the wall of the blood vessel.

In some embodiments, the method further comprises, after reaching the target location, axially sliding the delivery sheath to uncover the device and radially expanding the device at the target location.

The foregoing and other features and advantages of this disclosure will become more apparent from the following detailed description of several embodiments which proceeds with reference to the accompanying figures.

BRIEF DESCRIPTION OF THE DRAWINGS

FIGS. 20A and 20B illustrate the repair of a venous vascular injury using traditional clamps.

FIG. 20C illustrates the use of traditional arterial vascular clamps for vascular repair causing distal ischemia.

FIG. 20D illustrates a stent arranged across a vascular injury that allows blood flow past a vascular injury but suture repair of the injury may snag the scaffold of the underlying stent.

FIG. 41A is a schematic of a multi-lumen implantable device illustrating blood flow through a central, first lumen of the device.

FIG. 41B is a schematic of an angiogram of blood flow through the central, first lumen of the device of FIG. 41A.

FIG. 41C is a schematic of the device of FIG. 41A implanted in a blood vessel and illustrating a flow of a therapeutic agent through a second lumen of the device.

FIG. 41D is a schematic of an angiogram of the therapeutic agent flow through the second lumen of the device of FIG. 41C and into branching blood vessels.

DETAILED DESCRIPTION

The present disclosure concerns embodiments of an endovascular apparatus that can be used to perfuse the organs of a patient, such as an organ donor patient until the organs can be removed, thereby minimizing warm ischemia times. In particular embodiments, the endovascular apparatus is configured to isolate blood from the heart from flowing through the visceral arteries and veins while perfusing the organs within the abdomen with a separate perfusion liquid that helps preserve organ function until explant. As such, the endovascular apparatus is particularly suited for maintaining adequate perfusion of organs in DCD donors, in which there may not be adequate blood flow to the abdominal organs prior to cardiac arrest and during the so called "no-touch" time period following cardiac arrest.

The present disclosure also concerns embodiments of an endovascular apparatus, which can be a multi-lumen implantable device (e.g., multi-chamber stent), used to deliver a therapeutic agent (e.g., drug) to a blood vessel of a patient. In some embodiments, the multi-lumen implantable device can be configured to deliver the therapeutic agent to a portion of the blood vessel in which it is implanted while blocking the delivery of the therapeutic agent to another portion of the blood vessel and allowing blood to continue to flow through the blood vessel. As such, the multi-lumen implantable device can provide targeted drug delivery to a desired blood vessel in a patient without the therapeutic agent being delivered to the entire circulation of the patient. As such, therapies delivered via the multi-lumen implantable device may be more effective in treating vascular disease in the patient while also reducing systemic toxicity and overall treatment costs.

In some embodiments, the endovascular apparatus, which can be a covered (e.g., via a non-porous liner), radially expandable frame (e.g., stent) including flared end portions and a narrower central portion arranged therebetween, can be used during vascular surgery, in the place of vascular clamps. For example, such a device may provide a proximal and distal seal against a wall of a blood vessel in which it is implanted, allowing vascular surgery at location in a blood vessel that is arranged between the flared end portions without bleeding.

Figure 1:
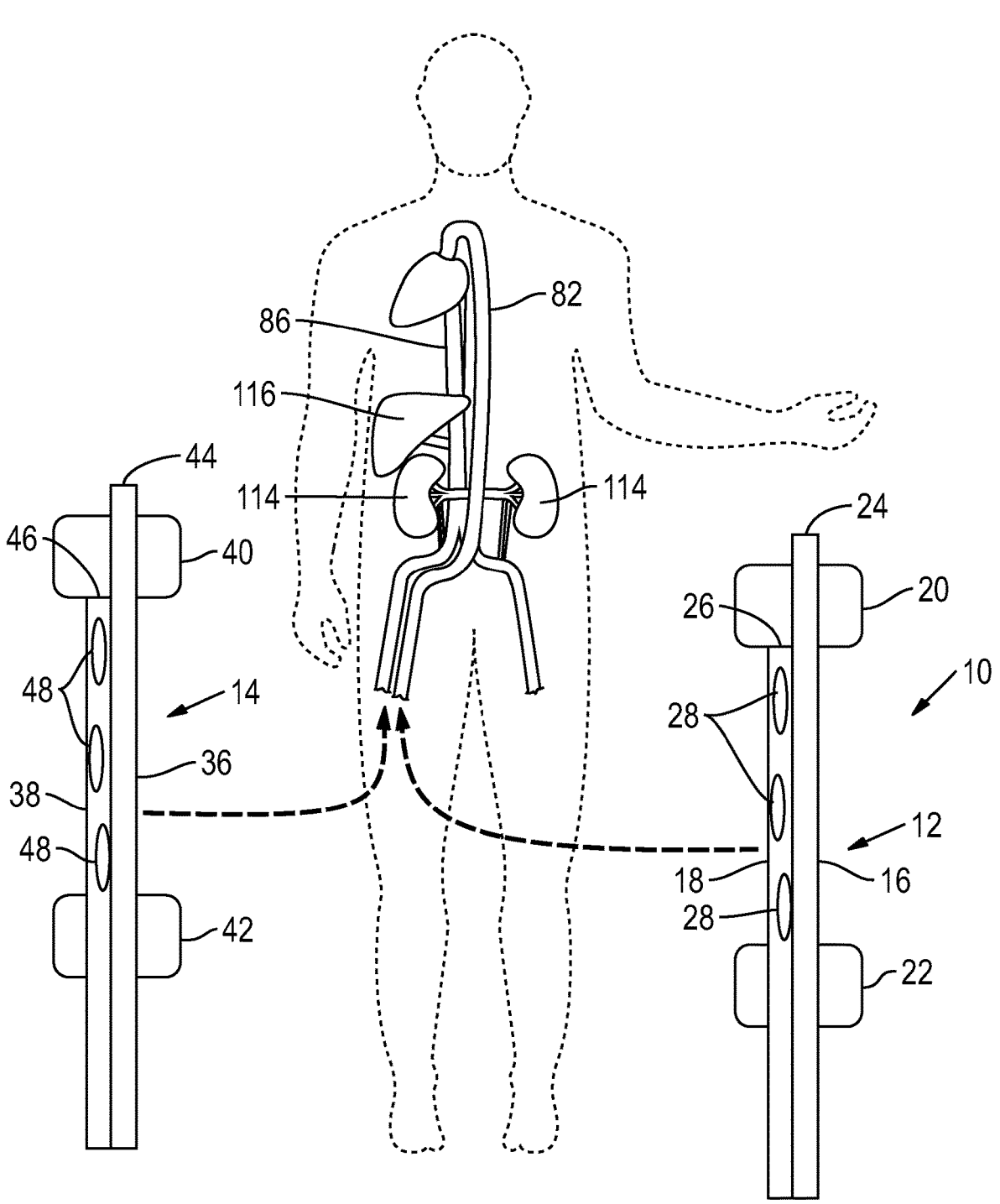
FIG. 1 illustrates an exemplary embodiment of an endovascular apparatus for perfusing organs of a patient.
Figures 2, 3, 4:
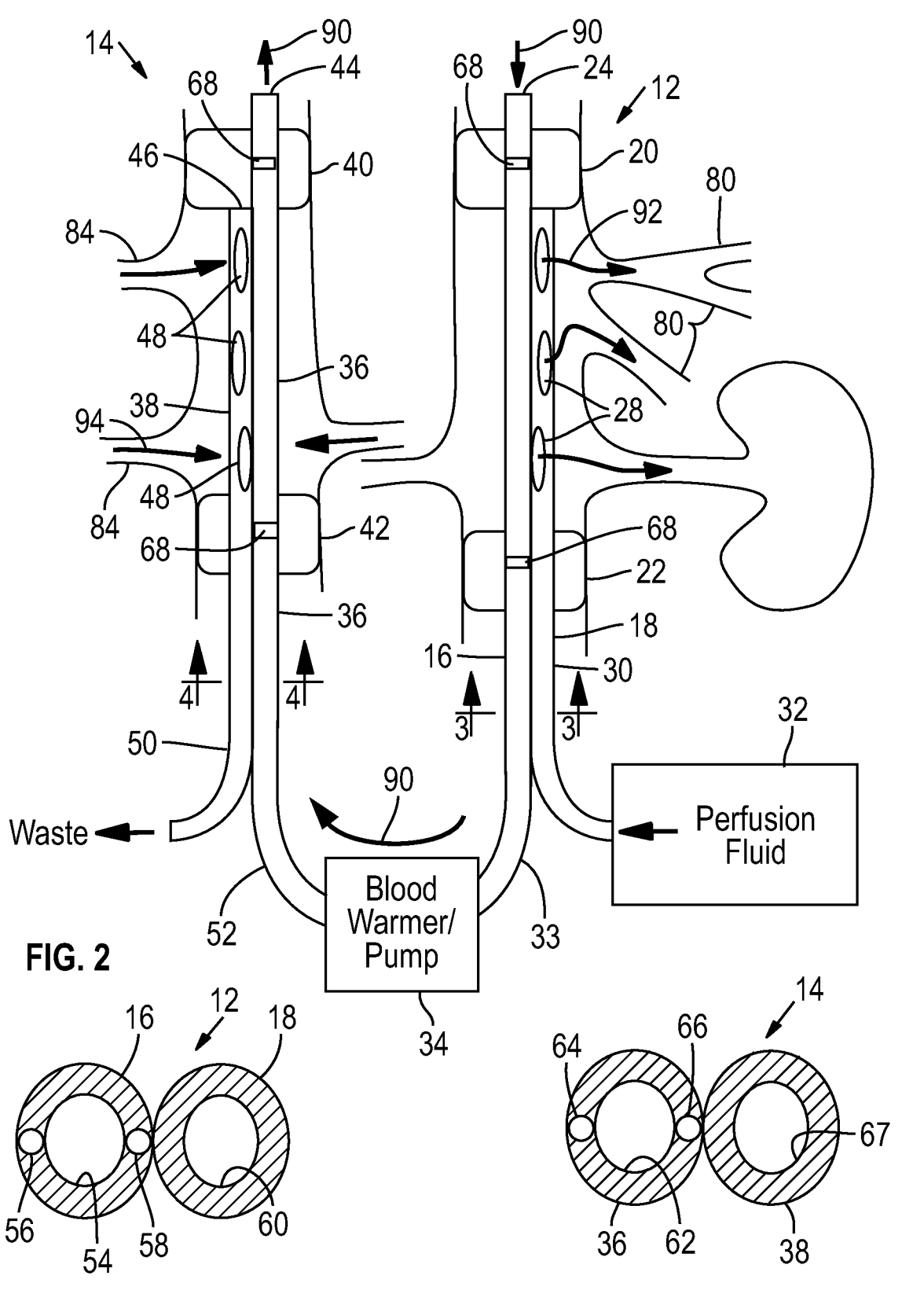
FIG. 2 is an enlarged view of the apparatus of FIG. 1, showing the apparatus deployed within the body of a patient.
FIG. 3 is a cross-section view of the apparatus of FIG. 2 taken along line 3-3 of FIG. 2.
FIG. 4 is a cross-section view of the apparatus of FIG. 2 taken along line 4-4 of FIG. 2.

Referring first to FIGS. 1 and 2, there is shown an endovascular apparatus 10 for isolating and perfusing the organs of a patient (e.g., an organ donor patient), according to one embodiment. The apparatus 10 may be configured for both arterial and venous access. For example, the apparatus 10 in the illustrated embodiment comprises a first, arterial catheter 12 and a second, venous catheter 14. The arterial catheter 12 is configured to isolate the visceral arteries 80 and divert blood from the aorta 82 to a location outside the body while the venous catheter 14 is configured to isolate the visceral veins 84 and introduce the blood back into the inferior vena cava 86 of the patient. The arterial catheter 12 also is configured to introduce a perfusion fluid (e.g., a cold perfusion solution) into the visceral arteries 80 for the purpose of perfusing donor organs (e.g., kidneys 114 or liver 116) in the abdominal cavity until such time the organs can be explanted. The venous catheter 14 also is configured to be placed into fluid communication with the visceral veins 84 in order to remove the perfusion fluid from the body.

The arterial catheter 12 in the illustrated embodiment comprises a first shaft 16 defining a first lumen 54 (FIG. 3) and a second shaft 18 defining a second lumen 60 (FIG. 3). Mounted on the shafts 16, 18 is a distal balloon 20 and a proximal balloon 22 spaced from the distal balloon 20. As shown in FIGS. 1 and 2, the first and second shafts 16, 18 extend through the proximal balloon 22. The first shaft 16 can extend through the distal balloon 20 and has a distal opening 24 that is in fluid communication with the aorta upstream of the distal balloon. The second shaft 18 can terminate at a location proximal to the distal balloon 20 and can have a closed end 26. The second shaft 18 also can have one or more side openings, or apertures, 28 along the length of the shaft between the distal and proximal balloons 20, 22, respectively. As best shown in FIG. 2, a proximal end portion 30 of the second shaft 18 can be fluidly connected to a source 32 of a perfusion fluid. A proximal end portion 33 of the first shaft 16 can be fluidly connected to an inlet port of a blood warmer 34.

The venous catheter 14 in the illustrated embodiment comprises a first shaft 36 defining a first lumen 62 (FIG. 4) and a second shaft 38 defining a second lumen 67 (FIG. 4). Mounted on the shafts 36, 38 is a distal balloon 40 and a proximal balloon 42 spaced from the distal balloon 40. As shown in FIGS. 1 and 2, the first and second shafts 36, 38 extend through the proximal balloon 42. The first shaft 36 can extend through the distal balloon 40 and has a distal opening 44 that is in fluid communication with the inferior vena cava downstream of the distal balloon. The second shaft 38 can terminate at a location proximal to the distal balloon 40 and can have a closed end 46. The second shaft 38 also can have one or more side openings, or apertures, 48 along the length of the shaft between the distal and proximal balloons 40, 42, respectively. As best shown in FIG. 2, a proximal end portion 50 of the second shaft 38 can extend outside the body for draining perfusion fluid away from the body. A proximal end portion 52 of the first shaft 36 can be fluidly connected to an outlet port of the blood warmer 34.

As shown in FIG. 3, the first shaft 16 of the arterial catheter 12 can have a first lumen 54 for diverting blood from the aorta to the blood warmer 34 and second and third lumens, 56, 58, respectively, for introducing an inflation fluid to the distal and proximal balloons 20, 22, respectively. The second lumen 56 can have a distal end in fluid communication with the inside of the distal balloon 20 and a proximal end in fluid communication with a source of an inflation fluid (not shown). The third lumen 58 can have a distal end in fluid communication with the inside of the proximal balloon 22 and a proximal end in fluid communication with the source of the inflation fluid. Thus, in use, an inflation fluid (e.g., saline) can be introduced under pressure into the balloons to inflate the balloons and cause them to engage and form a seal with the inner wall of the aorta. The second shaft 18 can have a lumen 60 that allows a perfusion fluid from the source 32 to be introduced into the visceral arteries 80. In an alternative embodiment, the inflation lumens 56, 58 can be provided in the second shaft 18 rather than in the first shaft 16. In another embodiment, one of the inflation lumens can be provided in the first shaft 16 and the other inflation lumen can be provided in the second shaft 18.

As shown in FIG. 4, the first shaft 36 of the venous catheter 14 can have a first lumen 62 for introducing blood from the blood warmer 34 back into the body and second and third lumens, 64, 66, respectively, for introducing an inflation fluid to the distal and proximal balloons 40, 42, respectively. The second lumen 64 can have a distal end in fluid communication with the inside of the distal balloon 40 and a proximal end in fluid communication with the inflation fluid source. The third lumen 66 can have a distal end in fluid communication with the inside of the proximal balloon 42 and a proximal end in fluid communication with the inflation fluid source. Thus, in use, an inflation fluid (e.g., saline) can be introduced under pressure into the balloons 40, 42 to inflate the balloons and cause them to engage and form a seal with the inner wall of the inferior vena cava. The second shaft 38 can have a second lumen 67 that allows the perfusion fluid returning from the visceral veins 84 to flow outside the body, where it can be collected and disposed of as waste. In an alternative embodiment, the inflation lumens 64, 66 can be provided in the second shaft 38 rather than in the first shaft 36. In another embodiment, one of the inflation lumens can be provided in the first shaft 36 and the other inflation lumen can be provided in the second shaft 38.

Each of the catheters 12, 14 can include suitable positioning markers and/or sensors at convenient locations to assist in locating the balloons of each catheter at the desired locations within the aorta and the inferior vena cava. In the illustrated embodiment, for example, the first shaft 16 of the arterial catheter 12 includes a pair of radiopaque markers 68 aligned with the distal and proximal balloons 20, 22, respectively. Similarly, the first shaft 36 of the venous catheter 14 includes a pair of radiopaque markers 68 aligned with the distal and proximal balloons 40, 42, respectively. In alternative embodiments, the markers 68 can be provided on the second shafts 18, 38 or on both the first and second shafts of each catheter 12, 14. Also, although the illustrated embodiment includes a pair of markers 68 for each catheter, a greater or fewer number of markers can be provided for each catheter 12, 14.

In alternative embodiments, the positioning markers can comprise passive or active emitters that can emit electromagnetic waves through the body and a corresponding detector or monitor can be used to receive the electromagnetic waves from the emitters and provide visual and/or audible feedback to a user indicating the position of the markers inside the body relative to external landmarks on the body. In particular embodiments, for example, the positioning markers can be emitters that can emit radiofrequency waves, such as radiofrequency identification (RFID) and magnetic sensor tags. Further details of the use of RFID tags as positioning marks are disclosed in Application No. 61/845,896, filed Jul. 12, 2013, and PCT/US2014/046224, filed Jul. 10, 2014, which are incorporated herein by reference.

In use, as depicted in FIG. 1, the first arterial catheter 12 can be inserted into the aorta via an incision in a femoral artery in a minimally invasive manner using known techniques. Similarly, the second venous catheter 14 can be inserted into the inferior vena cava via an incision in a femoral vein in a minimally invasive manner Guidewires, dilators and/or introducers can be used to help introduce and advance the catheters through the patient's vasculature, as known in the art. As best shown in FIG. 2, the arterial catheter 12 is positioned such that the distal balloon 20 is upstream of the visceral arteries 80 and the proximal balloon 22 is downstream of the visceral arteries 80. Similarly, the venous catheter 14 is positioned such that the distal balloon 40 is downstream of the visceral veins 84 and the proximal balloon 42 is upstream of the visceral veins 84. The proper positioning of the catheter 12, 14 can be accomplished by viewing the markers 68 under fluoroscopy.

Once the catheters are in place, each pair of balloons can be inflated against the inner walls of the aorta and inferior vena cava, thereby isolating the visceral arteries and veins. This causes oxygenated blood from the heart to flow through the first shaft 16 of the arterial catheter, through the blood warmer, through the first shaft 36 of the venous catheter and into the inferior vena cava where blood can flow back into the right atrium of the heart, as indicated by arrows 90. At the same time, a cold perfusion fluid from source 32 is introduced into the visceral arteries 80 via the side openings 28 in the second shaft 18 of the arterial catheter, as indicated by arrows 92. The perfusion fluid can flow through the abdominal organs, the visceral veins 84 and into the isolated region of the inferior vena cava, where it can then flow inwardly through the side openings 48 of the second shaft 38, as indicated by arrows 94. The perfusion fluid can then be removed from the body via the second shaft 38 for proper disposal.

In particular embodiments, the perfusion fluid can be similar to the University of Wisconsin solution and can comprise, without limitation, one or more of the following compounds: heparin, pentastarch, steroids, lactobionic acid, magnesium sulfate, raffinose, adenosine, allopurinol, glutathione, and potassium hydroxide. The perfusion fluid can be cooled to a temperature of about 0 degree C. to about 10 degrees C. for introduction into the body and more preferably to a temperature of about 4 degrees C. to about 6 degrees C. As an alternative perfusion fluid, blood separate from the circuit of blood being circulated by the heart can be propelled, oxygenated and warmed before being cycled continuously through the catheters, as further described below.

As noted above, the apparatus is particularly suited for use with DCD donors. In this regard, the catheters 12, 14 can be inserted and deployed (i.e., the balloons inflated to isolate the visceral arteries and veins) in the vasculature of a DCD donor as soon as possible prior to cardiac death. For example, the catheters 12, 14 can be inserted and deployed in a DCD donor just prior to or at the same time as removing the patient from life support or when the donor is experiencing unstable vital signs for normal organ blood flow. The blood flow circuit allows for normal blood flow through the body, except for those isolated regions, while awaiting expected cardiac death and during the predetermined waiting period before explant can occur. In another implementation, the catheters 12, 14 can be inserted into the DCD donor prior to cardiac death and then are deployed at the time of cardiac death. In yet another implementation, the apparatus can be inserted and deployed in a donor who expires prematurely before a donor team is ready to perform the explant procedure. In any case, during the period of time before explant can be performed, the perfusion fluid reduces warm ischemia time and preserves organ function.

In another embodiment, the catheters 12, 14 can be inserted into the aorta and the vena cava of a donor (e.g., a DCD donor) but not deployed (i.e., the balloons are not inflated) until after cardiac death or until after the predetermined waiting period. This allows for normal blood flow throughout the body until the balloons are deployed. At the prescribed time (e.g., after confirmed cardiac death), the balloons can be rapidly deployed to isolate the visceral arteries and veins and a perfusion fluid (e.g., a cold solution or blood) can be circulated through the isolated regions until explant.

In the embodiment of FIGS. 1 and 2, the catheters 12, 14 also isolate the lower extremities from the flow of blood. It has been found that humans can tolerate lower extremity ischemia for several hours. If desired, however, the apparatus 10 can be adapted to permit blood from the heart to circulate through the lower extremities.

Figure 5:
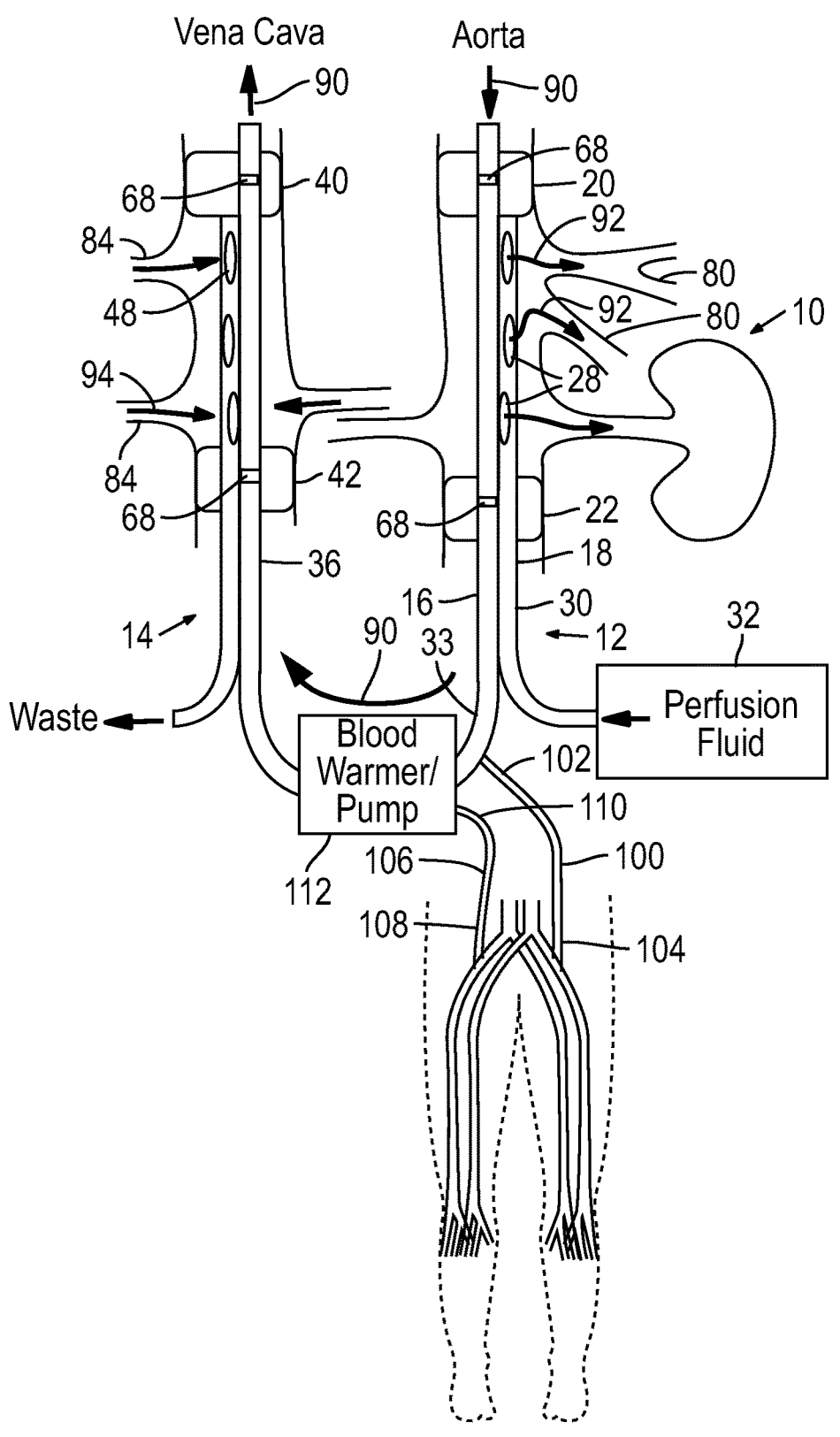
FIG. 5 illustrates another exemplary embodiment of an endovascular apparatus for perfusing organs of a patient.

For example, FIG. 5 shows the apparatus 10 of FIGS. 1 and 2 with additional components to permit blood from the heart to circulate through the lower extremities. In the embodiment of FIG. 5, the apparatus 10 further includes an arterial extension portion or conduit 100 that has a first end portion 102 that is in fluid communication with the proximal end portion 33 of the first shaft 16 of the arterial catheter 12. A second end portion 104 of the extension portion 100 can be inserted into a femoral artery, which can be the same femoral artery through which the arterial catheter 12 has been inserted or the other femoral artery. If the extension portion 100 is inserted into the same femoral artery as the arterial catheter 12, the extension portion 100 would be inserted downstream of the insertion point of the arterial catheter 12. The conduit 100 diverts a portion of blood from shaft 16 to flow into the vasculature of the lower extremities.

In the embodiment of FIG. 5, the apparatus 10 also includes a lower extremity return line or conduit 106 having a first end portion 108 inserted into a femoral vein, which can be the same femoral vein through which the venous catheter 14 has been inserted or the other femoral vein. If the return conduit 106 is inserted into the same femoral vein as the venous catheter 14, the return line would be inserted upstream of the insertion point of the venous catheter 14. A second end portion 110 of the return conduit 106 is in fluid communication with an inlet port of a blood pump 112. As shown in FIG. 5, the proximal end portion 33 of shaft 16 is also in fluid communication with a respective inlet port of the blood pump 112. In this manner, the blood flowing through the vasculature of the lower extremities is returned to pump 112 via the return conduit 106.

The blood pump 112 is configured to allow higher pressure blood from shaft 16 and lower pressure blood from return conduit 106 to mix and equalize before it is pumped under pressure into shaft 36 of the venous catheter 14. For example, the blood pump can have an internal storage chamber that receives blood from the return conduit 106 and shaft 16 at static pressure. Blood from the storage chamber can then be pumped under pressure into shaft 36. In this manner, blood from the heart can be diverted to flow through the lower extremities and back into the vena cava. Blood from shaft 16 and return conduit 106 can also flow through a blood warmer, which can be an integral or separate component from the blood pump 112.

Figures 6, 7, 8:
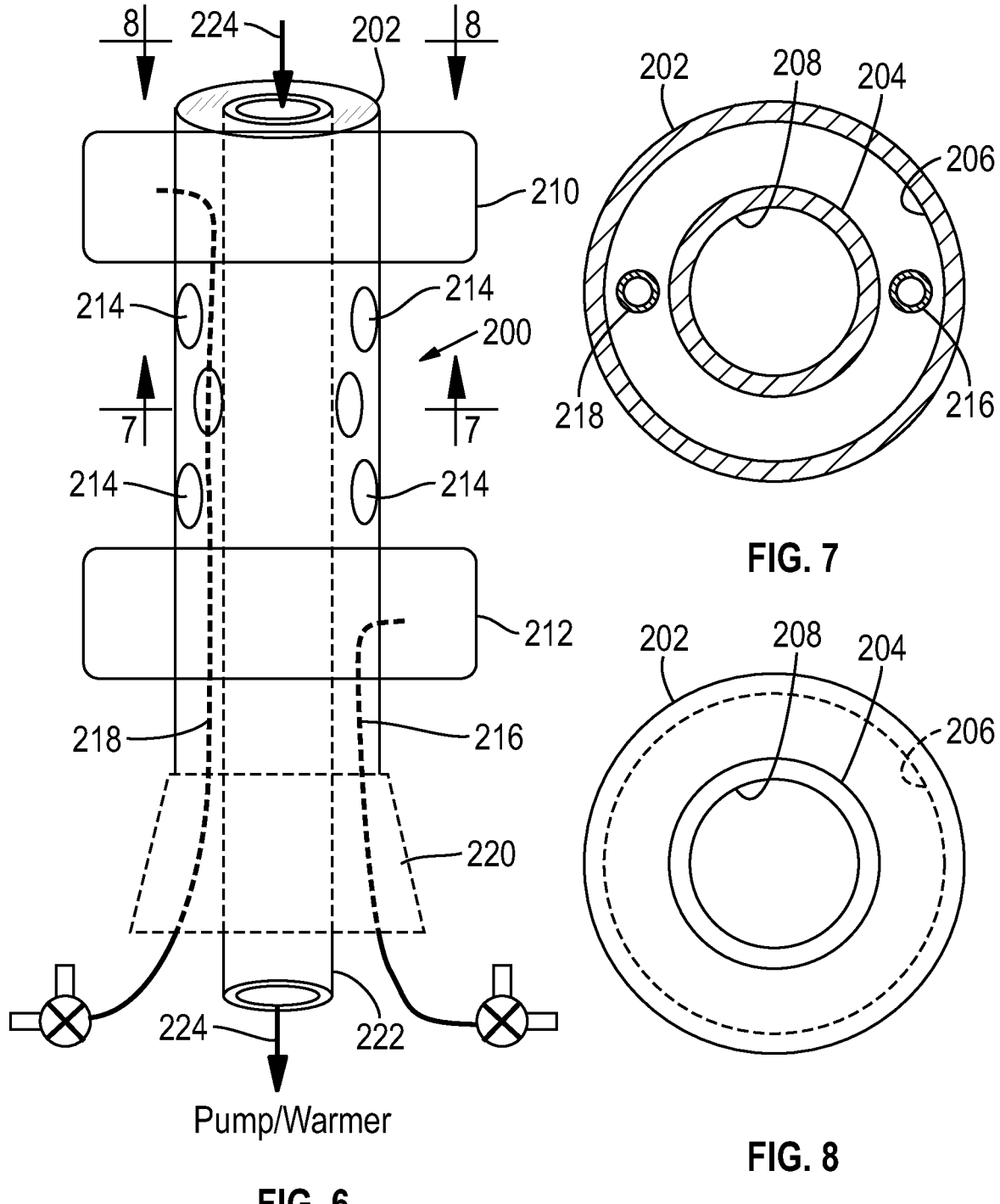
FIG. 6 is a side view of an arterial catheter of an endovascular apparatus, according to another embodiment.
FIG. 7 is a cross-section view of the apparatus of FIG. 6 taken along line 7-7 of FIG. 6.
FIG. 8 is a cross-section view of the apparatus of FIG. 6 taken along line 8-8 of FIG. 6.

FIG. 6 shows an arterial catheter 200 for an endovascular apparatus, according to another embodiment. The arterial catheter 200 performs the same function as the arterial catheter 12 of FIGS. 1 and 2 but has a different construction. The arterial catheter 200 comprises an outer shaft 202, an inner shaft 204 spaced radially inwardly from the outer shaft 202, an annular lumen 206 defined between shafts 202, 204, and an inner lumen 208 defined by the inner shaft 204. Mounted on the outer shaft 202 are two spaced apart inflatable balloons 210, 212. A plurality of side openings or apertures 214 are formed along the length of the outer shaft 202 between the balloons 210, 212. First and second inflation conduits 216, 218, respectively, extend through the annular lumen 206. The first inflation conduit 216 has a distal end that is fluid communication with the proximal balloon 212 and a proximal end that is in fluid communication with a source of an inflation fluid. The second inflation conduit 218 has a distal end that is fluid communication with the distal balloon 210 and a proximal end that is in fluid communication with the inflation fluid source.

The proximal end of the outer shaft 202 can terminate at a proximal hub 220 that extends outside the body and is fluidly connectable to a source of a perfusion fluid. The inner shaft 204 has a proximal end portion 222 that extends outside the body and is fluidly connectable to a blood warmer and/or pump (not shown in FIG. 6). The annular lumen 206 is closed at the distal end of the outer shaft 202.

The arterial catheter 200 can be inserted and deployed within a patient's aorta in the same manner described above in connection with the arterial catheter 12. A venous catheter (not shown) having the same construction as the arterial catheter 200 can be inserted into the vena cava in the same manner described above in connection with the venous catheter 14. In use, the inner shaft of the venous catheter is fluidly connected to the outlet of the blood pump/warmer and the outer shaft of the venous catheter can be fluidly connected to a drain outside the body. Upon deployment of the arterial catheter 200 and the similarly constructed venous catheter, the visceral arteries and veins are isolated and blood from the heart flows proximally through the inner lumen 208 and exits the body where it can be routed through the blood pump/warmer, as indicated by arrows 224. Blood from the blood pump/warmer can be returned to the vena cava via the inner lumen of the venous catheter where returning blood can flow back to the heart. The abdominal organs can be perfused by introducing a pressurized perfusion fluid into the annular lumen 206 of the catheter 200, which then flows outwardly through side openings 214 into the visceral arteries. The perfusion fluid can then flow through the abdominal organs, the visceral veins, and back into and through the annular lumen of the venous catheter via side openings in the venous catheter.

Figure 9:
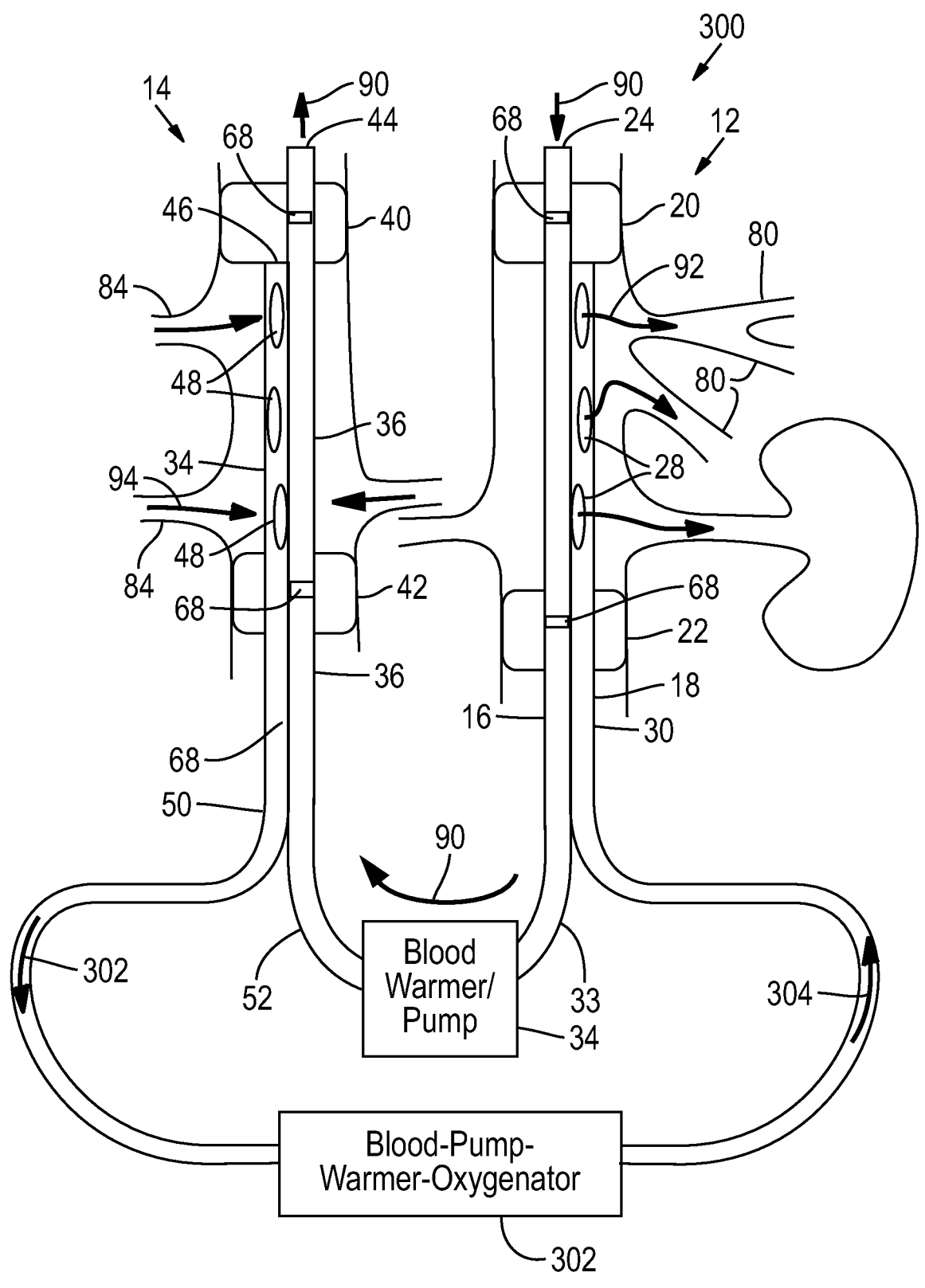
FIG. 9 illustrates another exemplary embodiment of an endovascular apparatus for perfusing organs of a patient.

FIG. 9 shows an endovascular apparatus 300, according to another embodiment. The apparatus 300 is similar in many respects to the apparatus 10 of FIGS. 1 and 2. Thus, components in FIG. 9 that are the same as components in FIGS. 1 and 2 are given the same respective reference numbers and are not described further.

In the embodiment of FIG. 9, the isolated regions of the patient's vasculature can be perfused with the patient's own blood rather than a cold perfusion solution. The apparatus 300 comprises a cardiopulmonary bypass machine 302 or equivalent device that can warm, oxygenate and pressurize blood. The machine 302 has an inlet port fluidly connected to the second shaft 38 of the venous catheter 14 and an outlet port fluidly connected to the second shaft 18 of the arterial catheter. In use, blood can be drawn from the patient and introduced into a blood flow circuit that is fluidly separated from the blood being circulated by the heart. The blood being used as the perfusion fluid is circulated outwardly from the body via the second shaft 38 of the venous catheter 14, and through the cardiopulmonary bypass machine 302, which can oxygenate and warm the blood, and pump the blood back into the body via the second shaft 18 of the arterial catheter 12, in the direction indicated by arrows 304. Maintaining blood circulation through the isolated regions that is fluidly separated from the circulation of blood through the patient's heart allows for adequate perfusion of the organs while awaiting cardiac death.

The embodiments disclosed herein can be used for procedures other than procedures for preserving organ function for explant surgery. For example, in another implementation, an endovascular apparatus (e.g., an apparatus of FIG. 1, 5 or 6) can be used to perfuse organs during survival surgery, such as cardiac or proximal aortic repairs where prolonged cessation of blood flow poses a risk of organ damage.

Figure 10:
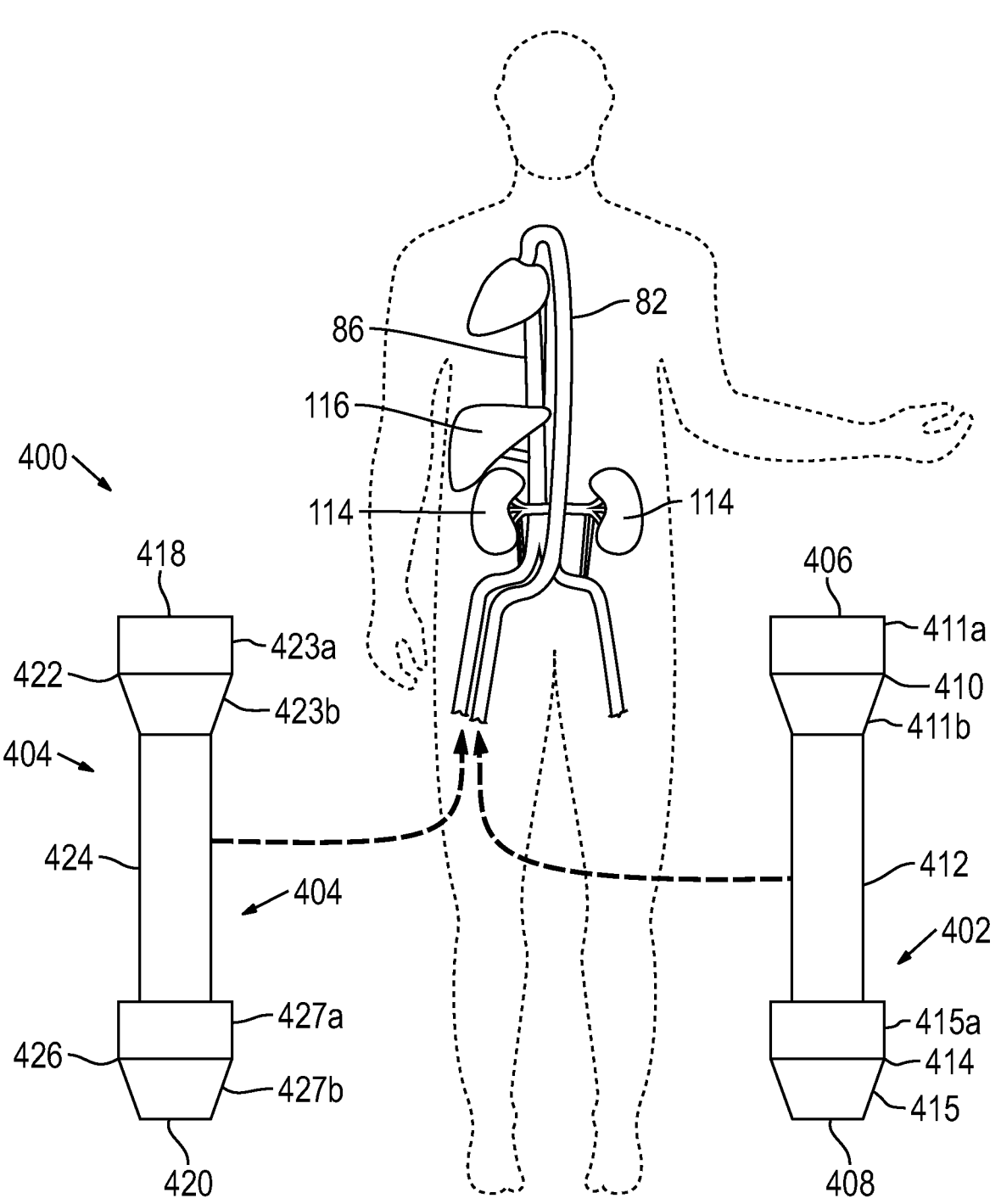
FIG. 10 illustrates an endovascular apparatus for perfusing organs of a patient, according to another embodiment.
Figure 11:
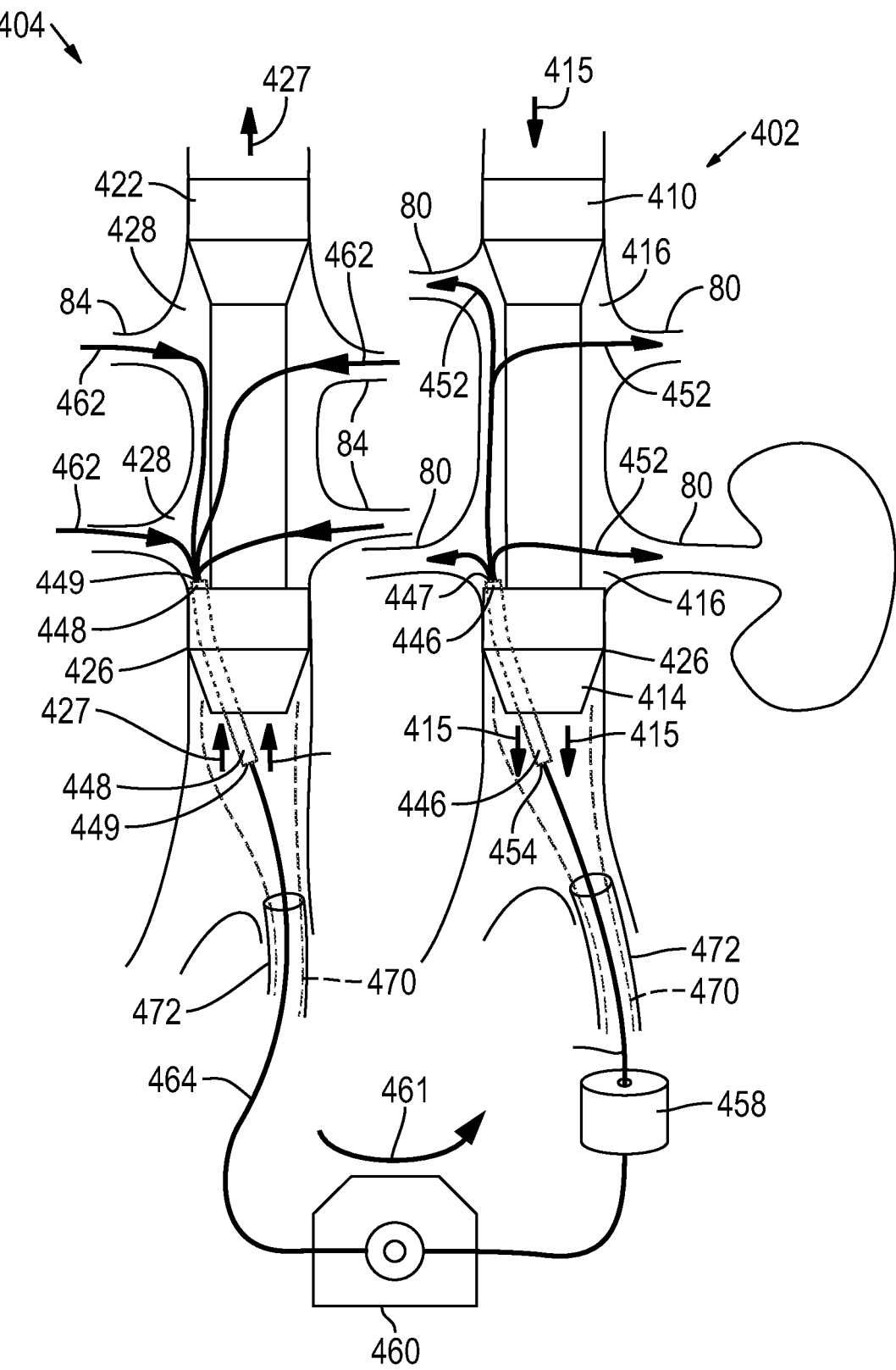
FIG. 11 is an enlarged view of the apparatus of FIG. 10, showing the apparatus deployed within the body of a patient.

Referring to FIGS. 10 and 11, there is shown another embodiment of an endovascular apparatus that can be used for isolating and perfusing the organs of a patient (e.g., an organ donor patient), indicated generally at 400. The apparatus 400 in the illustrated embodiment comprises an arterial perfusion stent (e.g., stent graft) 402 and a venous perfusion stent (e.g., stent graft) 404. The arterial perfusion stent 402 is configured to isolate blood flow to the visceral arteries 80, while allowing blood from the aorta 82 to continue to flow to the lower extremities. The venous perfusion stent 404 is configured to isolate blood flow from the visceral veins 84, while allowing blood from the lower extremities to continue to flow to the heart via the inferior vena cava 86 of the patient. Thus, when deployed in a patient, the endovascular apparatus allows blood from the heart to pass uninterrupted through a central lumen of the arterial perfusion stent 402 to perfuse the lower body and then flow through a central lumen of the venous perfusion stent 404 to return to the heart. Converging wires 470 are permanently affixed to the distal end of the stent and allows for recapture of the stent by sheath advancement after use for removal from the body.

Additionally, the arterial perfusion stent 402 of endovascular apparatus 400 is configured to introduce a perfusion fluid (e.g., a cold perfusion solution, or re-oxygenated and/or warmed blood) into the visceral arteries 80 for the purpose of perfusing donor organs (e.g., kidneys 114 or liver 116) in the abdominal cavity until such time the organs can be explanted. The venous perfusion stent 404 is configured to receive the perfusion fluid from the visceral veins 84 that was introduced into the body from the arterial perfusion stent 402. As discussed in more detail below, the arterial and venous perfusion stents 402, 404 can each comprise a perfusion lumen (such as defined by an arterial perfusion conduit or sleeve 446 and a venous perfusion conduit or sleeve 448, see FIG. 11) that facilitates perfusion of blood or fluid through the abdominal organs, while allowing normal blood flow between the heart and lower extremities. Additionally, the arterial and venous perfusion stents 402, 404 include a non-porous liner 466 (best shown in FIG. 13) that prevents or substantially reduces mixing of blood or other fluids flowing through the aorta or inferior vena cava and the visceral arteries and veins.

Figures 13, 14, 15, 16:
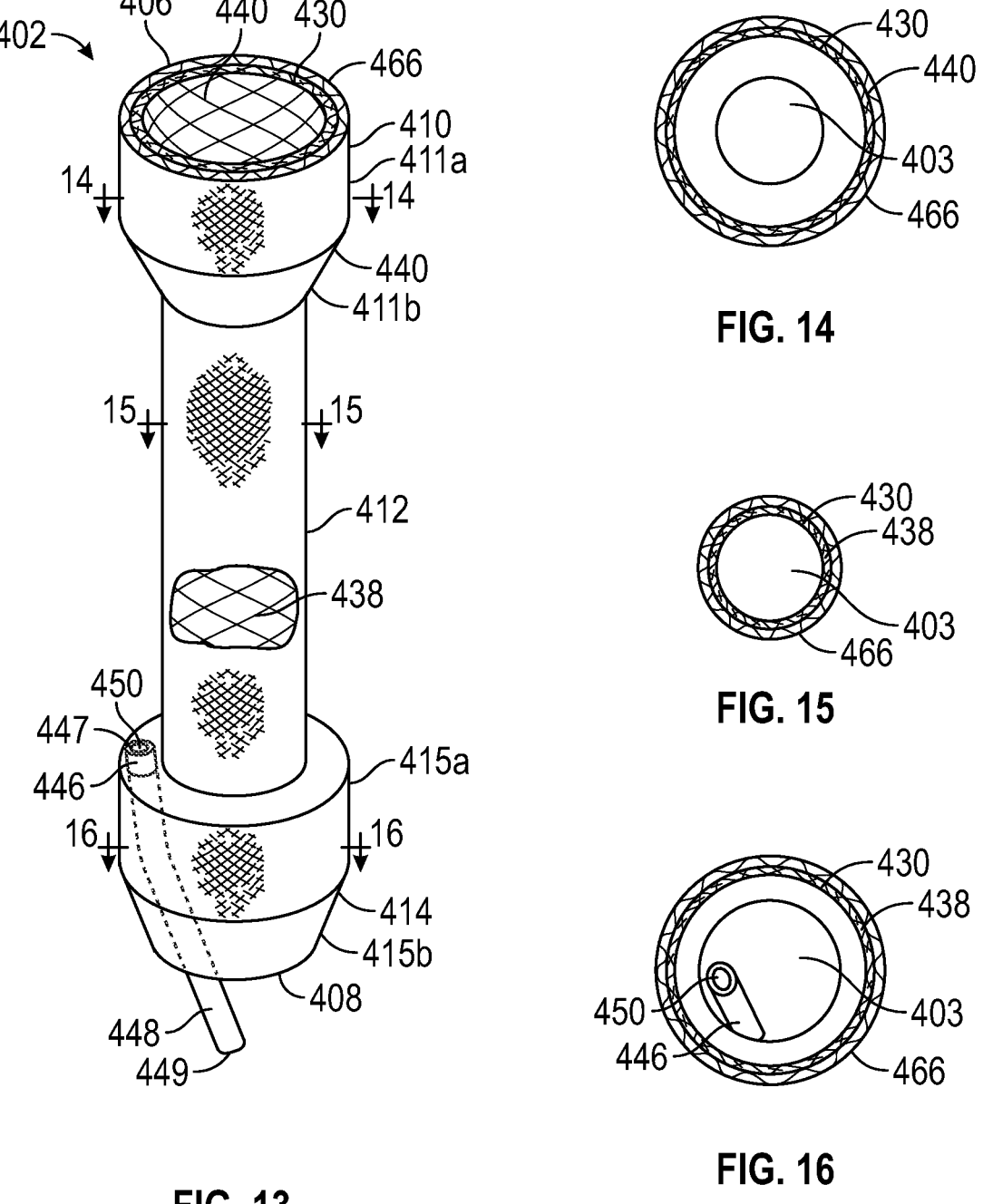
FIG. 13 is a side view of a perfusion stent, according to one embodiment.
FIG. 14 is a cross-section view of the perfusion stent of FIG. 13 taken along line 14-14 of FIG. 13.
FIG. 15 is a cross-section view of the perfusion stent of FIG. 13 taken along line 15-15 of FIG. 13.
FIG. 16 is a cross-section view of the perfusion stent of FIG. 13 taken along line 16-16 of FIG. 13.

The arterial perfusion stent 402 comprises an elongated body that includes a radially compressible and expandable annular frame 430 supporting the liner 466. In FIG. 13 the frame 430 comprise a metal mesh, although the frame can have other configurations in other embodiments. Referring to FIGS. 13-16, in the illustrated embodiment, the stent 402 defines a central lumen 403 that extends from a proximal end 408 to a distal end 406 of the perfusion stent. The central lumen 403 allows passage of fluid (e.g., blood) through the body of the perfusion stent, thus maintaining blood flow through the artery in which the perfusion stent is deployed. The perfusion stent 402 can be radially compressible to a compressed state for delivery through the body to a deployment site and expandable to its functional size shown in FIG. 11 at the deployment site. In certain embodiments, the perfusion stent 402 is self-expanding; that is, the stent can radially expand to its functional size when advanced from the distal end of a delivery sheath. Apparatuses particularly suited for percutaneous delivery and implantation of a self-expanding stent in the vessels of the body are well known and described briefly below. In other embodiments, the perfusion stent can be a plastically-expandable perfusion stent that can be adapted to be mounted in a compressed state on the balloon of a delivery catheter or another type of expansion device configured to expand the stent radially from a compressed delivery state to a radially expanded state. The perfusion stent can be expanded to its functional size at a deployment site by inflating the balloon of a balloon catheter, as known in the art.

The elongated body of the arterial perfusion stent 402 comprises a distal end portion 410, a generally cylindrical intermediate portion 412, and a proximal end portion 414. The distal end portion 410 can comprise a generally cylindrical first section 411*a* and a tapered second section 411*b* positioned proximal to the first section 411*a*. Likewise, the proximal end portion 414 can comprise a generally cylindrical first section 415*a* and a tapered second section 415*b* proximal to the first section 415*a*. In the radially expanded state of the perfusion stent, the distal and proximal end portions 410, 414 have an outer diameter that is larger than the outer diameter of the intermediate portion 412, thereby defining an annular perfusion space 416 (best shown in FIG. 11) between the end portions and around the intermediate portion. Central lumen 403 extends through body of the arterial perfusion stent, allowing flow of fluid (e.g., blood) through from the distal end 406 to the proximal end 408 of the arterial perfusion stent, in the direction of arrows 415 shown in FIG. 11. The stent is deployed by withdrawal of the sheath of the delivery apparatus which allows expansion of the shape memory frame as it leaves the sheath.

The outer surfaces of the distal and proximal end portions 410, 414 form a seal against the inner wall of the aorta when the arterial perfusion stent is in the radially expanded state. Thus, the outer surface of the distal and proximal end portions 410, 414 of the stent in the radially expanded state can have a diameter that is about the diameter of the inner surface in the region of the aorta where the stent will be placed. For example, for a perfusion stent to be placed in an adult, the outer surface of the distal and proximal end portions 410, 414 of the stent in the radially expanded state can have a diameter ranging from 12 mm to 3 cm. Smaller stents can be used in pediatric patients.

The venous perfusion stent 404 can have the same construction as the arterial perfusion stent 402. Thus, in the illustrated embodiments, the venous perfusion stent 404 has a distal end 418 and a proximal end 420. The stent 404 can comprise a distal end portion 422, a generally cylindrical intermediate portion 424, and a proximal end portion 426. The distal end portion 422 can comprise a generally cylindrical first section 423*a* and a tapered section 423*b* positioned proximal to the first section 423*a*. Likewise, the proximal end portion can comprise a generally cylindrical first section 427*a* and a tapered second section 472*b* positioned proximal to the first section 427*a*. In the radially expanded state of the venous perfusion stent, the distal and proximal end portions 422, 426 have an outer diameter that is larger than the outer diameter of the intermediate portion 424, thereby defining an annular perfusion space 428 (best shown in FIG. 11) between the end portions and around the intermediate portion. A central lumen extends through body of the venous perfusion stent, allowing flow of fluid (e.g., blood) through from the proximal to distal end of the venous perfusion stent, in the direction of arrows 427 shown in FIG. 11.

The outer surfaces of the distal and proximal end portions 422, 426 form seals against the inner wall of the inferior vena cava when the venous perfusion stent is in the radially expanded state. Thus, the outer surface of the distal and proximal end portions 422, 426 of the stent in the radially expanded state can have a diameter that is about the diameter of the inner surface in the region of the inferior vena cava where the stent will be placed. For example, for a perfusion stent to be placed in an adult, the outer surface of the distal and proximal end portions 422, 426 of the stent in the radially expanded state can have a diameter ranging from 15 mm to 3 cm. Smaller stents can be used in pediatric patients.

Figure 12:
FIG. 12 is a side view of an annular frame of a perfusion stent, according to one embodiment.
Figure 12:
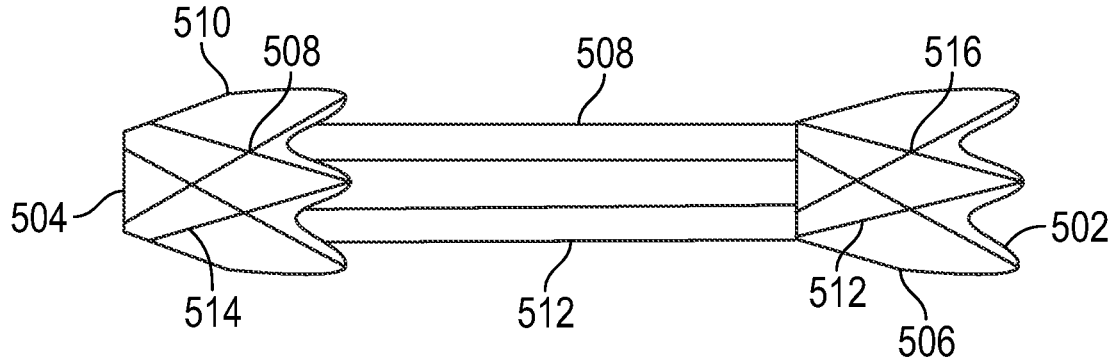

FIG. 12 shows an alternate embodiment of an expandable annular frame indicated generally at 500 that can be used for the perfusion stent 402 or the perfusion stent 404. As shown, the frame 500 has a distal end 502 and a proximal end 504. The frame 500 can comprise an enlarged distal end portion 506, a generally cylindrical intermediate portion 508, and an enlarged proximal end portion 510. In the radially expanded state of the perfusion stent, the distal and proximal end portions 506, 510 have an outer diameter that is larger than the outer diameter of the intermediate portion 508. The intermediate portion 508 can be formed from a plurality of longitudinally extending frame members, or struts, 512. The distal and proximal end portions 506, 510 can be formed from angled struts 514 that are welded or otherwise secured to each other at nodes 516 formed from the vertices of adjacent bends so as to form a mesh structure. Converging wires or struts at the distal end of the stent are permanently affixed to the stent so as to allow retrieval of the stent by sheath advancement.

Figures 19A, 19B, 19C, 19D:
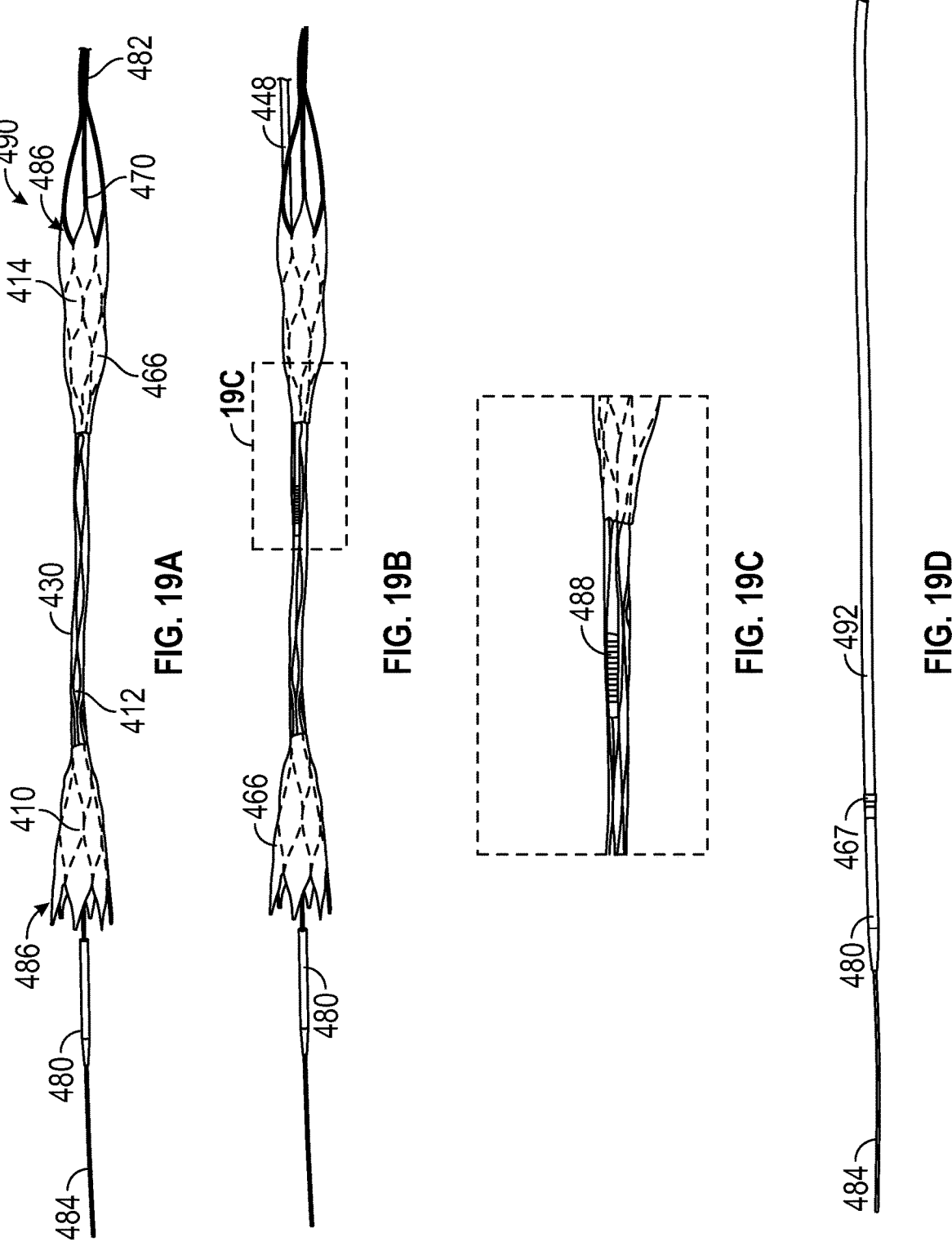
FIG. 19A is a side view of an exemplary prototype device of the perfusion stent of FIG. 13.
FIG. 19B is a side view of the device of FIG. 19A with an integrated guidewire and nosecone.
FIG. 19C is a detail view of a portion of the device of FIG. 19B.
FIG. 19D is a side view of the guidewire and nosecone of FIG. 19B, extending from a sheath with the device of FIGS. 19A and 19B radially compressed therein.

For example, converging wires 470 (as shown in FIG. 19A, which can also be referred to herein as recovery wires) may be permanently affixed to the frame of the stent (e.g., at the distal end) and may converge into a single shaft or wire included as part of a delivery device. The single shaft or wire can extend outside the body of the patient and be connected, at its proximal end, to a handle or other component of the delivery device that is configured to control the delivery device (e.g., control the sheath and position of the stent). In any of the stent or implantable device embodiments described herein, the component wires of the stent/frame can be oriented longitudinally (as shown in FIGS. 12, 19A-19B, 20H, 33, 34, and 39, for example), which facilitates device recapture and removal from the patient's body (e.g., after therapy or delivery of a therapeutic agent, as described further herein). For example, the converging, longitudinally oriented wires of the frame create a region (e.g., rail) that a sheath can be more easily slid over to collapse the stent frame and remove the device from the blood vessel.

The struts 512, 514 of the distal, intermediate, and proximal portions of the perfusion stent can be made of a suitable shape memory material, such as the nickel titanium alloy known as Nitinol, that allows the stent to be compressed to a reduced diameter for delivery in a delivery apparatus (such as described below) and then causes the perfusion stent to expand to its functional size inside the patient's body when deployed from the delivery apparatus. Specifically, the shape memory stent graft can be compressed into a delivery sheath. Advancement of the stent from the sheath, using a distal delivery wire for example, results in expansion of the stent to the shape memory dimensions of the stent.

If the perfusion stent is a balloon-expandable perfusion stent that is adapted to be crimped onto an inflatable balloon of a delivery apparatus and expanded to its functional size by inflation of the balloon, the perfusion stent 402 can be made of a suitable plastically expandable material, such as stainless steel.

The distal, intermediate, and proximal portions 506, 508, 510 can be constructed as a single unit, such as by machining (e.g., laser cutting). Alternatively, the frame can be constructed of separate segments each comprising respective struts or frame members, and each segment can be welded or otherwise secured together using means known in the art. In one example, the distal, intermediate, and proximal portions 506, 508, 510 are each constructed separately and secured together.

As shown in FIG. 12, the distal end portion 506 of the frame 500 in its radially expanded state can have a cylindrical shape at its distal aspect and can gradually decrease in diameter to the diameter of the intermediate portion 508. The proximal end of the distal end portion of the frame 500 is secured to the distal end of the intermediate portion 508 of the frame 430. The intermediate portion 508 of the frame in its radially expanded state generally has a uniform cylindrical shape having a diameter that is narrower than the outermost diameter of the distal and proximal end portions 436, 440 of the frame 500. The proximal end of the intermediate portion of the frame 500 is secured to the proximal end portion 510 of the frame 500. The proximal portion 510 of the frame 500 in its radially expanded state can have a cylindrical shape at its distal aspect and can gradually decrease to a narrower diameter at its proximal end, for example, to the diameter of the intermediate portion 508. The tapered proximal sections of the distal end portion 506 and the proximal end portion 510 can facilitate re-sheathing and recapture of the stent, as further discussed below.

Although a particular shape for the frame 500 is shown in FIG. 12, any shape that allows for delivery of the perfusion stent to appropriate vessel location in the patient and for formation of a seal against the inner wall of the aorta and isolation of blood flow from the aorta to the visceral arties can be used.

The venous perfusion stent 404 can also include an expandable annular frame, which can be substantially identical to frame 500 of the arterial perfusion stent. However, the frames of the arterial and venous perfusion stents 402, 404 can include minor structural differences (for example in the diameter or length of the perfusion stent) as needed for the placement and fit of the stents when implanted in to the aorta or inferior vena cava of the patient, respectfully.

Referring to FIG. 11, the arterial perfusion stent 402 comprises a perfusion conduit 446 that facilitates perfusion of blood or other perfusion fluid to the abdominal organs in the direction of arrows 452. The arterial perfusion conduit 446 comprises an outlet 447 that opens into the arterial perfusion space 416. The perfusion fluid can flow through a perfusion lumen 450 (FIG. 16) of the arterial perfusion conduit 446 into the arterial perfusion space 416. The arterial perfusion conduit 446 can extend at least partially through the proximal end portion 414 of the stent body and has a proximal end that can extend beyond the proximal end portion 414, where it can be fluidly connected to a catheter 456 that extends outside of the body of the patient. Desirably, the catheter 456 can be connected to an oxygenator and/or blood warmer 458 and/or a blood pump 460. The oxygenator can add oxygen to the blood or other fluid flowing through the catheter, and the pulsatile pump can push blood flow in the direction of arrow 461 through the endovascular apparatus 400 and the abdominal organs of the patient.

The arterial perfusion conduit 446 can be placed anywhere in the stent body that allows the perfusion lumen 450 to be in fluid communication with the arterial perfusion space 416. In the illustrated embodiment, the arterial perfusion conduit extends from the interior of the proximal end portion 414 of the stent body to the arterial perfusion space 416, thereby allowing such access.

The venous perfusion stent 404 comprises a perfusion conduit 448 that facilitates perfusion of the perfusion fluid from the abdominal organs in the direction of arrows 462. The venous perfusion conduit 448 comprises an inlet 449 at its distal end that opens into the venous perfusion space 428. The perfusion fluid can flow from the venous perfusion space 428 and into a perfusion lumen of the venous perfusion conduit 448. The venous perfusion conduit 448 can extend at least partially through the proximal end portion 426 of the stent body and has a proximal end that can extend beyond the proximal end portion 426, where it can be connected to a catheter 464 that extends outside of the body of the patient and connects to the blood pump 460 (as shown) and/or the oxygenator and/or blood warmer 458.

The venous perfusion conduit 448 can be placed anywhere in the stent body that allows the perfusion lumen of the venous perfusion conduit 448 to be in fluid communication with the venous perfusion space 428. In the illustrated embodiment, the venous perfusion conduit extends from the interior of the proximal end portion 426 of the venous perfusion stent 404 to the venous perfusion space 428, thereby allowing such access.

Referring again to FIG. 13, as noted above the arterial perfusion stent 402 can include a liner 466 that is non-porous to the perfusion fluid (blood, in the illustrated embodiment). The liner can be secured to the frame 430 by any suitable means, for example an adhesive or suturing. The liner covers the frame 430 of the arterial perfusion stent and prevents or substantially reduces mixing of blood flowing through the aorta and the central lumen 403 with the perfusion fluid flowing through the perfusion space 416. The venous perfusion stent 404 includes a non-porous liner that can be substantially identical to the liner used for the arterial perfusion stent, and that prevents or substantially reduces mixing of blood flowing through the inferior vena cava with the perfusion fluid flowing through the perfusion space 428. However, the liners of the arterial and venous perfusion stents 402, 404 can include minor structural differences (for example in diameter or length) as needed for sufficient coverage of the arterial and venous perfusion stents. In the illustrated embodiment, the liner is located on the outside of the frame of the perfusion stent. However, the liner can be located on the stent in any way that provides a non-porous barrier to blood. For example, the liner can be located on the inside of the frame of the stent, or on both the outside and the inside of the stent.

In several embodiments, the liner 466 can be made of any suitable bio-compatible synthetic or biological material, such as those described in U.S. Pat. No. 6,730,118, which is incorporated herein by reference. The liner 466 desirably can be substantially impermeable to aqueous solutions, such as blood or plasma. In some embodiments, the liner 466 can be a polymer or composite membrane or layer, for example, polytetrafluoroethylene (PTFE); or a woven, knit, or non-woven fabric material (e.g., a ripstop fabric) manufactured from natural and/or synthetic yarns or fibers, such as woven polyester (e.g., polyethylene terephthalate, PET, such as Dacron®), or cellulose (such as cotton or linen), silk, nylon, polyolefin, carbon fiber, and/or metal fibers. In additional embodiments, the liner 466 can be made of a synthetic and/or natural material that is coated with a sealant (such as ePTFE, fluoropolymer, or gelatin (Vasutek® Gelatin Sealant, Terumo, UK); see, e.g., International Publication No. WO 2001/080918, which is incorporated by reference herein in its entirety). In more embodiments, the liner 466 can be made of a bio-synthetic materials and composites (e.g., collagen-polyester composites, Omniflow®, Bio Nova, Melbourne, AU). Other embodiments use natural tissue, including intestinal submucosa, natural blood vessels (arteries or veins, e.g., from animal sources), pericardial tissue and the like, which may be fixed (for example, using gluteraldehyde and/or formaldehyde). Other embodiments include artificial collagen or cellulose tubes.

In some embodiments, the liner 466 is manufactured from sheet stock, two edges of which are brought together, for example, overlapped and/or abutted, and sealed or closed to form a tube comprising a seam. In some embodiments, the seam is linear, for example, extending along a longitudinal axis. In other embodiments, the seam has a different shape, for example, zig-zag or helical. The edges are closed using any suitable method, for example, suturing, welding, gluing, laminating, and/or bonding. In other embodiments, the liner 466 does not comprise a seam, for example, when the tubular sealing member comprises a portion of a blood vessel, intestinal submucosa, or certain artificial tubular structures.

In additional embodiments, the liner 466 can desirably be made of an electrospun polyurethane fabric (see, e.g., Amoroso et al., Elastomeric electrospun polyurethane scaffolds: The interrelationship between fabrication conditions, fiber topology, and mechanical properties. *Advanced materials.* 23:106-111, 2011, which is incorporated by reference herein in its entirety). Another embodiment is direct encapsulation of the frame with another polymer (e.g. polytetrafluoroethylene) to improve adherence to the frame.

In particular embodiments, the frame 430 of the stent can comprise a micro-pattered thin Nitinol film (see, e.g., WO2004/028340; Chun et al., Thin film nitinol microstent for aneurysm occlusion, *J. Biomechanical Engineering,* 131(5):051014, 8 pages, 2009; Chun et al., Novel micro-patterning processes for thin film niti vascular devices *Smart Materials and Structures,* 19:105021, 2010; Chun et al., Modeling and experimental analysis of the hyperelastic thin film nitinol, *Journal of Intelligent Material Systems and Structures.* 22, 2045-2051, 2011; Rigberg et al., Thin-film nitinol (niti): A feasibility study for a novel aortic stent graft material *Journal of vascular surgery,* 50:375-380, 2009; each of which is incorporated by reference herein in its entirety). Micro-fabrication techniques can be used to form a plurality of micro-openings or apertures in a thin sheet of Nitinol (about 6 µM) so as to form a thin film lattice or mesh. A layer of non-porous material, such as polyurethane or ePTFE, can be applied to and secured to the metal film to provide the liner 466.

Figure 17:
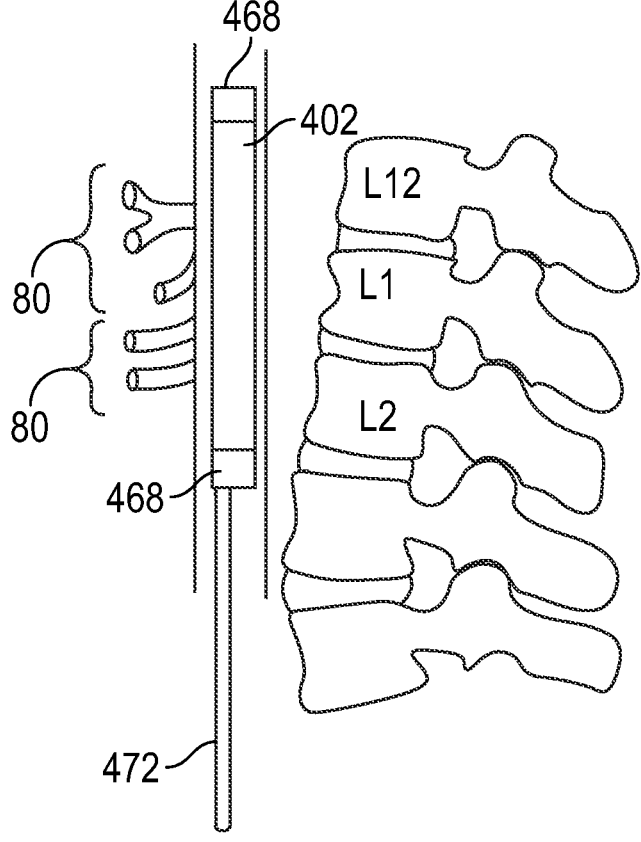
FIG. 17 shows a perfusion stent being positioned within the aorta of a patient.

FIG. 17 depicts the stent 402 being positioned relative to anatomic landmarks and vascular branches before deployment from a sheath 472 of a delivery apparatus. As shown, each of the perfusion stents 402, 404 can include suitable positioning markers and/or sensors at convenient locations to assist in locating the proximal and distal end portions of each perfusion stent at the desired locations within the aorta or the inferior vena cava. For example, each of the distal end portion 410 and proximal end portion 414 of the arterial perfusion stent 402 can include a respective positioning marker 468 (see FIG. 17). In some embodiments, the positioning markers 468 can be radiopaque markers that can be used to locate the position of the stent during deployment in a patient by radiography. For example, an x-ray image of the stent within the body of the patient can be obtained using a bed-side x-ray machine to determine the position of the stent within the aorta or inferior vena cava. Certain bones or other tissue visible under x-ray can be used as landmarks to help position the stent relative to the visceral arteries. For example, the radiopaque markers 468 can be positioned above and below the T12 and L2 vertebrae. Although the illustrated embodiment includes a pair of positioning markers for the arterial perfusion stent, a greater or fewer number of markers can be provided as needed for the surgeon to properly position the stent in the aorta of the patient. The distal end portion 422 and proximal end portion 426 of the venous perfusion stent 404 similarly can include a corresponding pair of radiopaque markers that can be used to position the venous perfusion stent in a patient by radiography.

In an alternative embodiment, positioning markers 468 can be provided on the sheath 472. When the stent 402 is located in the sheath, one marker is aligned with the distal end portion 410 of the stent and the other marker is aligned with the proximal end portion 414.

In alternative embodiments, the positioning markers can comprise passive or active emitters that can emit electromagnetic waves through the body and a corresponding detector or monitor can be used to receive the electromagnetic waves from the emitters and provide visual and/or audible feedback to a user indicating the position of the markers inside the body relative to external landmarks on the body. In particular embodiments, for example, the positioning markers can be emitters that can emit radiofrequency waves, such as radiofrequency identification (RFID) or magnetic detection tags. Further details of the use of RFID tags as positioning marks are disclosed in Application No. 61/845,896, filed Jul. 12, 2013, which is incorporated herein by reference.

Referring to FIG. 11, the arterial and venous perfusion stents can be secured to respective one or more converging or recovery wires 470. The recovery wires 470 can be secured to the proximal end of the frame of the perfusion stents and can extend proximally from the perfusion stents to outside the patient's body via the artery or vein through which the perfusion stent was deployed. If it is desired to re-position or remove the arterial and/or venous perfusion stents from the patient (for example, if the patient recovers), then tension can be applied to the recovery wires to retract the perfusion stents in the proximal direction into respective sheaths 472. Once the stents are retracted into the sheaths 472, the sheaths can be withdrawn from the body. The tapered sections 411b, 415b of the end portion of the stent facilitate recapture of the stent back into the sheath 472.

In use, as depicted in FIG. 10, the arterial perfusion stent 402 can be inserted into the aorta via an incision in a femoral artery in a minimally invasive manner using known techniques. Similarly, the venous perfusion stent 404 can be inserted into the inferior vena cava via an incision in a femoral vein in a minimally invasive manner Guidewires, dilators and/or introducers can be used to help introduce and advance the perfusion stents through the patient's vasculature, as known in the art. As best shown in FIG. 11, the arterial perfusion stent is positioned such that the distal end portion 410 is upstream of the visceral arteries 80 and the proximal end portion 414 is positioned downstream of the visceral arteries 80. Similarly, the venous perfusion stent 404 is positioned such that the distal end portion 422 is positioned downstream of the visceral veins 84 and the proximal end portion 426 is positioned upstream of the visceral veins 84. The proper positioning of the perfusion stent 402, 404 can be accomplished by viewing the markers 468 by x-ray or under fluoroscopy, for example.

Once the arterial and venous perfusion stents are in place, the proximal and distal end portions of each stent form a seal against the inner walls of the aorta and inferior vena cava, respectively, thereby isolating blood flow from the aorta 82 to the visceral arteries 80 and from the visceral veins 84 to the inferior vena cava 86. The perfusion cannula 449/454 may be integrated to the stent structure or may be delivered in a modular format to the docking sites 446/448.

Thus, blood from the heart can flow through the arterial stent 402 (bypassing the visceral arteries), through the vasculature of the lower extremities, through the venous stent 404 (bypassing the visceral veins), and back to the heart. The blood flow to and from the visceral organs is redirected from the venous perfusion space 428 around the venous perfusion stent 404 through the venous perfusion conduit 448 and via the catheter 464 to the blood pump 460, blood oxygenator and/or warmer 458 that are outside the patient's body. The blood is then redirected back into the patient via the catheter 456 connected to the arterial perfusion conduit 446 and into the arterial perfusion space 416 around the arterial perfusion stent 402. The blood flows through the visceral arteries 80 to the abdominal organs, and back to venous perfusion space 428 via the visceral veins 84.

Although perfusion with the patient's blood is discussed above, use of a cold perfusion fluid is also available. The cold perfusion fluid can be introduced into the arterial perfusion space 416 via the arterial perfusion conduit 446, and retrieved from the venous perfusion space via the venous perfusion conduit 448 similar to that shown in FIG. 2.

In particular embodiments, the perfusion fluid can be similar to the University of Wisconsin solution and can comprise, without limitation, one or more of the following compounds: heparin, pentastarch, steroids, lactobionic acid, magnesium sulfate, raffinose, adenosine, allopurinol, glutathione, and potassium hydroxide. The perfusion fluid can be cooled to a temperature of about 0 degree C. to about 10 degrees C. for introduction into the body and more preferably to a temperature of about 4 degrees C. to about 6 degrees C. As an alternative perfusion fluid, blood separate from the circuit of blood being circulated by the heart can be propelled, oxygenated and warmed before being cycled continuously through the catheters, as further described below.

The apparatus 400 is particularly suited for use with consented DCD donors. In this regard, the perfusion stent 402, 404 can be inserted and deployed in the vasculature of a DCD donor as soon as possible prior to cardiac death. For example, the perfusion stent 402, 404 can be inserted and deployed in a DCD donor just prior to or at the same time as removing the patient from life support or when the donor is experiencing unstable vital signs for normal organ blood flow. The blood flow circuit allows for normal blood flow through the body, except for those isolated regions, while awaiting expected cardiac death and during the predetermined waiting period before explant can occur. In another implementation, the perfusion stents 402, 404 can be inserted into the DCD donor prior to cardiac death and then are deployed at the time of cardiac death. In yet another implementation, the apparatus can be inserted and deployed in a donor who expires prematurely before a donor team is ready to perform the explant procedure. In any case, during the period of time before explant can be performed, the perfusion fluid reduces warm ischemia time and preserves organ function.

Figure 18:
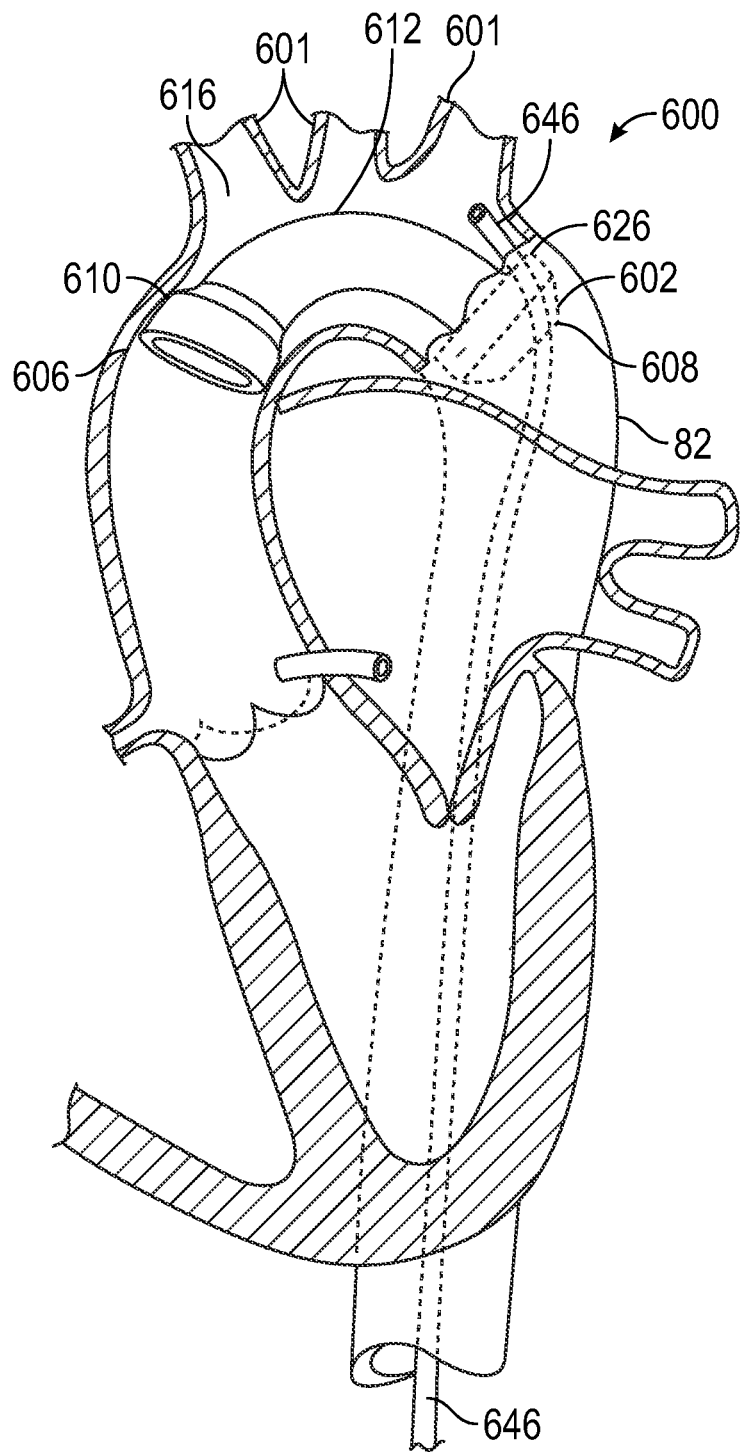
FIG. 18 illustrates an exemplary embodiment of an endovascular apparatus for perfusing arch vessels (e.g. brain and upper extremity) of a patient, according to another embodiment.

FIG. 18 shows an endovascular apparatus 600, according to another embodiment. The endovascular apparatus 600 is similar in many respects to the apparatus 400 of FIGS. 10 and 11, but has been modified for deployment in the aortic arch and superior vena cava to isolate and perfuse the head and arms of a patient with a perfusion fluid or warmed/oxygenated blood. The apparatus 600 may also have permanently affixed retrieval wires, similar to 470 of FIG. 11 and FIG. 19A (described further below).

The apparatus 600 in the illustrated embodiment comprises an arterial perfusion stent 602 and a venous perfusion stent (not pictured). The arterial perfusion stent 602 is configured for deployment in the aortic arch and to isolate blood to the head and arms via carotid and subclavian arteries 601. When deployed in a patient, the endovascular apparatus 600 allows blood from the heart to pass uninterrupted through a central lumen of the arterial perfusion stent 602 and flow via the aorta 82 to perfuse the abdomen and lower body and then flow uninterrupted through the inferior vena cava to return to the heart. Further, the arterial perfusion stent 602 of endovascular apparatus 600 is configured to introduce a perfusion fluid (e.g., re-oxygenated and/or warmed blood) into the carotid and subclavian arteries 601 for the purpose of perfusing the head and arms with the perfusion fluid. For example, the apparatus 600 can be used to maintain blood flow to the brain or spinal cord during a surgical procedure that restricts such flow in order to reduce or prevent brain ischemia or spinal cord ischemia during the procedure.

The arterial perfusion stent 602 can have a similar construction as that of the arterial perfusion stent 402. The size and shape of the arterial perfusion stent 602 can be generally similar to the size and shape of the arterial perfusion stent 402, with modifications as needed to allow for deployment of the arterial perfusion stent 602 in the aortic arch. For example, similar to arterial perfusion stent 402, the arterial perfusion stent 602 comprises an elongated body that includes an annular frame supporting a non-porous liner that can be radially compressible to a compressed state for delivery through the body to a deployment site and expandable to its functional size shown in FIG. 18 at the deployment site. Similar to perfusion stent 402, the perfusion stent 602 can be self-expanding, or, in other embodiments, can be a plastically-expandable perfusion stent. The frame and the non-porous liner of the arterial perfusion stent 602 can be made of the same materials as those used for the arterial perfusion stent 402.

The stent 602 defines a central lumen that extends from a proximal end 608 to a distal end 606 of the perfusion stent. The central lumen allows passage of fluid (e.g., blood) through the body of the perfusion stent, thus maintaining blood flow through the artery in which the perfusion stent is deployed. In the radially expanded state of the perfusion stent, distal and proximal end portions 610, 614 have an outer diameter that is larger than the outer diameter of an intermediate portion 612, thereby defining an annular perfusion space 616 between the end portions and around the intermediate portion. The outer surfaces of the distal and proximal end portions 610, 614 form a seal against the inner wall of the aorta when the arterial perfusion stent is in the radially expanded state.

Similar to the arterial perfusion stent 402, the arterial stent 602 can comprise a perfusion lumen (such as defined by an arterial perfusion conduit or sleeve 646) that is in fluid communication with the arterial perfusion space 616 and facilitates perfusion of blood or fluid through the head and arms, while allowing normal blood flow between the heart and lower extremities. The perfusion fluid can flow through the perfusion lumen and into the arterial perfusion space 416. The arterial perfusion conduit 646 can extend at least partially through the proximal end portion 614 of the stent body and has a proximal end that can extend beyond the proximal end portion 614, where it can be fluidly connected to a catheter that extends outside of the body of the patient. Desirably, the catheter can be connected to an oxygenator and/or blood warmer and/or a blood pump to treat and pump the blood of the patient as needed.

The venous perfusion stent included in the apparatus 600 can be configured for deployment in the superior vena cava to isolate blood flow returning from the head and arms to the heart via the superior vena cava. The venous perfusion stent is configured to receive the perfusion fluid from the superior vena cava that was introduced into the body from the arterial perfusion stent 602. The venous perfusion stent of apparatus 600 can have a structure similar to the venous perfusion stent of apparatus 400, and can be configured for placement in the superior vena cava in any way so as to collect fluid returning via the superior vena cava to the heart. In some non-limiting embodiments the venous stent can include a configuration such that a perfusion space of the stent collects fluid (e.g., blood) from the right brachiocephalic vein, the left internal jugular, or the right brachiocephalic vein and the left internal jugular.

Once the arterial and venous perfusion stents of the apparatus 600 are in place, the proximal and distal end portions of each stent form a seal against the inner walls of the aortic arch and superior vena cava, respectively, thereby isolating blood flow from the aorta to the carotid and subclavian arteries 601 and from the veins of the head and arms to the superior vena cava. Thus, blood flow to and from the head and arms is redirected from the superior vena cava through a venous perfusion conduit to a blood pump, blood oxygenator and/or warmer that are outside the patient's body. The blood is then redirected back into the patient via the catheter connected to the arterial perfusion conduit 646 and into the arterial perfusion space 616 around the arterial perfusion stent 602. The blood flows through the carotid and subclavian arteries 601 to the head and arms, and back to superior vena cava.

FIGS. 19A-19C illustrate an exemplary prototype device 490 of the perfusion stent of FIGS. 13-16 which may be used for one or more of the embodiments described above or further below (e.g., perfusion, drug delivery, or vascular surgery). The perfusion stent may also be referred to herein as a multi-lumen implantable device.

As shown in FIGS. 19A-19C, the prototype device 490 has a flared distal end portion 410, a flared proximal end portion 414, and a narrower intermediate portion 412 arranged therebetween. The device 490 has a frame (e.g., stent frame) 430 which is covered with a non-porous liner 466. In FIGS. 19A-19C, the dashed lines represent portions of the frame 430 which are covered by the non-porous liner 466 (e.g., at the distal end portion 410 and the proximal end portion 414).

The frame 430 comprises a plurality of longitudinally arranged struts (e.g., in a direction of a central longitudinal axis of the device 490) that converge at a proximal end of the proximal end portion 414 into converging wires 470. As described above, the converging wires 470 converge into a single wire or shaft 482 that can extend outside a body of the patient and connect to a handle or another component adapted to control deployment and retrieval of the device 490 to and from the patient's blood vessel. In particular embodiments, the frame 430 is permanently attached to the wire or shaft 482.

The device 490 can also include an integrated guidewire 484 and nosecone 480 for expedited delivery of the device 490 to the target blood vessel, as shown in FIGS. 19A-19C. As shown in FIG. 19D, a sheath 492 can extend over and retain the device in a radially compressed state for delivery into a patient's vasculature. Once positioned at a target site within a vessel of the patient (e.g., the aorta), the sheath can be retracted to allow the device to expand against the inner wall of the vessel. Following the procedure, the device can be retracted back into the sheath. The converging wires 470 assist in recapturing the device back into the sheath by allowing the sheath to be advanced over the converging wires 470, which promotes radial compression of the remaining portion as it is brought back into the sheath.

In some embodiments, as shown in FIG. 19D, the sheath 492 can include a light 467, such as a light-emitting diode (LED), arranged on an exterior of the sheath 492. In certain embodiments, such as when the device 490 is being delivered to a target location for vascular repair or the creation of vascular bypass anastomoses, when the sheath 492 is placed into and navigated through a blood vessel to the target location, the illumination of the light 467 may be seen through the wall of the blood vessel. As a result, a user (e.g., medical professional) operating the delivery device including the sheath 492 can see a position of the sheath 492 (and thus the device 490 contained therein) within the blood vessel and can more accurately and easily navigate the device 490 to the target location for implantation. In some embodiments, as shown in FIG. 19D, the light 467 is arranged on the sheath 492, adjacent to a proximal end of the nosecone 480. In alternate embodiments, the light 467 can be arranged on the sheath 492, further away from the nosecone 480 or on the nosecone 480 itself.

Returning to FIG. 19A, scalloped seal zones 486 of the device 490 can optimize seal against the wall of the blood vessel in which it is implanted under relatively strong blood flow (e.g., aortic flow).

As shown in FIG. 19C, a cylindrical extension portion 488 resembling a chimney can optimize a seal with the perfusion conduit (e.g., cannula) 448 of the device 490.

The embodiments disclosed herein can be used for procedures other than procedures for preserving organ function for explant surgery. For example, in another implementation, an endovascular apparatus (e.g., an apparatus of FIG. 1, 5, 6, 10, 11, 12, or 18) can be used to perfuse organs during survival surgery, such as cardiac or proximal aortic repairs where prolonged cessation of blood flow poses a risk of organ damage. In another implementation, an endovascular apparatus (e.g., an apparatus of FIG. 1, 5, 6, 10, 11, 12, or 18) can be used to selectively perfuse organs, but not other body regions, with a therapeutic agent. For example, if a particular therapeutic agent has therapeutic effect on the organs, but is toxic to other body regions (for example, the central nervous system), the agent can be selectively administered to the organs using a disclosed endovascular apparatus. In one non-limiting example, a chemotherapeutic agent can be delivered to the visceral organs using a disclosed endovascular apparatus (e.g., an apparatus of FIG. 1, 5, 6, 10, 11, or 12) to selectively perfusion the visceral organs of the body with a solution (e.g., blood) that includes the chemotherapeutic agent. Other potential agents for isolated perfusion of the viscera include thrombolytics, immune modulators, gene vectors, or vasodilators.

In yet another implementation, the endovascular apparatuses and/or implantable devices discussed herein (including further below) having flared ends adapted to have sealing contact with a wall of a blood vessel and a narrower central portion arranged therebetween (e.g., having a dumbbell shape), can be used in various medical procedures in the place of vascular (e.g., surgical) clamps.

Figures 20E, 20F, 20G, 20H:
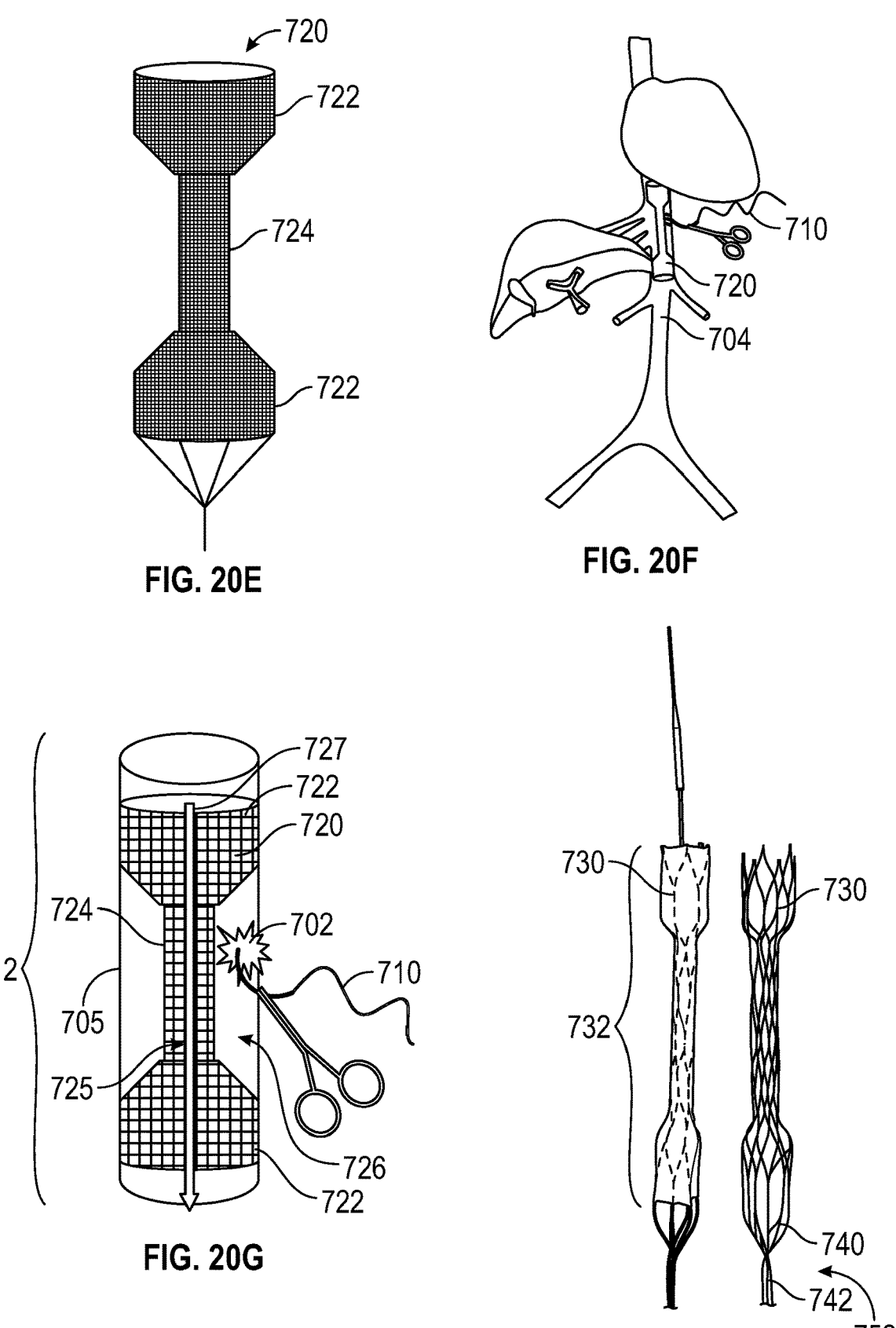
FIG. 20E illustrates an exemplary multi-lumen implantable device comprising a radially expandable stent with opposing, flared end portions and a narrower, central portion arranged between the flared end portions.
FIG. 20F illustrates the device of FIG. 20E implanted in a blood vessel to aid in a vascular repair procedure.
FIG. 20G illustrates the device of FIG. 20E implanted in a blood vessel and maintaining blood flow through a central lumen of the device while blocking blood from entering a void portion where a vessel repair takes place.
FIG. 20H illustrates a prototype multi-lumen device, which may be used as the multi-lumen device of FIGS. 20E-20G.

As one example, as depicted in the examples of FIGS. 20A-20H, vascular surgery may be required to repair injured blood vessels. Specifically, an injury 702 may occur at a location in a blood vessel 704 (e.g., a segment of the inferior vena cava, as shown in FIG. 20A). As shown in FIG. 20B, traditionally, to repair an injured blood vessel, vascular clamps 706 and 708 can be placed upstream and downstream of the injury 702 in order to cut off blood flow to the injured region and reduce bleeding during surgical repair (e.g., suturing, as shown at 710). However, the use of vascular clamps may not be advisable in the cava as it would cause a loss of critical venous return to the heart with hemodynamic instability.

Alternately, for an injury in an artery, as shown in FIG. 20C, the traditional use of vascular clamps can lead to distal ischemia in a portion of a blood vessel 705 (e.g., may be a different blood vessel than vessel 704 shown in FIGS. 20A and 20B) that is arranged downstream of the upstream clamp 706 (when the blood flow through the blood vessel 705 is in a direction from the upstream clamp 706 to the downstream clamp 708). The ischemic region 714 and the blood flow region 712 are shown in FIG. 20C.

In some embodiments, as shown in FIG. 20D, a cylindrical stent 716 can preserve blood flow through the blood vessel (as indicated by the blood flow region 712 in FIG. 20D). However, suture repair may be prohibited due to a risk of capturing the frame of the stent 716 with each stitch.

Instead, an implantable device including a radially expandable stent (e.g., stent graft) can be used to preserve blood flow through an injured blood vessel, while repairing the injured blood vessel without the use of vascular clamps. For example, as shown in FIG. 20E and discussed further herein, an implantable device 720 comprising a radially expandable stent can include opposing, flared end portions 722 (e.g., upstream and downstream ends) and a narrower, central portion 724 arranged between the flared end portion 722. For example, as shown in FIG. 20E, the device 720 has a dumbbell shape. An exterior (and/or interior) of the stent frame of the device 720 can be covered with a non-porous liner that prevents fluids from passing through the liner.

As shown in FIGS. 20F and 20G, the device 720 can be expanded in a blood vessel 704 or 705 and the flared end portions 722 can form a seal against an inner wall of the blood vessel 705. As a result, blood can continue to flow (as shown by arrow 727) through a central lumen 725 of the device 720 (e.g., through the central portion 724) to prevent distal ischemia. However, due to the sealing against the blood vessel wall at the flared end portions 722 and the non-porous liner of the device 720, blood is blocked from flowing into a void portion 726 created between an exterior of the central portion 724 and the wall of the blood vessel 705 (as shown in FIG. 20C). Thus, the injured blood vessel 705 can be repaired, in the void portion 726, in a bloodless field and without catching the stent frame with a suture needle. After the blood vessel repair is complete, the device 720 may be radially compressed by sheath advancement over the stent and removed from the blood vessel.

FIG. 20H shows an exemplary prototype of the device 720 comprising a radially expandable frame 730 (on the right) covered with a sealing member 732 (e.g., a non-porous liner, as shown on the left, which can be any of the materials disclosed above for liner 466). As shown in FIG. 20H, the struts (or wires) of the frame 730 can be longitudinally arranged, in a direction of a central longitudinal axis of the device 720, and permanently connected to converging wires 740 which converge into a wire or shaft 742 of a delivery apparatus which extends outside a body of the patient. The longitudinal orientation of the wires of the frame 730 enable the device 720 to be more easily removed after use inside the blood vessel is complete.

Figure 21A:
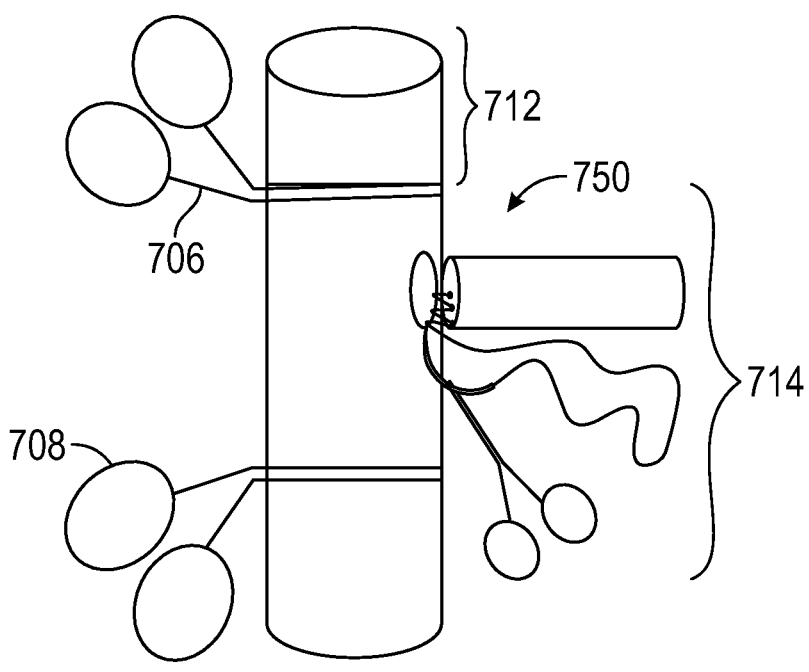
FIG. 21A illustrates traditional proximal and distal clamping for creation of a vascular bypass anastomoses which can result in creates ischemia (absent blood) distal to the clamps.
Figure 21B:
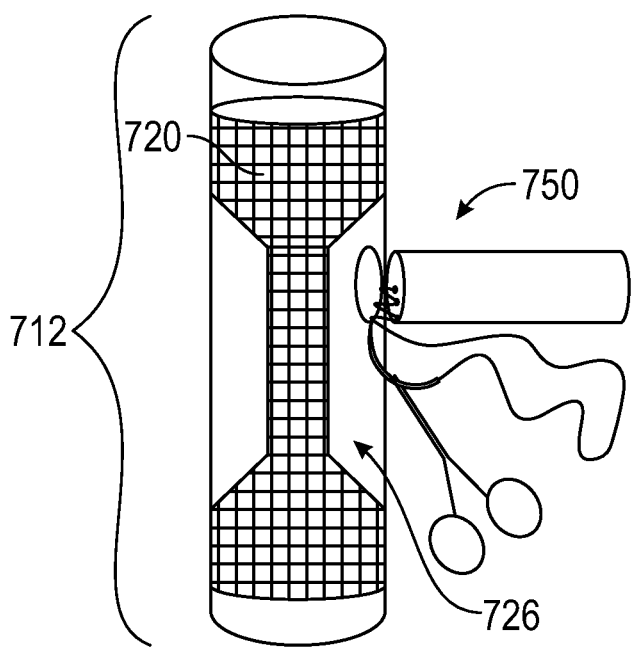
FIG. 21B illustrates the use of a multi-lumen implantable device with flared end portions (for sealing proximally and distally) and a narrow central portion that provides a bloodless chamber in which to create a vascular bypass anastomosis.

Similarly, as another example and as shown in FIG. 21B, the implantable device 720 can be used to create vascular bypasses without the need of vascular clamps. FIG. 21A shows traditional proximal and distal clamping using vascular clamps 706 and 708 for creation of a vascular bypass anastomoses 750 which creates ischemia (absent blood) distal to the clamps 706 and 708 (e.g., in ischemic region 714). By contrast, a dumbbell-shaped stent device 720 allows continued blood flow during the creation of the bypass without the need for clamps (as indicated by the blood flow region 712 in FIG. 21B). This avoids potential injury from clamp application and eliminates the need for additional operative exposure to allow clamp placement.

The device 720 can be retrievable and removed after the bypass is complete. For example, a proximal end 752 of the device 720 can include converging wires 740 connected to a single wire or shaft 742 that allows the device 720 to be recaptured back into a sheath for removal from the body (FIG. 20H). Examples of such devices having flared end portions and a narrower central portion (e.g., approximate dumbbell shape) are discussed above and further below. In certain embodiments, all the stent or implantable device embodiments described herein can include a frame that is coupled to a wire or shaft (which can be referred to herein as a delivery wire), such as shaft 742 shown in FIG. 20H, which allows the implantable device to be recaptured and removed from the body. In some embodiments, the wire or shaft can be permanently attached to the implantable device or stent.

In some embodiments, during placement of the implantable device 720, for either repair of vascular injuries or to facilitate open surgical bypass via the creation of anastomoses (as explained above with reference to FIGS. 20A-20H and 21A-21B) the device 720 may be positioned at the target location (e.g., for surgical repair or creation of the vascular bypass anastomosis) in the blood vessel by direct palpation of the delivery sheath (which contains the device therein in a radially compressed state for delivery to the target location) within the blood vessel. Alternately, in other embodiments, a light, such as a light-emitting diode (LED), mounted on the delivery sheath can transilluminate, through the vessel wall, to allow direct visualization of the sheath (and therefore the device 720 compressed therein) location through the wall of the vessel. An example of such a light positioned on a delivery sheath configured to deliver the device 720 to the target location in the blood vessel is shown in FIG. 19C, as described above.

In still another implementation, an endovascular apparatus (e.g., apparatus of FIGS. 1, 5, 6, 10, 11, 12, and/or 18) and the implantable devices discussed further below can be used to deliver a therapeutic agent, such as a drug, to a desired blood vessel in which it is deployed and implanted. Example therapeutic agents can include drugs to halt or slow aneurysm growth, anti-restenotic drugs or agents, anti-calcification drugs or agents, antibiotics, anti-neoplastic drugs or agents, vasoactive agents (e.g., vasodilators), and/or gene therapy vectors. The multi-lumen device may be designed to intentionally perfuse only branch vessels or alternately may be used for drug delivery to the vascular wall while excluding branch perfusion, as explained further below.

As introduced above, often only a segment of a blood vessel is in need of treatment, yet administering therapeutic agents intravenously or via a drug eluting stent or balloon result in the therapeutic agent being distributed throughout the entire body (instead of only to the target segment of the blood vessel). This may result in increased costs of the therapy (due to the high volume of drug needed), increased toxicity to the body, and decreased efficacy at the target location/blood vessel (e.g., only a fraction of the drug may be delivered to the target location/vessel while the rest is lost to the circulation).

Thus, the inventors herein have recognized that a multi-lumen (also referred to as multi-chamber) endovascular device and/or implantable device comprising a radially expandable frame (e.g., stent portion) with flared end portions and a central portion arranged therebetween (which may have a dumbbell-like shape in some embodiments), covered by a non-porous material or liner (that prevents fluid transfer across the liner), can provide targeted drug delivery to a selected portion of a blood vessel in which it is delivered (endovascularly via a delivery device) and implanted (via radial expansion of the frame from a radially compressed state used during delivery).

Figure 22A:
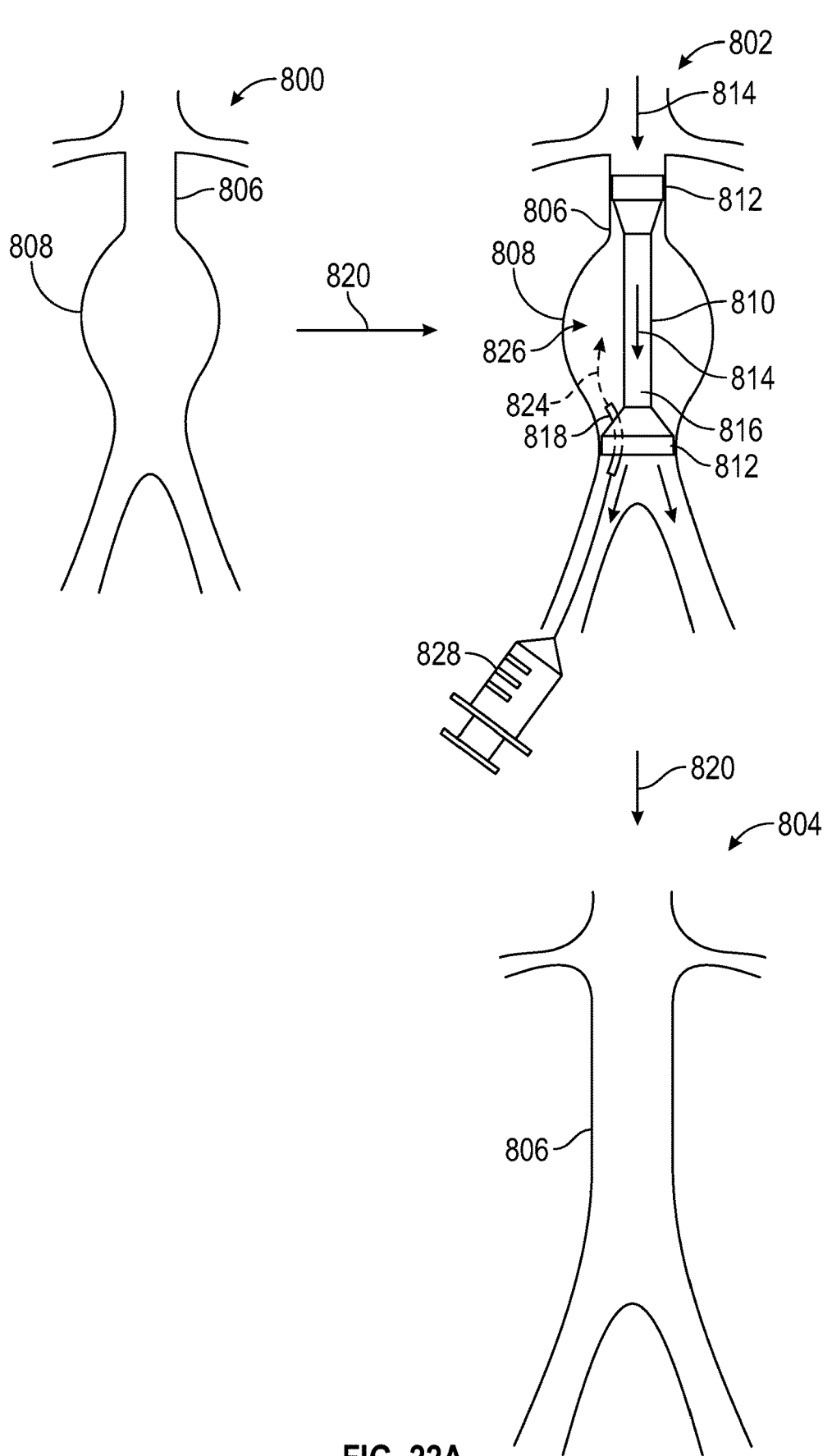
FIG. 22A illustrates an exemplary use of a multi-lumen implantable device to treat vascular disease (e.g., an aortic aneurysm).

FIG. 22A illustrates an exemplary use of such a multi-lumen implantable device to treat an aortic aneurysm 808 (as shown by the flow of the arrows 820). As shown at 800 in FIG. 22A, a blood vessel, such as a segment of the aorta 806 may have an aneurysm 808.

As shown at 802, the multi-lumen implantable device 810 can be delivered (e.g., via femoral access) to the aorta 806 and radially expanded at the location of the aneurysm 808. In its expanded state, the flared end portions 812 of the device 810 form a fluid seal against a wall of the aorta 806, upstream and downstream of the aneurysm 808 (e.g., an outer surface of the end portions 812 have face sharing contact with an inner surface of the wall of the aorta 806). In this way, the device 810 isolates the segment of the aorta 806 containing the aneurysm 808.

The covered, central lumen 816 of the device 810 provides continued distal blood flow (show by solid arrows 814) while a perfusion lumen 818 of the device 810 is used to deliver an aneurysm stabilizing therapeutic agent 824 to an outer lumen/chamber 826 of the device 810 (e.g., created between a covered (and fluidly isolated/sealed), outer surface of the central lumen 816 and an inner wall of the blood vessel or aorta 806 containing the aneurysm 808). For example, as shown at 802, the perfusion lumen 818 may be fluidly coupled with a catheter or delivery cannular 828 adapted to inject the aneurysm stabilizing therapeutic agent 824. Furthermore, the perfusion lumen 818 may also be delivered in a modular fashion to dock with the device 810 to a create a fluidic seal for drug delivery.

Since the outer chamber 826 is arranged in the region of the aneurysm 808, the aneurysm stabilizing therapeutic agent 824 is delivered directly to the wall of the aneurysm 808. Thus, as shown at 804, the aneurysm 808 may be more effectively stabilized or reduced without leaking the aneurysm stabilizing therapeutic agent to other portions of the body (e.g., via the systemic circulation). Following the drug delivery, the drug is aspirated from the outer chamber 826 and the device is collapsed by sheath advancement and removed from the body, as shown at 804.

Figure 22B:
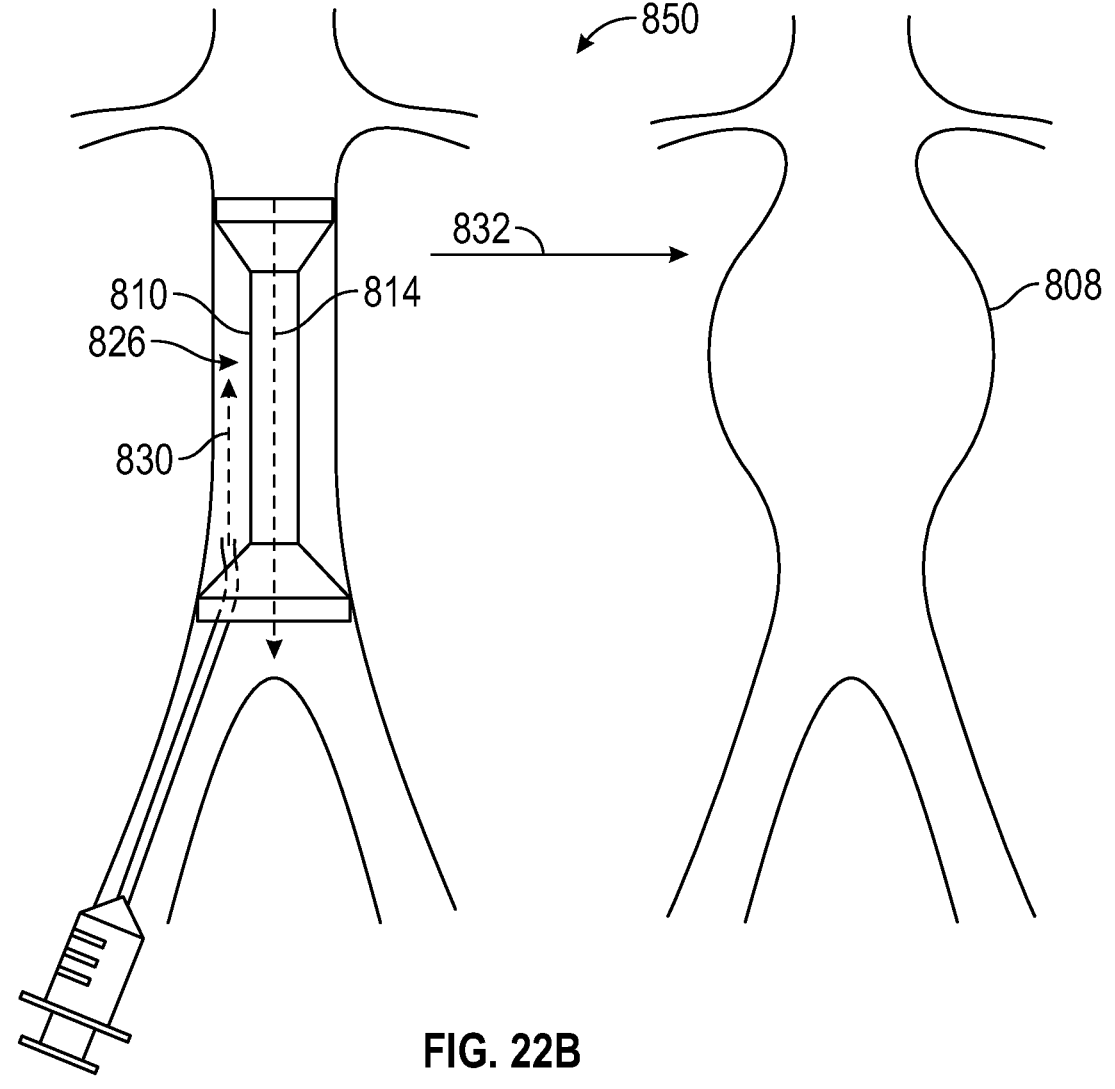
FIG. 22B illustrates an exemplary use of a multi-lumen implantable device to create vascular disease (e.g., an aortic aneurysm) for the creation of an animal model.

In other embodiments, as shown in schematic 850 of FIG. 22B, the same or similar device 810 can be used to create an aneurysm (via injection of an aneurysm promoting therapeutic agent 830 into the outer chamber 826) or other vascular disease state for use as a large animal model (e.g., a cow, pig, sheep, etc.). For example, currently, small animal (e.g., mouse) models may be used to create various vascular disease states (e.g., aneurysms) that can be used for studying the effectiveness of various treatments (e.g., drug therapies). However, large animal models may more closely model human vasculature and provide better disease models.

Thus, a multi-lumen implantable device, such as device 810 and/or any of the devices described further below, can be used to create the aneurysm 808 (or other vascular disease state) in a larger animal, such as a cow, pig or sheep, by delivering an aneurysm promoting therapeutic agent 830 (e.g., elastase, chemical or modulation of genes or gene expression) to the outer chamber 826, as shown in FIG. 22B. Then, after a period of time (e.g., 4-8 weeks), as shown by arrow 832 the aneurysm 808 can be created and the device 810 can be removed (FIG. 22B).

The same device 810 (or any of the other embodiments described below) can be used to study the efficacy of drugs for treating the aneurysm 808 (or other vascular disease state) in the same or different animal. Alternatively, the animals with the induced aneurysm 808 (or other vascular disease state) can be used in studies to test medical implants, such as stents and grafts. Moreover, the animals with the induced aneurysm 808 (or other vascular disease state) can be used for surgery education and for studying vascular biology in general. Further, as introduced above, the device 810 (or any of the device embodiments described below) can be used to deliver a therapeutic agent (e.g., to treat an aneurysm, as depicted in FIG. 22A) and treat vascular disease in a human patient.

When the desired blood vessel is a portion of a blood vessel (e.g., an artery) which includes additional blood vessels (e.g., arteries) branching off it (e.g., to carry blood flow to other organs/portions of the body), delivering a therapeutic agent to the desired blood vessel or portion of the blood vessel may also result in the therapeutic agent being carried away to other organs/portions of the body by the branching blood vessels. This may increase toxicity to the body and/or reduce the therapeutic agent's effectiveness in treating the target blood vessel wall.

Thus, in some embodiments, the implantable device described above can include a sealing member configured to block the therapeutic agent delivered to the outer chamber/therapeutic agent receiving lumen from entering a portion of the wall of the blood vessel in which it is implanted that includes openings to the branching blood vessels. In some embodiments, the sealing member, in combination with one or more lumens or chambers of the device, can act as a baffle that seals against the portion of the wall of the blood vessel that includes the openings to the branching blood vessels. As a result, the therapeutic agent delivered to the outer chamber/lumen may only enter another portion of the wall of the blood vessel that does not contain any openings to the branching blood vessels.

In this way, the multi-lumen implantable device may provide targeted drug delivery to only a portion of a wall of a blood vessel in which it is implanted (the portion not containing openings to any branching blood vessels). For example, the outer chamber/therapeutic agent receiving lumen of the device may only span and fluidly interface with a portion of an entire circumference of the blood vessel in which it is implanted.

FIGS. 23-40 illustrate embodiments of a multi-lumen implantable device that comprises a first lumen configured to flow blood from an upstream end to a downstream end of the device when implanted in a blood vessel; a second lumen fluidly separated from the first lumen and configured for introducing a therapeutic agent to a selected, first portion of a wall of the blood vessel, between the upstream end and the downstream end of the device; and in certain embodiments, at least one sealing member configured to block the therapeutic agent from entering a second portion of the wall of the blood vessel, between the upstream end and the downstream end of the device.

FIGS. 23-38 illustrate embodiments of the multi-lumen implantable device where the device comprises a radially expandable frame including an upstream annular portion arranged at the upstream end, a downstream annular portion arranged at the downstream end, and a central portion arranged between the upstream annular portion and the downstream annular portion, the central portion including at least one narrowed portion that indents radially inward from an outermost circumference of the frame. Additionally, in the embodiments of the device shown in FIGS. 23-38, the at least one sealing member surrounds an exterior of the frame, the first lumen is formed within an interior of the frame, and the second lumen is formed between an outer surface of the at least one sealing member and the wall of the blood vessel, when the implantable device is radially expanded within the blood vessel.

FIGS. 23-26 illustrate a first embodiment of a multi-lumen implantable device 900 having a central portion with one (e.g., a single) narrowed portion, and thus, a single lumen for receiving and introducing the therapeutic agent to the first portion of the blood vessel in which the device is implanted. The device 900 may include a similar structure and comprise similar materials to that of the stent 402, as described above with reference to FIGS. 13-16. Thus, the device 900 may be referred to as a covered stent or stent graft.

Figures 23, 24, 25, 26:
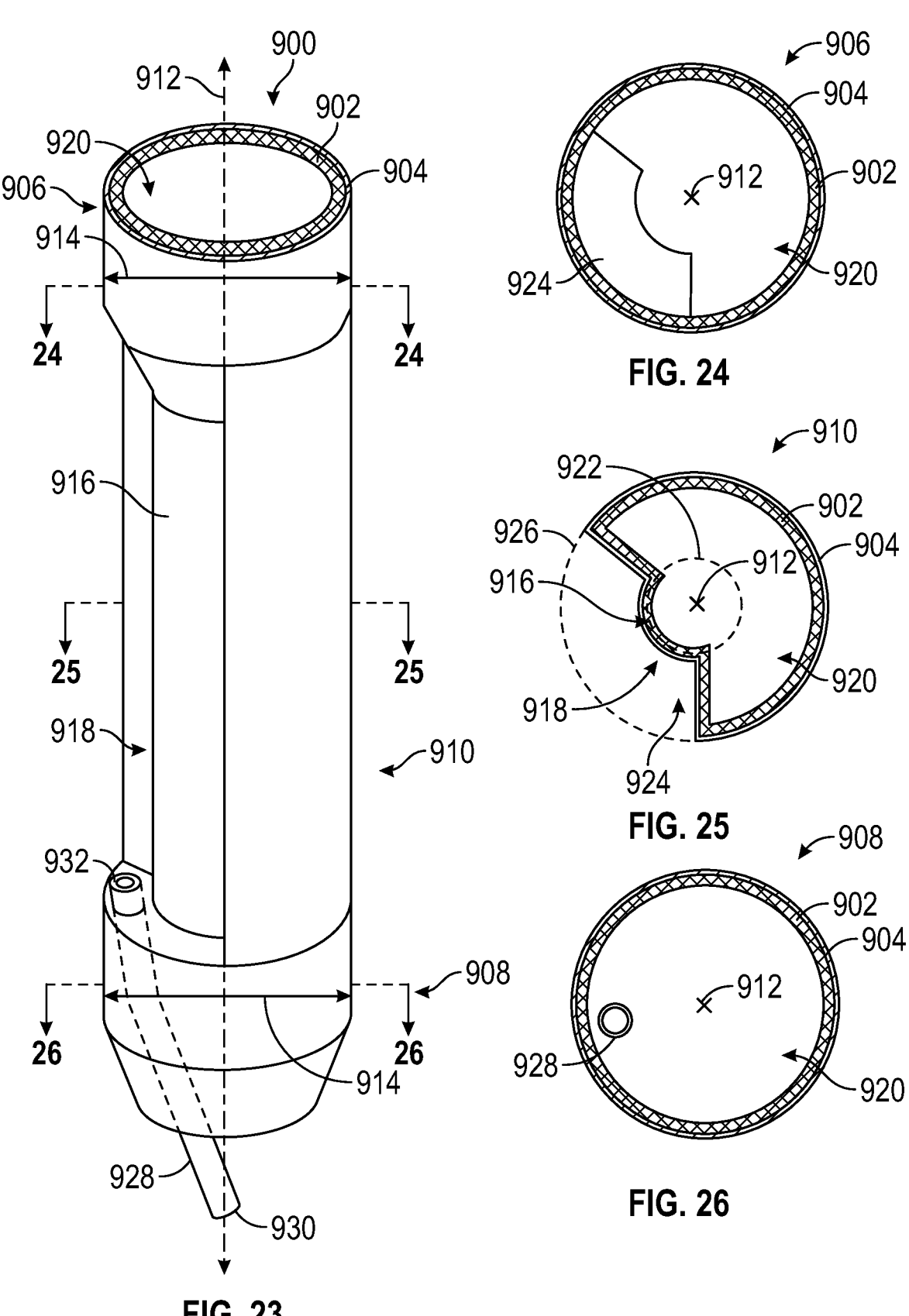
FIG. 23 is a side view of a first embodiment of a multi-lumen implantable device having a central portion with a single, narrowed portion for receiving and introducing a therapeutic agent to a portion of a blood vessel in which the device is implanted.
FIG. 24 is a cross-section view of the device of FIG. 23 taken along line 24-24 of FIG. 23.
FIG. 25 is a cross-section view of the device of FIG. 23 taken along line 25-25 of FIG. 23.
FIG. 26 is a cross-section view of the device of FIG. 23 taken along line 26-26 of FIG. 23.

FIG. 23 shows a side view of the device 900 while FIGS. 24-26 show different cross-sections of the device 900 taken at the sections indicated in FIG. 23.

The device 900 comprises a radially compressible and expandable frame (e.g., stent) 902 covered with a non-porous liner (e.g., non-fluid permeable material) 904. The device 900 and the frame 902 comprise a flared, first end portion 906, a flared, second end portion 908, and a central portion 910 arranged between the first end portion 906 and the second end portion 908, in an axial direction relative to a central longitudinal axis 912 of the device.

The liner may be similar to liner 466 of FIGS. 13-16, and thus, can be made of any of the suitable bio-compatible synthetic or biological materials described above with reference to the liner 466. For example, in some embodiments, the liner may comprise polytetrafluoroethylene (PTFE).

The frame 902 (and other frames described below) can be made of any of the frame materials discussed herein. In some embodiments, as discussed above, the frame 902 may comprise a suitable shape memory material (e.g., Nitinol).

As shown in FIGS. 23-26, the liner 904 covers an outer surface of the frame 902. However, in alternate embodiments, the liner 904 can cover an inner surface of the frame 902. In still other embodiments, the device may include two liners, one covering an inner surface of the frame 902 and one covering an outer surface of the frame 902.

Figure 27A:
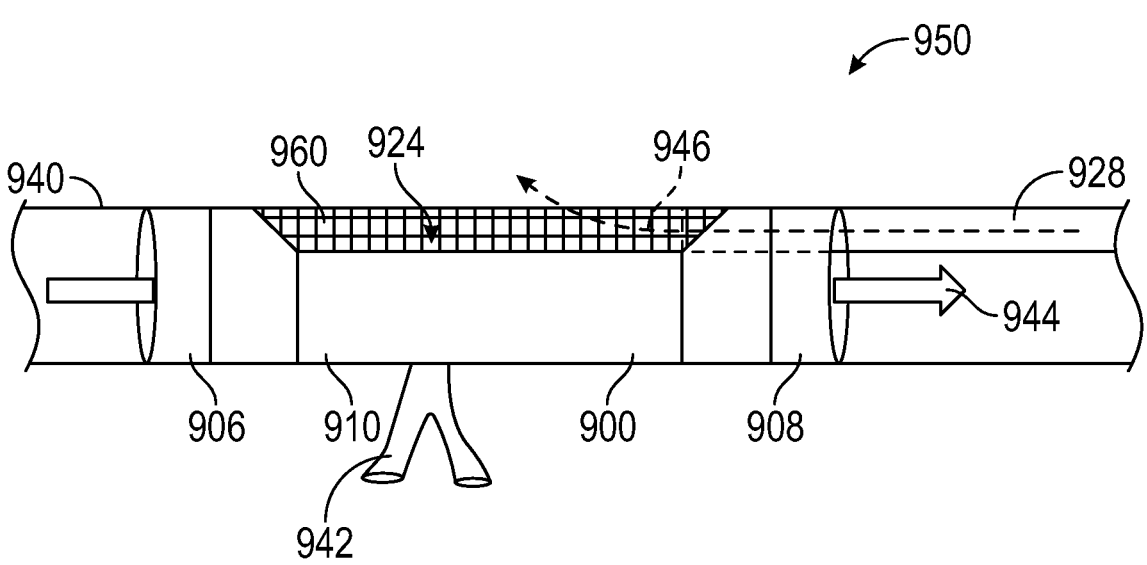
FIG. 27A is a side view of an embodiment of the device of FIG. 23, radially expanded and implanted within a blood vessel, with a sealing element configured to exclude therapeutic agents from selected branches of the blood vessel.

The first end portion 906 and the second end portion 908 are each defined by an outer diameter 914 that is selected such that the outer surfaces of the first end portion 906 and the second end portion 908 have sealing contact with an inner surface of a wall of a blood vessel when radially expanded therein (as shown in FIG. 27A, as described further below). As shown in FIG. 23, the first end portion 906 is widest at its outer end and the second end portion 908 has a narrower portion at its outer end and then widens to the outer diameter 914 proximate to the central portion 910. The proximal end of the device can include a converging portion, which can be permanently connected to a wire or shaft that extends outside the body, such as in FIGS. 19A-19C to facilitate recapture of the device back into the sheath for removal from the body.

However, in alternate embodiments, both the end portions may be widest at their outer ends (e.g., both end portions may resemble the first end portion 906, such that the second end portion 908 is inverted from how it is shown in FIG. 23—similar to the embodiment of device 900 shown in FIG. 27A).

As shown in FIGS. 23 and 25, the central portion 910 has a first indented portion 916 that indents radially inward, toward the central longitudinal axis 912, from the first end portion 906 and the second end portion 908, forming a cavity 918 on an exterior of the covered frame, between the first end portion 906 and the second end portion 908. As shown in FIG. 25, the cross-section of the cavity 918 is defined by a curved portion and two straight portions arranged on either side of the curved portion of the first indented portion 916. In alternate embodiments, the cavity 918 may have a different sized or shaped cross-section. For example, the size (e.g., including its arc length) of the cavity 918 may selected based on a size of the target blood vessel (in which the device 900 is implanted) and a size of the portion of the blood vessel containing openings to branching blood vessels. For example, if the portion of the blood vessel containing the openings to branching blood vessels is smaller, the arc length and overall size of the cavity 918 may be longer/larger.

A first lumen (e.g., blood flow lumen) 920 of the device 900 is formed by an inner surface of the liner 904. Specifically, the first lumen 920 is arranged inside the frame 902 and extends from an outer end of the first end portion 906, through the central portion 910, and to an outer end of the second end portion 908. Thus, the first lumen 920 is configured to flow blood from the first end portion 906, through the central portion 910, and to the second end portion 908. As shown in FIG. 25, within the central portion 910, the first lumen 920 has a cross-section that partially arcs around an outer perimeter of the device 900 (with a radius that is half the diameter 914) and then indents inwardly toward the central longitudinal axis 912.

In some embodiments, the first lumen 920 may be cylindrical and may not extend to an outer perimeter of the device 900 (e.g., may only be a cylindrical portion centered along the central longitudinal axis 912, as shown by the dashed line circle 922). In this embodiment, the frame may extend around the dashed circle 922 and an additional liner may be arranged on the inside or outside of the cylindrical portion of the frame such that blood flow remains within the inside of the dashed circle 922. Then, the area outside of the frame shown by the dashed circle 922 may be dead space (e.g., no fluid flow) and may function as the baffle that blocks the therapeutic agent from reaching the portion of the blood vessel wall that it seals against.

Returning to FIGS. 23-26, a second lumen (e.g., drug delivery lumen) 924 is formed within the cavity 918, between an outer surface of the liner 904 and a first portion 926 of an inner wall of the blood vessel (indicated by dashed line in FIG. 24) when the device 900 is implanted in the blood vessel. The second lumen 924 may include a bare metal stent component to maintain the potential space of the second lumen against dynamic compression of the pulsatile center lumen. The second lumen 924 is fluidly separated from the first lumen 920 by the liner 904 and is configured to deliver a therapeutic agent to the first portion 926 of the inner wall of the blood vessel.

For example, the device 900 can further include a perfusion conduit 928 defining a perfusion lumen arranged within and extending through one of the end portions 906 and 908 (from an outer side of the end portion into the second lumen 924 (FIGS. 23 and 26). In some embodiments, as shown in FIGS. 23 and 26, the perfusion conduit 928 is arranged in the second end portion 908. The perfusion conduit 928 may be configured to receive and deliver a therapeutic agent to the second lumen 924 (e.g., via a catheter or cannula attached to its outer end 930 which is located outside of the patient for access by the clinician). As shown in FIG. 23, an opposing, inner end 932 of the perfusion conduit 928 is arranged within the second lumen 924.

Figure 32:
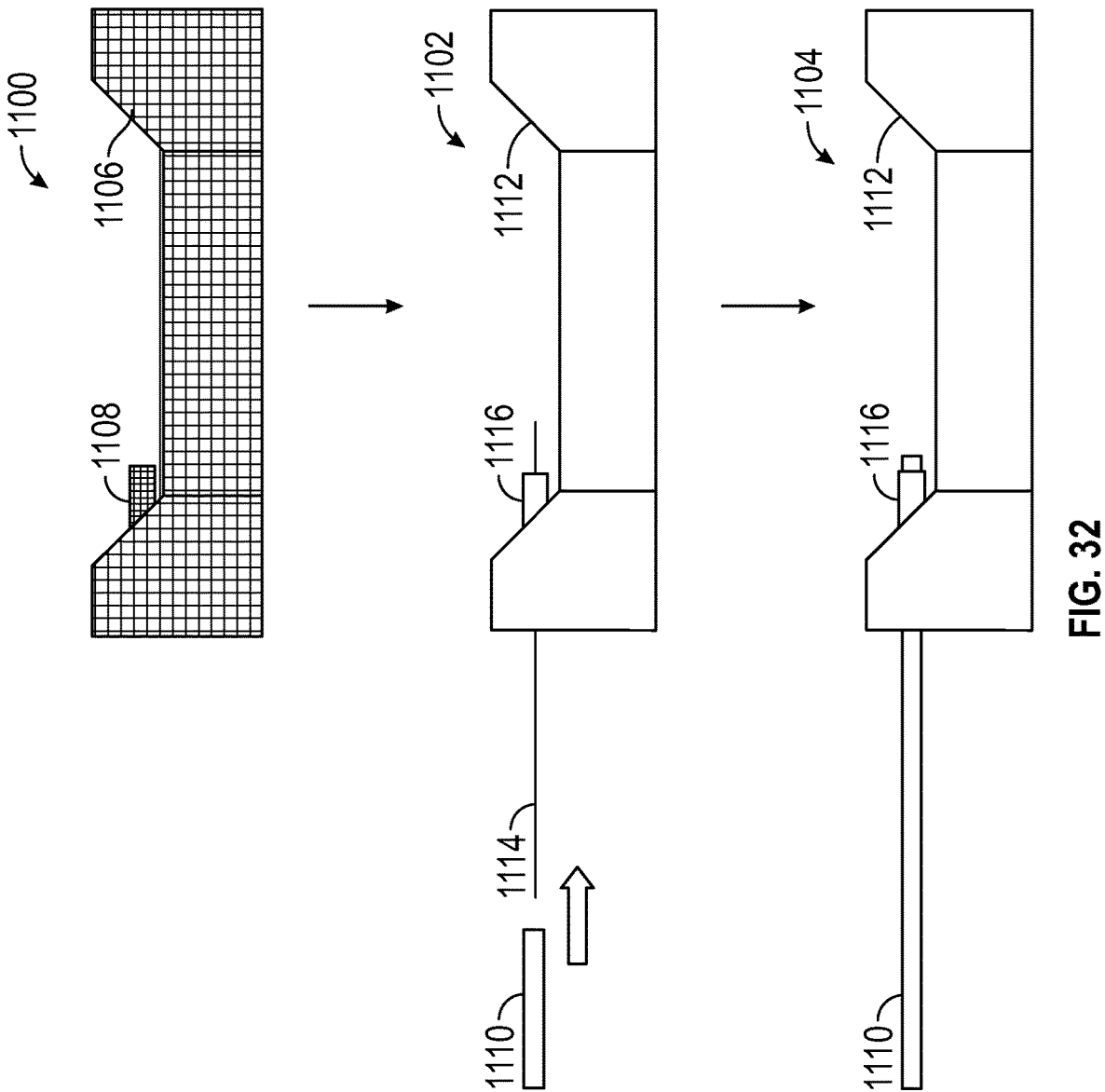
FIG. 32 illustrates a method of manufacturing a multi-lumen implantable device comprising a radially expandable frame and a sealing member, as well as depicting a modular nature of a perfusion lumen of the device which can be directed over a wire to a docking site on the device.

The perfusion conduit 928 (or 1020 or 1110) may be either integrated to the multi-lumen device or may be delivered, as shown in FIG. 32 (described further below), as a separate modular component over a guidewire 1114 to dock with the multi-lumen device at a fluid sealing docking site (e.g., extension portion 1116).

Figure 27B:
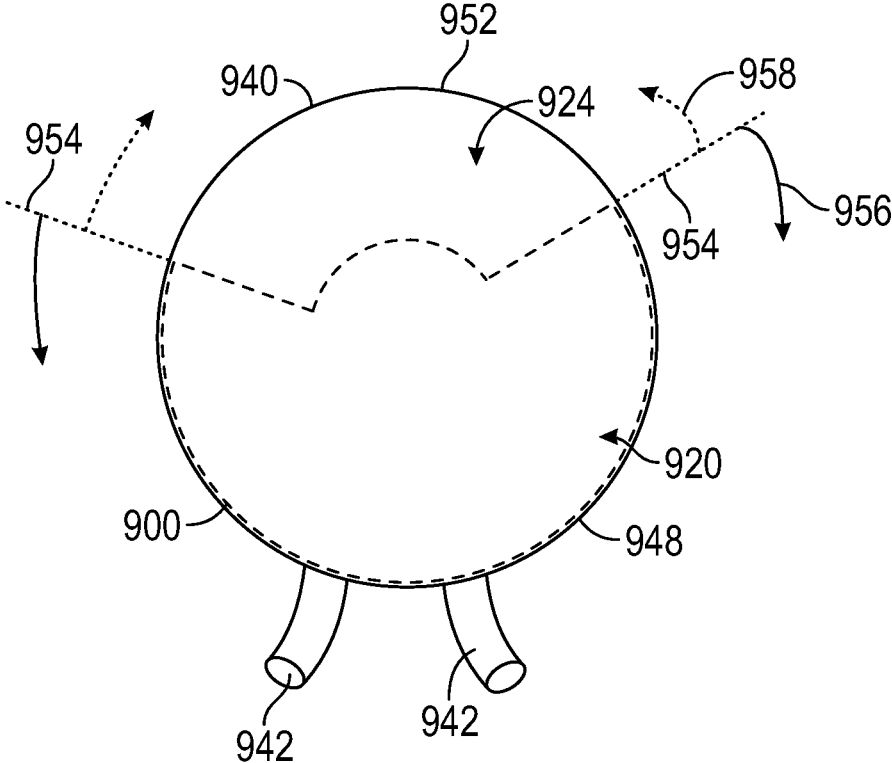
FIG. 27B is a cross-sectional view of the device of FIG. 27A implanted within the blood vessel.

FIGS. 27A and 27B illustrate an embodiment of the device 900, radially expanded and implanted within a blood vessel 940. Specifically, FIG. 27A shows a schematic 950 of a side view of the device 900 implanted in the blood vessel 940 and FIG. 27B shows a cross-section of the schematic 950. In FIG. 27B, the dashed line indicates the covered frame of device 900.

As shown in FIGS. 27A and 27B, the segment of blood vessel 940 in which the device 900 is implanted includes branching arteries 942. The branching arteries 942 may carry blood flow to additional portions (e.g., organs) of the body. A direction of blood flow through the first lumen 920 of the device 900 is indicated by arrow 944 in FIG. 27A (which is into the page in FIG. 27B).

A therapeutic agent 946 for treating a condition of the blood vessel 940 is delivered, via the perfusion conduit 928 to the second lumen 924. However, since it may not be desirable to deliver the therapeutic agent to the systemic circulation via the branching arteries 942 (e.g., due to potential toxicity), the device 900 is arranged within the blood vessel 940 such that an outer wall of a cylindrical portion (e.g., non-indented portion) of the covered frame is positioned against a first portion 948 of an inner wall of the blood vessel 940 which contains openings to the branching arteries 942. In this way, the cylindrical portion of the covered frame (in the central portion 910 of the device) acts as a seal to block the therapeutic agent 946 from entering the branching arteries 942.

As shown in FIG. 27B, the first portion 948 is arranged between the dashed lines 954, in the direction of arrows 956 and a remaining, second portion 952 of the inner wall of the blood vessel 940 is arranged between the dashed lines 954, in the direction of arrows 958. In this way, the first portion 948 and the second portion 952 can make up an entire circumference of the blood vessel 940. Since the second lumen 924 is arranged adjacent to, in the radial direction, the second portion 952 of the inner wall of the blood vessel 940, the therapeutic agent 946 is delivered to only the second portion 952 (and not the first portion 948). As a result, toxicity to additional organs and systems of the body is reduced and the effectiveness of the therapeutic agent in treating the second portion 952 of the blood vessel 940 may be increased.

In some embodiments, as shown in FIG. 27A, the second lumen (e.g., chamber) 924 can include an additional stent frame 960 arranged therein and configured to hold the second lumen 924 open. The stent frame 960 may be a bare metal stent (e.g., not covered by a liner), and thus, does not inhibit flow of the therapeutic agent 946 into the second lumen 924 and to the second portion 952 of the inner wall of the blood vessel 940.

Turning now to FIGS. 28-31, another embodiment of a multi-lumen implantable device 1000 having a central portion with a single, narrowed portion for receiving and introducing a therapeutic agent to a portion of a blood vessel in which the device is implanted is illustrated. Device 1000 may be similar to device 900 (described above with reference to FIGS. 23-27B), with only a few structural differences in the shape of the end portions and lumens, as described further below. However, the overall structure and function of device 1000 (as compared to device 900) may remain the same, and thus may not be redescribed below for the sake of brevity.

Figures 30, 31:
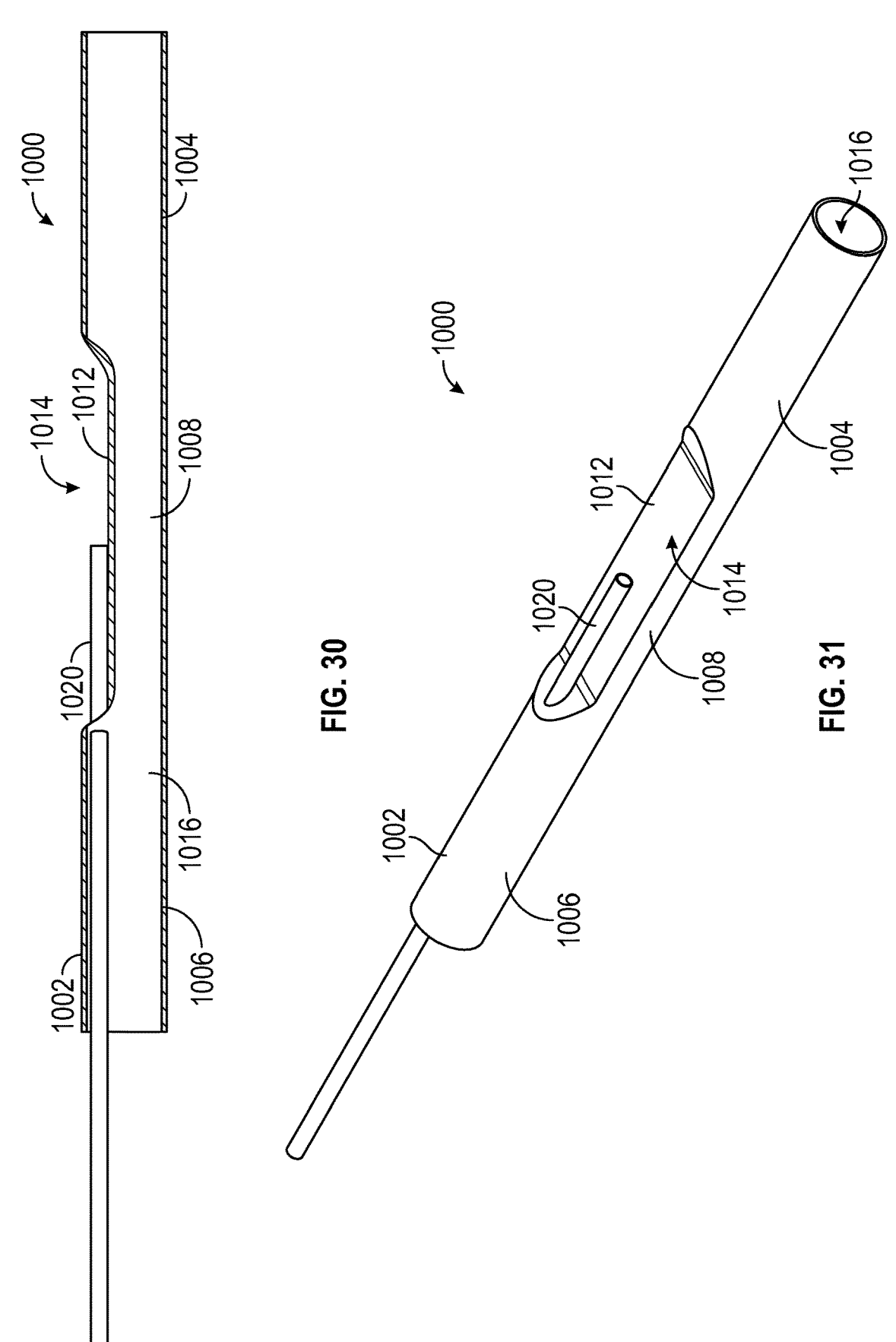
FIG. 30 is a sectional side view of the device of FIG. 28.
FIG. 31 is a perspective view of the device of FIG. 28.

FIGS. 28-31 show different views of device 1000, including a top view (FIG. 28), side view (FIG. 29), a sectional side view (FIG. 30), and a perspective view (FIG. 31). Similar to device 900, device 1000 comprises a radially compressible and expandable frame (e.g., stent) covered with a non-porous liner (e.g., non-fluid permeable material), which are represented together as a covered frame 1002 in FIGS. 28-31. The device 1000 comprises a wider (e.g., flared), first end portion 1004, a wider, second end portion 1006, and a central portion 1008 arranged between the first end portion 1004 and the second end portion 1006, in an axial direction relative to a central longitudinal axis 1010 of the device.

Figures 28, 29:
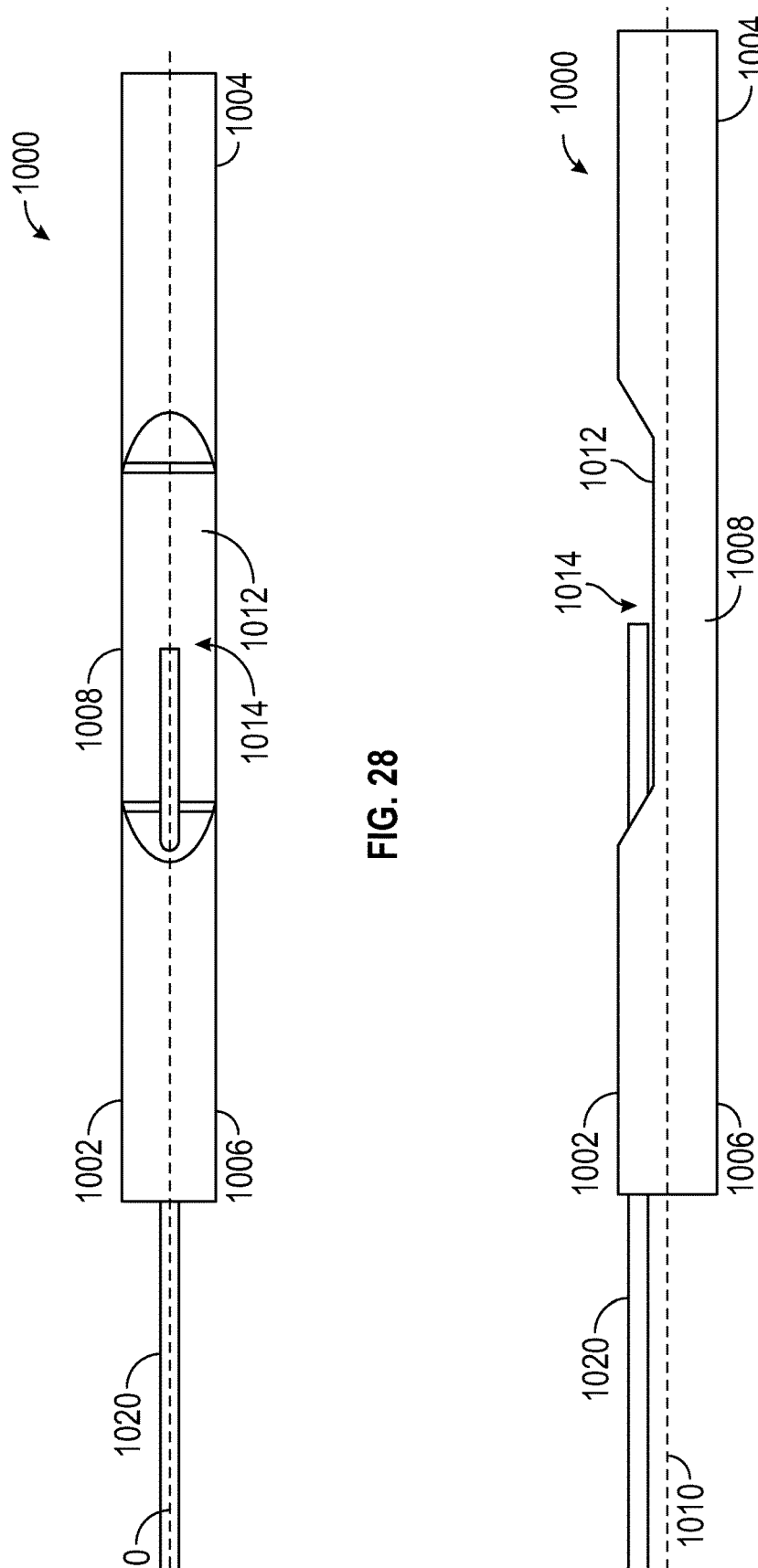
FIG. 28 is a top view of a second embodiment of a multi-lumen implantable device having a central portion with a single, narrowed portion for receiving and introducing a therapeutic agent to a portion of a blood vessel in which the device is implanted.
FIG. 29 is a side view of the device of FIG. 28.

The central portion 1008 has a first indented portion 1012 that indents radially inward, toward the central longitudinal axis 1010, from the first end portion 1004 and the second end portion 1006, forming a cavity 1014 on an exterior of the covered frame 1002, between the first end portion 1004 and the second end portion 1006. As shown in FIGS. 28 and 31, the first indented portion 1012, forming the cavity 1014, can comprise a planar portion arranged between opposing angled portions (which angle inward to the planar portion from respective end portions 1004 and 1006).

A first lumen (e.g., blood flow lumen) 1016 of the device 1000 is formed by an inner surface of the covered frame 1002 (as best seen in FIGS. 30 and 31). A second lumen (e.g., drug delivery lumen) is formed within the cavity 1014, between an outer surface of the covered frame 1002 and an inner wall of a blood vessel when the device 1000 is implanted in the blood vessel. The second lumen is fluidly separated from the first lumen 1016 by an outer surface of the covered frame 1002 and is configured to deliver a therapeutic agent to a portion of the inner wall of the blood vessel (e.g., the portion facing the cavity 1014).

For example, the device 1000 further includes a perfusion conduit 1020 defining a perfusion lumen arranged within and extending through one of the end portions 906 and 908 (from an outer side of the end portion) into the second lumen. In some embodiments, as shown in FIGS. 28-31, the perfusion conduit 1020 is arranged in the second end portion 1006. The perfusion conduit 1020 may be configured to receive and deliver a therapeutic agent to the second lumen (e.g., via a catheter or cannula attached to its outer end).

Figures 35A, 35B, 36:
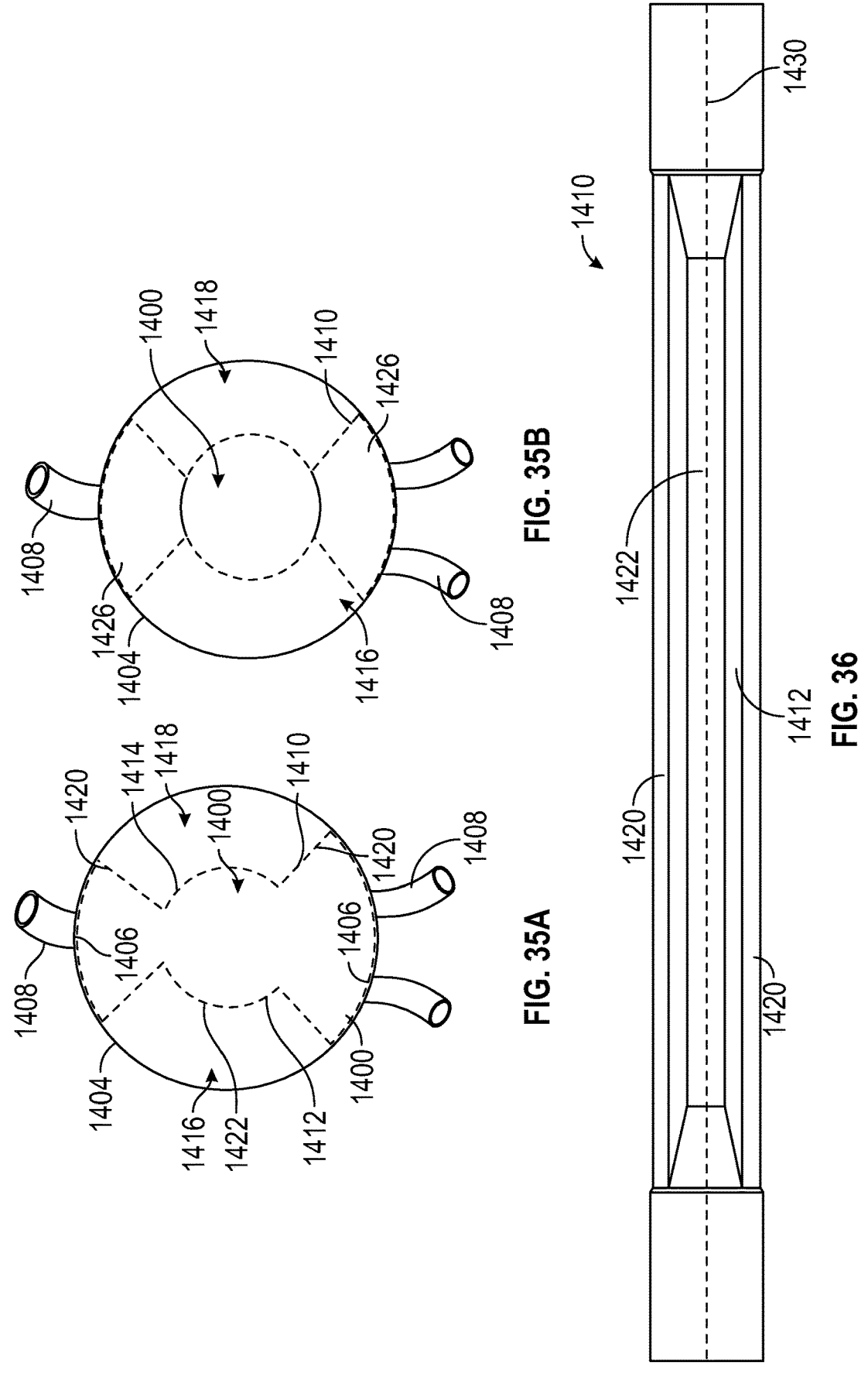
FIG. 35A is a cross-sectional view of a multi-lumen implantable device, according to an embodiment, implanted in a blood vessel with branching blood vessels, the device having a central portion with multiple narrowed portions, and thus, multiple lumens for receiving and introducing a therapeutic agent to multiple portions of a wall of the blood vessel, while multiple baffle-like portions of the device are configured to exclude a flow of the therapeutic agent into the branching blood vessels.
FIG. 35B is a cross-sectional view of a multi-lumen implantable device, according to another embodiment, implanted in a blood vessel with branching blood vessels, the device having a central portion with multiple narrowed portions, and thus, multiple lumens for receiving and introducing a therapeutic agent to multiple portions of a wall of the blood vessel, while multiple baffle-like portions of the device are configured to exclude a flow of the therapeutic agent into the branching blood vessels.
FIG. 36 is a top view of the device of FIG. 35A.
Figure 37:
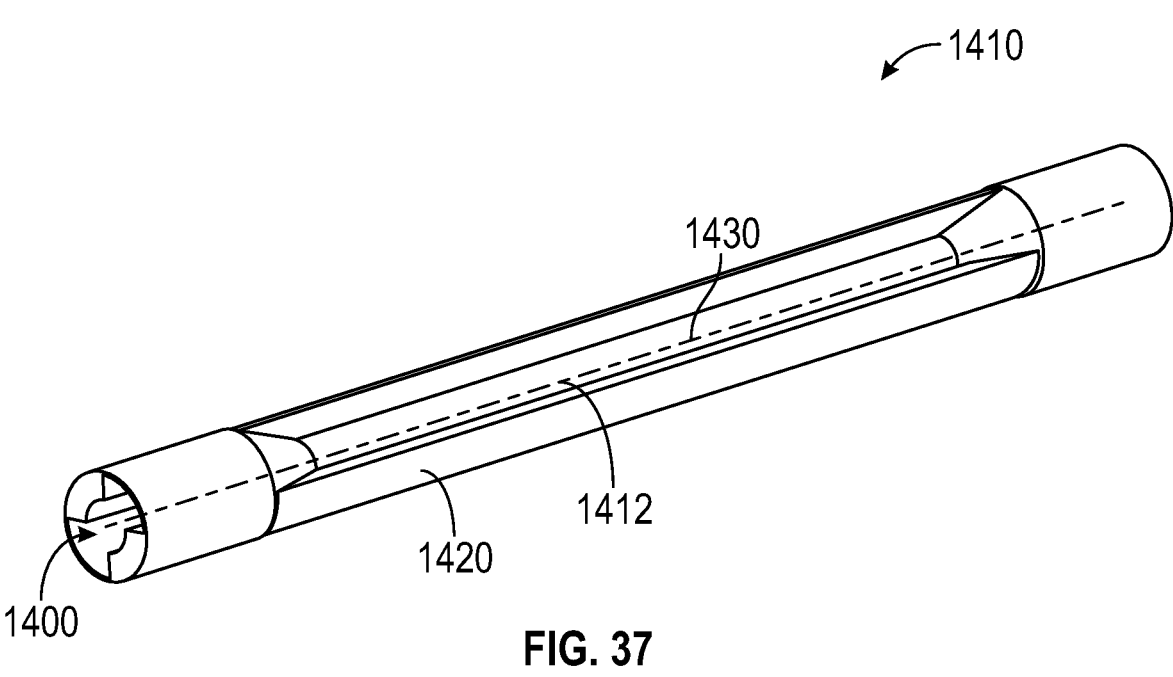
FIG. 37 is a first perspective view of the device of FIG. 35A.
Figure 38:
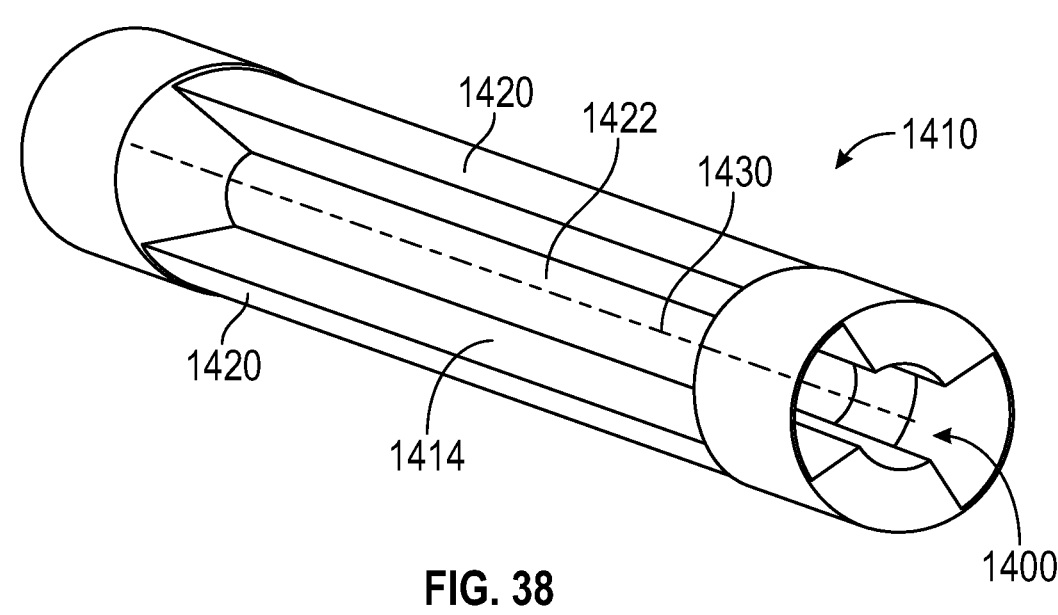
FIG. 38 is a second perspective view of the device of FIG. 35A.

FIG. 32 shows a method of manufacturing a multi-lumen implantable device, such as one the multi-lumen implantable devices 900 (shown in FIGS. 23-27B), 1000 (shown in FIGS. 28-31), 1200 (shown in FIGS. 33 and 34), or 1410 (shown in FIGS. 36-38). Additionally, FIG. 32 depicts a modular nature of a perfusion lumen of the device 900 which can be directed over a wire to a docking site on the device 900. For example, in some embodiments, due to a larger size (e.g., larger diameter) of the perfusion lumen, the perfusion lumen may not be able to be delivered as a single unit, and instead may be more easily delivered as a module over a wire to the main frame of the device.

As shown at 1100, the method can include manufacturing (e.g., building) a frame 1106 of the device (which may be a bare metal stent, comprising Nitinol in some embodiments). As discussed herein, the frame 1106 is adapted to be radially compressed for delivery to a target blood vessel and then radially expanded therein (e.g., via a balloon of a balloon delivery catheter or via self-expansion). Similar to devices 900 and 1000 described above, the frame 1106 can comprise a central portion arranged between two flared end portions. As shown in FIG. 32, the frame 1106 includes a cylindrical extension portion 1108 resembling a chimney which serves as a docking site that is configured to receive the perfusion lumen 1110.

As shown at 1102, the method can include covering the frame 1106 (including the cylindrical extension portion 1108) with a non-porous liner 1112. The liner 1112 may comprise any of the materials described herein with reference to a liner or covering of the frame. For example, in some embodiments, the liner 1112 may comprise a polymer fabric which serves as a fluid barrier. In some embodiments, an outer surface of the frame 1106 is covered with the liner 1112. In other embodiments, an inner surface of the frame 1106 is covered with the liner 1112. In yet other embodiments, both the inner surface and the outer surface is covered with the liner (e.g., multiple liners) 1112.

As shown at 1104, the method can include inserting the perfusion conduit 1110 into the covered extension portion 1116 via a guidewire 1114. The guidewire 1114 can be a pre-placed wire through the docking site provided by the covered extension portion 1116. The covered extension portion 1116 forms a fluid seal between the perfusion lumen and the blood flow lumen (arranged within an interior of the covered frame) of the device.

In alternate embodiments, instead of a modular perfusion lumen 1110, the perfusion lumen can be integrated with the frame 1106 to form a single delivery unit.

Figures 33, 34:
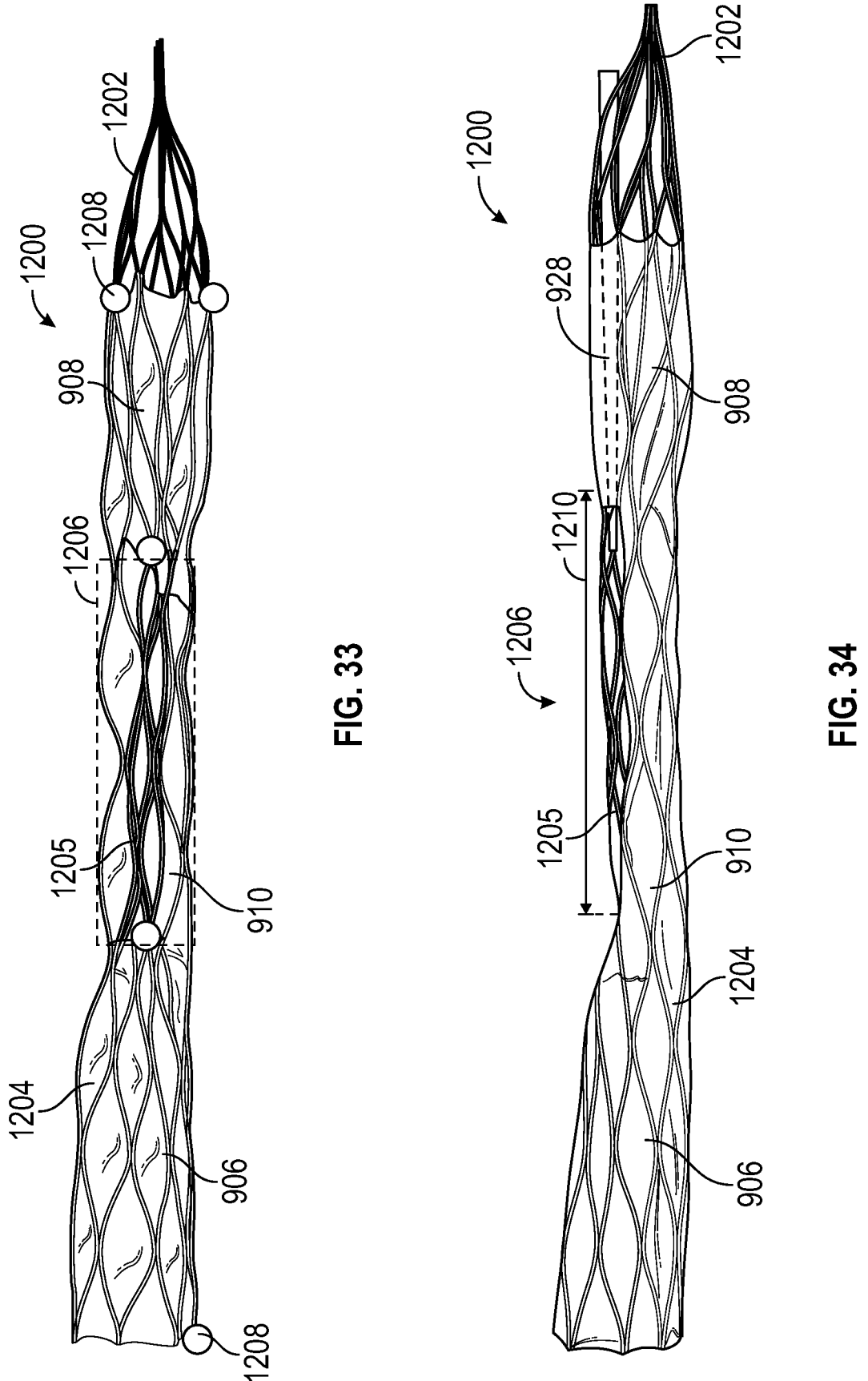
FIG. 33 is a top view of a prototype multi-lumen implantable device including an additional support frame disposed in an agent receiving lumen of the device, according to an embodiment.
FIG. 34 is a side view of the device of FIG. 33.

FIGS. 33 and 34 illustrate a prototype multi-lumen implantable device 1200 which may be the same or similar to the embodiment of device 900 shown in FIGS. 26 and 27. Thus, similar parts or portions between device 900 of FIGS. 26 and 27 and device 1200 are labeled similarly in FIGS. 33 and 34 and are not re-described below. The device 1200 comprises a radially expandable frame 1202 covered by a non-porous liner (referred to herein as a sealing member) 1204.

As described above, a blood flow lumen is formed within an interior of the covered frame and is fluidly separated from a drug delivery (therapeutic agent receiving) lumen, which may be referred to as a chamber 1206 which is indicated by the dashed box in FIG. 33. The chamber 1206 is adapted to receive a therapeutic agent from the perfusion conduit 928. A length 1210 of the chamber 1206 is shown in FIG. 34.

In some embodiments, as shown in FIGS. 33 and 34, the device 1200 includes an additional, support frame (e.g., stent) 1205 arranged within the chamber 1206. This may provide additional support to keep the chamber 1206 open and resist dynamic compression from the pulsatile center lumen to be able to receive the therapeutic agent. At the same time the covered central portion 910 of the frame acts to block the flow of therapeutic agents to branches (e.g., posterior branches) of the blood vessel in which the device is implanted. In some embodiments, the chamber 1206 may be referred to as an anterior chamber and the portion of the covered frame in the central portion 910 may be preferred to as a posterior sealing member (or baffle).

In some embodiments, as shown in FIG. 33 and described above with reference to other apparatus and device embodiments, the device 1200 can include one or more positioning markers (which can be, for example, radiopaque markers or sensors, such as RFID sensors or magnetic sensors) 1208. In this way, the device 1200, and particularly the chamber 1206, may be accurately positioned in a target blood vessel such that a desired portion of the blood vessel receives the therapeutic agent (via chamber 1206), while another selected portion of the blood vessel is blocked from receiving the therapeutic agent (e.g., via the outer wall of the covered frame, which can be referred to as a baffle or baffle portion of the device).

Turning now to FIGS. 35-38, another embodiment of a multi-lumen implantable device 1410 having a central portion with multiple (e.g., two) narrowed (e.g., indented) portions, and thus, multiple lumens for receiving and introducing the therapeutic agent to multiple (but not all) portions of the wall of the blood vessel in which the device is implanted is illustrated. Additionally, the device 1410 has multiple baffle-like portions that are configured to exclude a flow of the therapeutic agent into branches of the blood vessel. For example, device 1410 may be similar to device 1000 shown in FIGS. 28-31, but with two, separate indented portions forming respective, fluidly separate, cavities (which form therapeutic agent-receiving lumens when implanted in a blood vessel).

FIGS. 35A and 35B show two embodiments of device 1410 implanted (in its radially expanded state) in a blood vessel 1404. The blood vessel 1404 includes a plurality of openings 1406 to branching arteries 1408. The dashed lines of FIGS. 35A and 35B represent a covered (e.g., via a non-porous liner) frame of the device 1410.

FIGS. 36-38 illustrate different views of the device 1410 comprising a covered (e.g., via a non-porous liner) frame that includes a central portion arranged between opposing, flared end portions.

As shown in FIGS. 35A-38, the central portion of the device 1410 includes a first cavity (or depression) 1412 and second cavity (or depression) 1414, which form a second lumen 1416 and third lumen 1418, respectively, when implanted in the blood vessel 1404 (lumens shown in FIGS. 35A and 35B).

In a first embodiment, as shown in FIG. 35A and FIGS. 36-38, a first (blood flow) lumen 1400 is arranged within a central portion 1422 of the covered frame of the device 1410 and two radially, outwardly extending portions 1420 of the covered frame of the device 1410, where each of the first cavity 1412 and the second cavity 1414 are arranged between outer surfaces of the two radially outwardly extending portions 1420. The outwardly extending portions 1420 extend radially outward from the central portion 1422, relative to a central longitudinal axis 1430 of the device 1410.

The outwardly extending portions 1420 of the covered frame each form a baffle-like portion that blocks the therapeutic agent from entering branching arteries 1408 of the blood vessel 1404. Specifically, the baffle-like portions block the therapeutic agent from flowing from the second lumen 1416 and the third lumen 1418 into the branching arteries 1408.

In a second embodiment, as shown in FIG. 35B, the first (blood flow) lumen 1400 is arranged within only the central portion 1422 of the covered frame of the device 1410. The frame of the central portion 1422 may include an additional covering (e.g., liner or sealing member) that blocks blood from entering the radially outwardly extending portions 1420 (which may be covered, baffle-like portions 1426 of the frame that are fluidly separated from each of the first lumen 1400, second lumen 1416, and third lumen 1418). This is in contrast to the embodiment of FIG. 35A where the baffle-like portions are an extension of the central lumen, but still block flow into the branching arteries 1408.

In both embodiments, the outwardly extending portions 1420 are configured to seal against the portions of the inner surface of the blood vessel 1404 containing the openings 1406 to the branching arteries 1408. As such, the therapeutic agent delivered to the second lumen 1416 and the third lumen 1418 is blocked from entering the branching arteries 1408.

As shown in FIGS. 35-38, the baffle-like portions are arranged anteriorly and posteriorly to block the flow of therapeutic agent to the anterior and posterior branches of the blood vessel. However, in alternate embodiments, the multi-lumen device 1410 may have different numbers or configurations of the outwardly extending (e.g., baffle-like) portions 1420 or 1426. For example, the device 1410 may have one, three, four, or the like, outwardly extending (e.g., baffle-like) portions configured to block the flow of a therapeutic agent into selected portions of the blood vessel. The number and/or size of these baffle-like portions can be selected based on the intended vessel (e.g., based on the number and/or arrangement of branching vessels where a flow of therapeutic agent is not desired).

Figure 39:
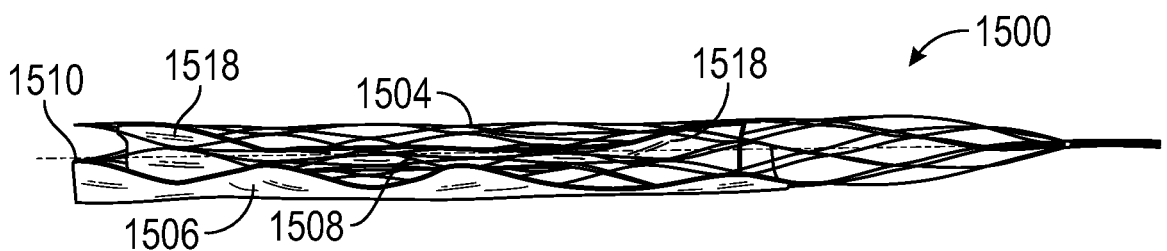
FIG. 39 is a side view of an alternate embodiment of a multi-lumen implantable device having a baffle-like portion configured to block a flow of a therapeutic agent to branching vessels, the device including two nested, radially expandable frames and two sealing members.
Figure 40:
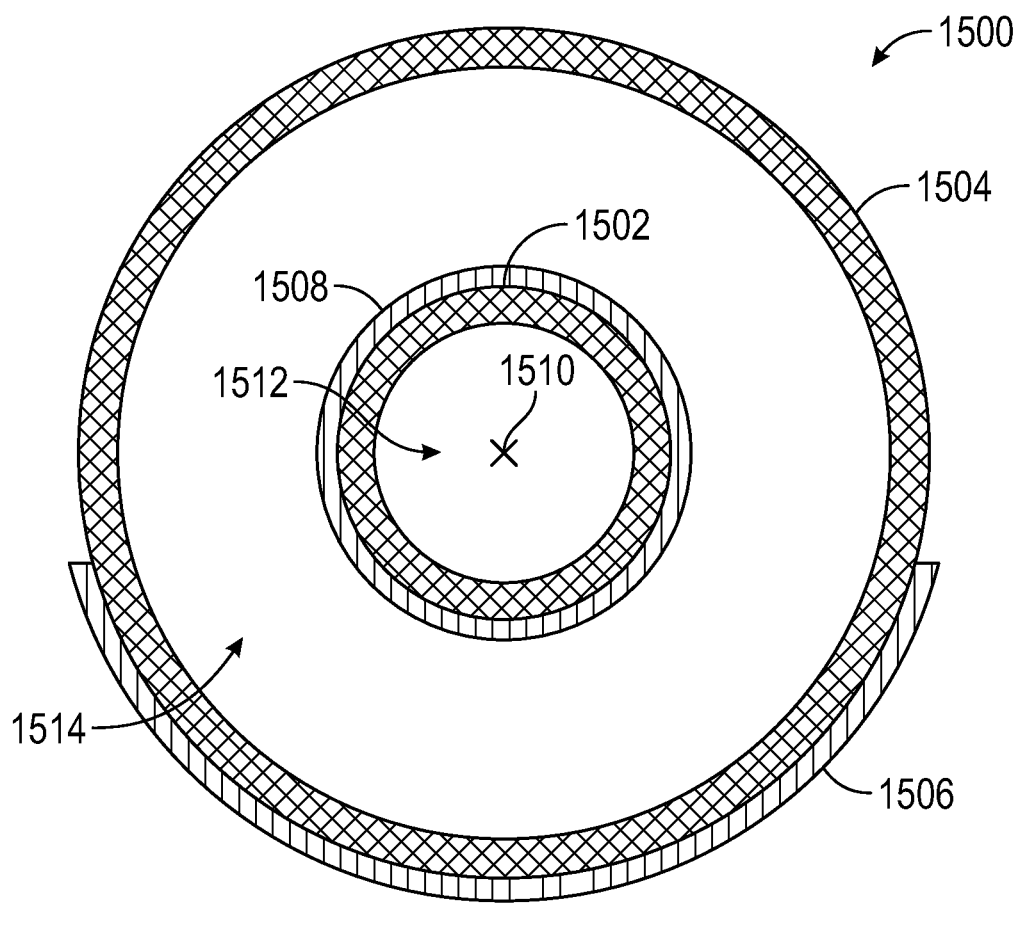
FIG. 40 is a cross-sectional view of the device of FIG. 39.

FIGS. 39 and 40 illustrate another embodiment of a multi-lumen implantable device 1500 having a baffle-like portion configured to block a flow of therapeutic agent to a selected portion of the blood vessel (e.g., to branching vessels of the blood vessel). In the embodiment of FIGS. 39 and 40, an outer covered frame of the device 1500 serves as a baffle-like portion adapted to exclude flow of therapeutic agent to branches (e.g., posterior branches) of the blood vessel.

For example, as shown in FIGS. 39 and 40, the device 1500 comprises a radially expandable first, inner frame 1502 and a radially expandable second, outer frame 1504, the second frame 1504 surrounding an entire circumference of the first frame 1502, relative to a central longitudinal axis 1510 of the device 1500. Additionally, the device 1500 comprises at least one sealing member (e.g., first sealing member) 1506 that covers an outer surface of a selected portion of the second frame 1504. Additionally, the device 1500 includes a second sealing member 1508 surrounding an outer surface of the first frame 1502, where the first (blood flow) lumen 1512 is formed within an interior of the first frame 1502 by an inner surface of the second sealing member 1508 and the second (therapeutic agent receiving) lumen 1514 is formed in an annular space arranged between, in a radial direction, an outer surface of the second sealing member 1508 and the second frame 1504.

The first frame 1502 can have enlarged end portions 1518 that engage an inner surface of the second frame 1504. In this manner, the first frame 1502 can have an overall dumbbell shape, similar to the shape of the device 720 of FIG. 20A or frame 730 of FIG. 20D. The second sealing member 1508 fluidly separates the blood flow lumen 1512 from the agent receiving lumen 1514. When implanted, the first sealing member 1506 seals against a selected portion of a vessel to block the flow of an agent to that portion of the vessel or to branches in the vicinity. The uncovered portion of the second frame 1504 allows the agent to flow from the agent receiving lumen 1514 outwardly through the uncovered portion of the second frame 1504 and contact the adjacent portion of the vessel that is to be treated.

FIGS. 41A-41D illustrate fluidic separation between lumens of a multi-lumen implantable device, such as one of the multi-lumen implantable device described above. For example, the multi-lumen implantable device 1600 has a central, blood flow lumen (e.g., first lumen) and a second, therapeutic agent receiving lumen, the central lumen and second lumen fluidly separated from one another, as described above. In FIGS. 41B and 41D, angiograms of the device 1600 (schematics of fluid flow through the device shown in FIGS. 41A and 41C) show isolation of the systemic (e.g., cardiac) central lumen of the device 1600 from the outer, second lumen (e.g., visceral lumen).

Specifically, FIG. 41B shows an angiogram of blood flow 1602 through the central lumen of the device 1600 (a corresponding schematic of the device 1600 with blood flow 1602 is shown in FIG. 41A) and FIG. 41D shows an angiogram of the therapeutic agent flow 1604 through the second lumen of the device 1600 (corresponding schematic of the device 1600 shown in FIG. 41C). The therapeutic agent flow 1604 flows from the second lumen of the device 1600 into a plurality of branching arteries 1605 (such as the renal arteries), as shown in FIG. 41D.

Figure 42:
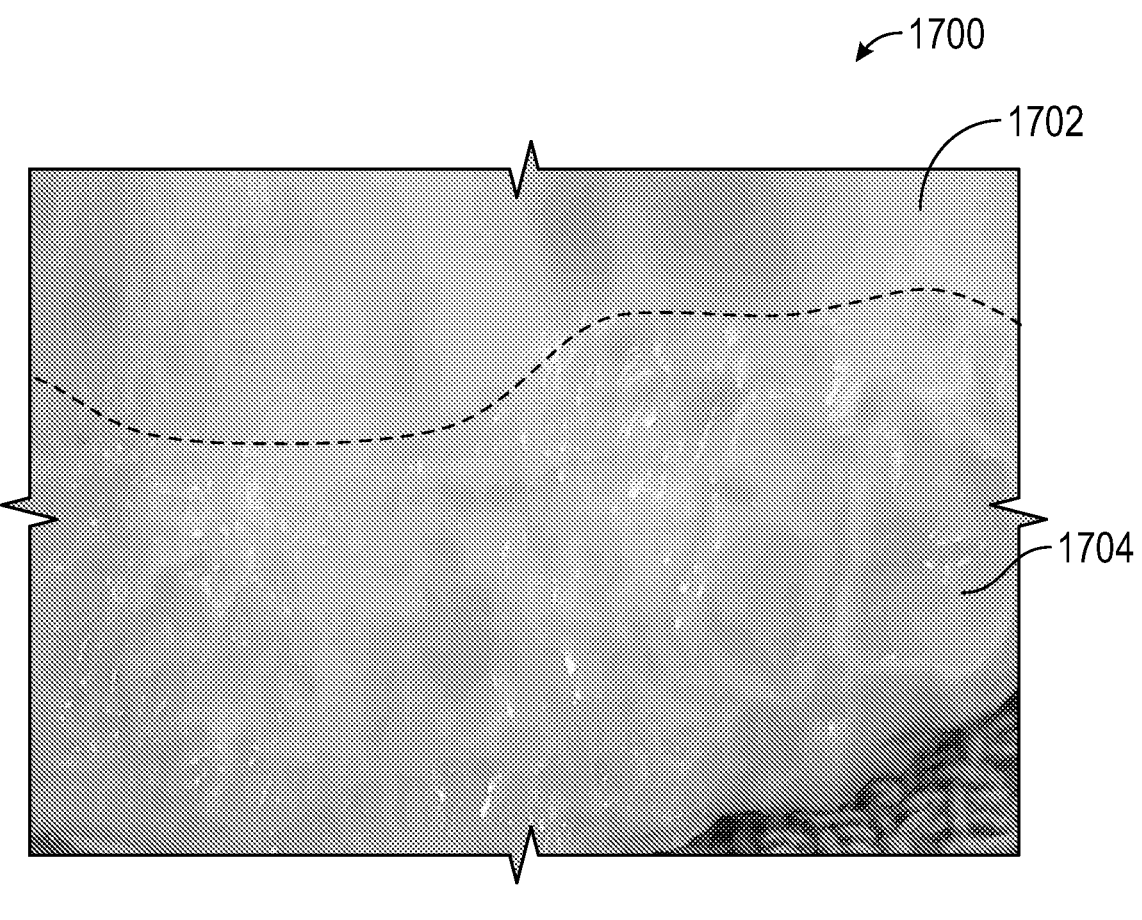
FIG. 42 illustrates an interface between a normal, non-diseased portion of an aorta and an aneurysmal portion of the aorta, where the aneurysmal aorta portion has been exposed to an aneurysm-promoting agent via a second, outer chamber of a multi-lumen implantable device.

As discussed above with reference to FIG. 22B, one of the multi-lumen implantable devices disclosed herein may be used to create a large animal disease model (such as an aneurysm model). FIG. 42 shows an interface between a normal, non-diseased portion of an aorta and an aneurysmal portion of the aorta in such a model, where the aneurysmal aorta portion has been exposed to an aneurysm-promoting agent via a second, outer chamber of a multi-lumen implantable device (e.g., the therapeutic agent receiving lumen, such as the second lumen 924 shown in FIGS. 23-26). Specifically, FIG. 42 shows a first portion (e.g., area) 1702 of an aorta 1700 not exposed to the second outer chamber (e.g., blocked via a baffle-type portion of the device) and a second portion (e.g., area) 1704 of the aorta 1700 which was exposed to the second outer chamber (and therefore receiving the aneurysm-promoting therapeutic agent). In FIG. 42, the separation between the first portion 1702 and the second portion 1704 is illustrated by a dashed line. This figure illustrates the ability of the multi-lumen devices described herein to deliver a therapeutic agent to a selected portion of a blood vessel (while being blocked to other portions) with relatively high precision.

General Considerations

For purposes of this description, certain aspects, advantages, and novel features of the embodiments of this disclosure are described herein. The disclosed methods, apparatuses, and systems should not be construed as limiting in any way. Instead, the present disclosure is directed toward all novel and nonobvious features and aspects of the various disclosed embodiments, alone and in various combinations and sub-combinations with one another. The methods, apparatuses, and systems are not limited to any specific aspect or feature or combination thereof, nor do the disclosed embodiments require that any one or more specific advantages be present or problems be solved.

Although the operations of some of the disclosed methods are described in a particular, sequential order for convenient presentation, it should be understood that this manner of description encompasses rearrangement, unless a particular ordering is required by specific language. For example, operations described sequentially may in some cases be rearranged or performed concurrently. Moreover, for the sake of simplicity, the attached figures may not show the various ways in which the disclosed methods can be used in conjunction with other methods. As used herein, the terms "a", "an" and "at least one" encompass one or more of the specified element. That is, if two of a particular element are present, one of these elements is also present and thus "an" element is present. The terms "a plurality of" and "plural" mean two or more of the specified element.

As used herein, the term "and/or" used between the last two of a list of elements means any one or more of the listed elements. For example, the phrase "A, B, and/or C" means "A," "B," "C," "A and B," "A and C," "B and C" or "A, B and C."

As used herein, the term "coupled" generally means physically coupled or linked and does not exclude the presence of intermediate elements between the coupled items absent specific contrary language.

In view of the many possible embodiments to which the principles of the disclosed technology may be applied, it should be recognized that the illustrated embodiments are only preferred examples of the disclosed technology and should not be taken as limiting the scope of the claimed subject matter. Rather, the scope of the claimed subject matter is defined by the following claims and their equivalents.

We claim:

1. A multi-lumen implantable device configured to be implanted in a blood vessel, comprising:
   a radially expandable frame covered with a non-porous liner, the radially expandable frame including a flared, first end portion, a flared, second end portion, and a central portion arranged between the first end portion and the second end portion, in an axial direction relative to a central longitudinal axis of the device, the central portion having a first indented portion that indents radially inward, toward the central longitudinal axis, from the first end portion and the second end portion, forming a cavity on an exterior of the covered frame, between the first end portion and the second end portion, wherein the cavity extends partially around a circumference of the device, along the central portion of the device;
   a first lumen configured to flow blood from the first end portion, through the central portion, and to the second end portion, the first lumen formed by an inner surface of the non-porous liner; and
   a second lumen formed within the cavity, between an outer surface of the non-porous liner and a first portion of an inner wall of the blood vessel when the device is implanted in the blood vessel, wherein the second lumen is fluidly separated from the first lumen by the non-porous liner and is configured to deliver a therapeutic agent to the first portion of the inner wall of the blood vessel, and wherein the non-porous liner is configured to block the therapeutic agent from flowing to a second portion of the inner wall of the blood vessel, between the first end portion and the second end portion of the device; and
   a perfusion conduit defining a perfusion lumen fluidly coupled to the second lumen and configured to extend outside a body of a patient, wherein the perfusion conduit extends through the second end portion of the frame, through the non-porous liner covering the second end portion and into the second lumen, such that an end of the perfusion conduit is arranged within the second lumen,
   wherein the frame comprises a docking site comprising a cylindrical extension portion extending outward from the second end portion of the frame into the second lumen, and wherein the perfusion conduit is a separate component from the frame and is configured to be inserted into the cylindrical extension portion via a guidewire.

2. The device of claim 1, wherein the cavity is a first cavity and further comprising a third lumen formed within a second cavity formed by a second indented portion of the central portion which indents radially inward from the first end portion and the second portion, at a location that is radially offset from the first cavity, wherein the third lumen is formed within the second cavity, between outer walls of the non-porous liner and the inner wall of the blood vessel when the device is implanted in the blood vessel.

3. The device of claim 1, further comprising an additional radially expandable frame arranged within the first cavity and connected to the non-porous liner.

4. The device of claim 1, wherein a portion of the non-porous liner covers a non-indented portion of the central portion of the frame, which is not indented relative to the first end portion and the second end portion and is configured to seal against the second portion of the inner wall of the blood vessel to block the therapeutic agent from flowing to the second portion of the inner wall of the blood vessel.

5. The multi-lumen implantable device of claim 1, wherein the second lumen is arranged radially offset from the first lumen and adjacent to a central portion of the first lumen.

6. The multi-lumen implantable device of claim 1, wherein the first end portion and second end portion of the frame have a first diameter and are adapted to seal against the wall of the blood vessel, and wherein the first end portion and second end portion are spaced apart from one another, in an axial direction, by the central portion.

7. The multi-lumen implantable device of claim 6, wherein a central portion of the first lumen arranged in the central portion of the frame has a second diameter that is smaller than the first diameter, and wherein the central portion of the first lumen is radially offset from the central longitudinal axis of the device.

8. The multi-lumen implantable device of claim 1, wherein the non-porous liner is configured to block one or more branch vessel openings in the second portion of the wall of the blood vessel when the device is implanted in the blood vessel.

9. The multi-lumen implantable device of claim 1, wherein the first indented portion comprises a planar portion arranged between opposing angled portions which angle inward to the planar portion from the first end portion and the second end portion, respectively.

10. The multi-lumen implantable device of claim 1, wherein the at least one non-porous liner comprises a non-fluid permeable material.

11. The multi-lumen implantable device of claim 1, wherein the frame comprises a plurality of longitudinally oriented struts that converge into a single delivery wire or shaft at a proximal end of the device, which allows the implantable device to be recaptured and removed from the body.

12. The multi-lumen implantable device of claim 1, wherein the frame comprises Nitinol.

13. The multi-lumen implantable device of claim 1, wherein the central portion of the frame has a non-circular cross-sectional profile in a plane perpendicular to the central longitudinal axis.

14. A method for delivering a therapeutic agent to a portion of a blood vessel via a multi-lumen implantable device, comprising:

delivering the device, in a radially compressed state, to a target location in the blood vessel, wherein the device comprises a radially expandable frame covered with a non-porous liner, the radially expandable frame including a flared, first end portion, a flared, second end portion, and a central portion arranged between the first end portion and the second end portion, in an axial direction relative to a central longitudinal axis of the device, the central portion having an indented portion that indents radially inward, toward the central longitudinal axis, from the first end portion and the second end portion, forming a cavity on an exterior of the covered frame, between the first end portion and the second end portion, wherein the cavity extends partially around a circumference of the device, along the central portion of the device, and wherein the device comprises a first lumen defined by an inner surface of the non-porous liner and extending through the first end portion, the central portion, and the second end portion;

radially expanding the device to seal the first end portion of the device against an upstream portion of the blood vessel seal the second end portion of the device against a downstream portion of the blood vessel;

flowing blood through the first lumen of the device;

forming an outer, bloodless void in the blood vessel, wherein the bloodless void is an enclosed cavity bounded by the first end portion of the device, the second end portion of the device, a first portion of a wall of the blood vessel facing the central portion of the device, and an outer surface of the non-porous liner covering the indented portion of the central portion of the frame of the device; and delivering a therapeutic agent to the bloodless void while flowing blood through the first lumen.

15. The method of claim 14, wherein the central portion of the frame comprises a non-indented portion covered by the non-porous liner, and wherein when the device is radially expanded, the non-indented portion seals against a second portion of the wall of the blood vessel.

16. The method of claim 15, further comprising blocking the therapeutic agent from reaching the second portion of the wall of the blood vessel via the non-indented portion.

17. The method of claim 15, wherein the non-porous liner covering the non-indented portion of the frame covers a branch vessel extending from the blood vessel and prevents the therapeutic agent from flowing into the branch vessel.

18. The method of claim 14, wherein the therapeutic agent is an aneurysm stabilizing therapeutic agent.

19. The method of claim 14, wherein the therapeutic agent is a therapeutic agent for treating a condition of the blood vessel.

* * * * *